(12) United States Patent
Alcouloumre et al.

(10) Patent No.: US 10,835,687 B1
(45) Date of Patent: Nov. 17, 2020

(54) METHOD AND APPARATUS FOR SHARPS PROTECTION

(71) Applicant: St. Joseph Health System, Irvine, CA (US)

(72) Inventors: Eric Alcouloumre, Laguna Beach, CA (US); Jay Lenker, Laguna Beach, CA (US); Richard Reedy, Laguna Beach, CA (US); Marc Habib, Huntington Beach, CA (US)

(73) Assignee: St. Joseph Health System, Irvine, CA (US)

( * ) Notice: Subject to any disclaimer, the term of this patent is extended or adjusted under 35 U.S.C. 154(b) by 727 days.

(21) Appl. No.: 15/191,218

(22) Filed: Jun. 23, 2016

Related U.S. Application Data

(60) Provisional application No. 62/183,967, filed on Jun. 24, 2015.

(51) Int. Cl.
| | | |
|---|---|---|
| *A61M 5/32* | (2006.01) | |
| *A61B 17/3217* | (2006.01) | |
| *B65D 43/16* | (2006.01) | |
| *A61B 50/33* | (2016.01) | |
| *B65D 25/20* | (2006.01) | |

(52) U.S. Cl.
CPC ....... *A61M 5/3278* (2013.01); *A61B 17/3217* (2013.01); *A61B 50/33* (2016.02); *B65D 25/205* (2013.01); *B65D 43/16* (2013.01); *A61M 2005/328* (2013.01)

(58) Field of Classification Search
CPC .......... A61M 5/3278; A61M 2005/328; A61B 17/3217; A61B 50/33; A61B 50/3001; B65D 25/205; B65D 43/16
USPC ....... 206/571, 364, 365, 366, 370, 382, 383, 206/438
See application file for complete search history.

(56) References Cited

U.S. PATENT DOCUMENTS

| | | | | |
|---|---|---|---|---|
| 4,106,620 A | * | 8/1978 | Brimmer ............ | A61B 17/3215 206/356 |
| 4,828,107 A | * | 5/1989 | Spencer .............. | A61M 5/3205 206/366 |
| 5,181,609 A | * | 1/1993 | Spielmann .......... | A61B 50/362 206/366 |
| 5,265,724 A | * | 11/1993 | Dondlinger ......... | A61M 5/3205 206/365 |
| 5,402,887 A | * | 4/1995 | Shillington ......... | A61M 5/3205 206/366 |
| 5,791,471 A | * | 8/1998 | Radmand ............... | A61C 19/00 206/366 |

(Continued)

*Primary Examiner* — Jacob K Ackun
*Assistant Examiner* — Jenine Pagan
(74) *Attorney, Agent, or Firm* — Ice Miller LLP

(57) ABSTRACT

Devices and methods are disclosed for protecting individuals from the sharp ends of medical objects following use on a patient. Such sharp objects include hypodermic needles, scalpel blades, cannulae, trocars, and the like. The protective cover is designed to surround and sequester the sharp in a shell that is will not permit further puncture or cutting with the sharp. In an embodiment, the protective cover also absorbs any fluids on or in the used sharp and prevents any fluids from escaping the protective cover. The devices are configured to be integral to procedure trays or kits such that space and discarded materials are minimized along with the potential for injuring someone with a used, contaminated medical sharp.

14 Claims, 50 Drawing Sheets

(56) References Cited

U.S. PATENT DOCUMENTS

| | | | | |
|---|---|---|---|---|
| 6,247,592 | B1* | 6/2001 | Racicot | A61M 5/3205 |
| | | | | 206/366 |
| 6,530,479 | B2* | 3/2003 | Hernandez | A61B 17/06061 |
| | | | | 206/370 |
| 7,815,046 | B2* | 10/2010 | Sansoucy | A61M 5/002 |
| | | | | 206/366 |
| 7,837,034 | B2* | 11/2010 | Clegg | A61M 5/008 |
| | | | | 206/365 |
| 2006/0096877 | A1* | 5/2006 | Khajavi | A61B 50/3001 |
| | | | | 206/363 |
| 2007/0119740 | A1* | 5/2007 | Clegg | A61M 5/008 |
| | | | | 206/366 |
| 2012/0037526 | A1* | 2/2012 | Mulone | A61M 5/002 |
| | | | | 206/366 |
| 2013/0306507 | A1* | 11/2013 | Sichau | A61B 50/39 |
| | | | | 206/366 |
| 2015/0021288 | A1* | 1/2015 | Eckhoff | A61J 1/1406 |
| | | | | 215/6 |
| 2015/0108021 | A1* | 4/2015 | Erickson | A61M 5/3205 |
| | | | | 206/366 |
| 2015/0164590 | A1* | 6/2015 | Sakihama | A61M 5/3205 |
| | | | | 206/366 |
| 2015/0374440 | A1* | 12/2015 | Hwang | A61M 5/002 |
| | | | | 220/560.01 |

\* cited by examiner

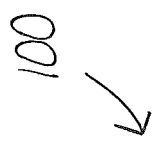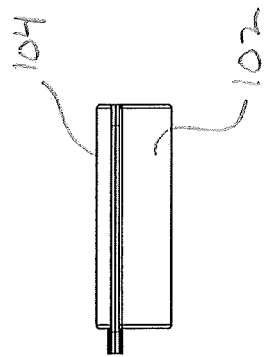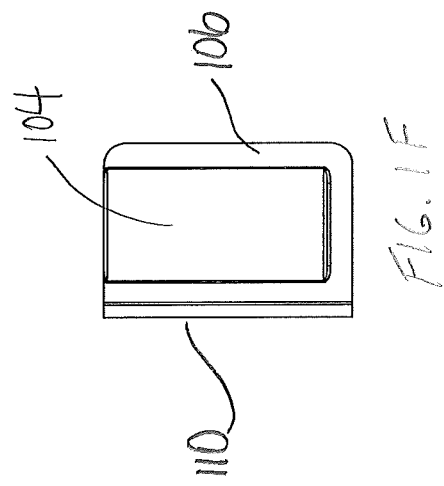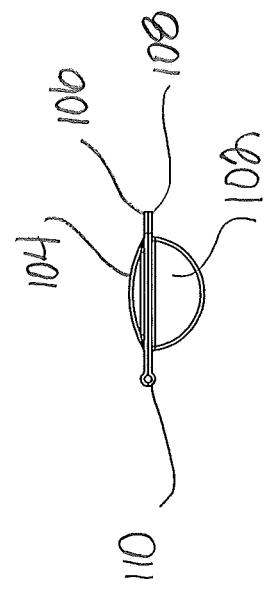

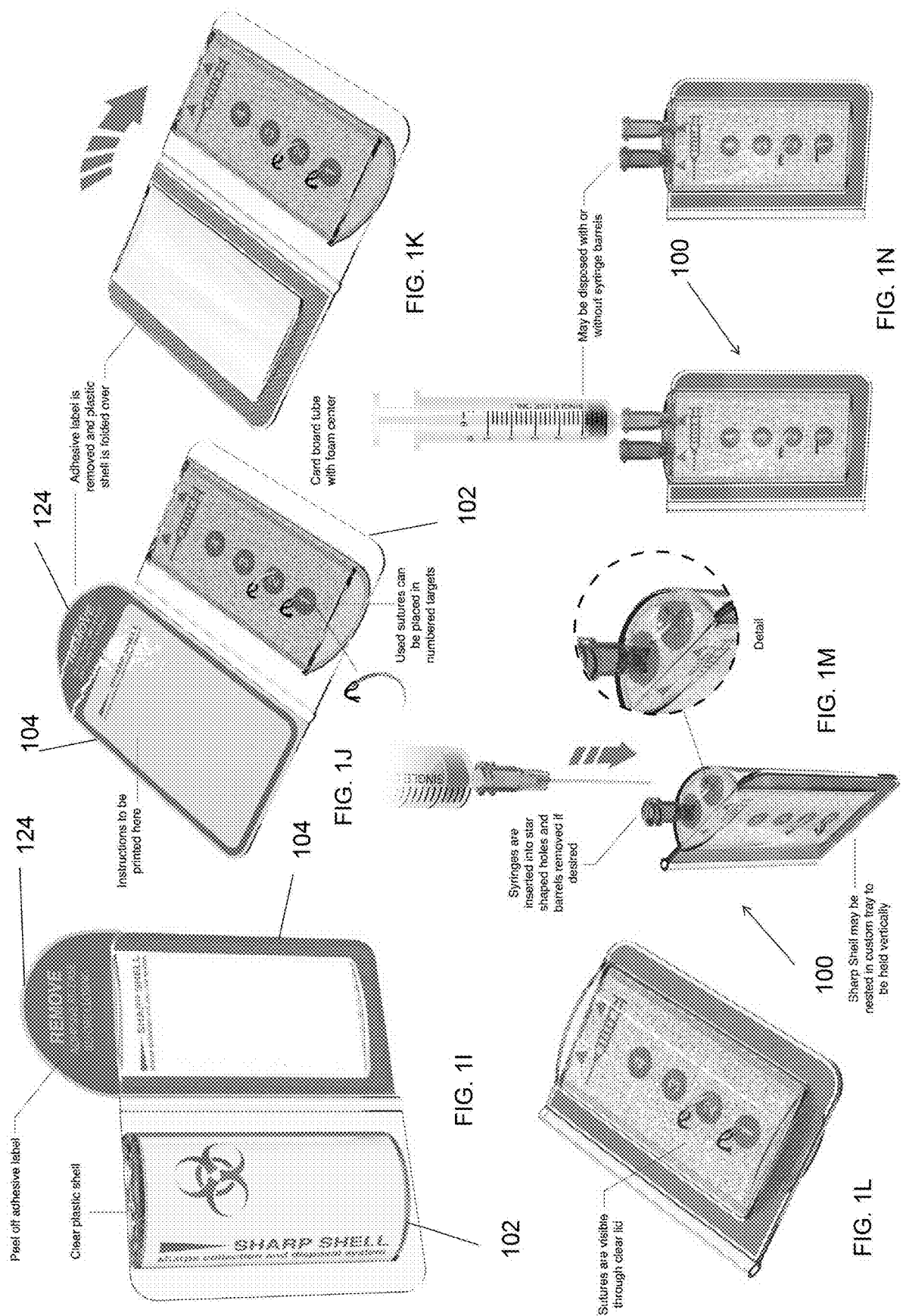

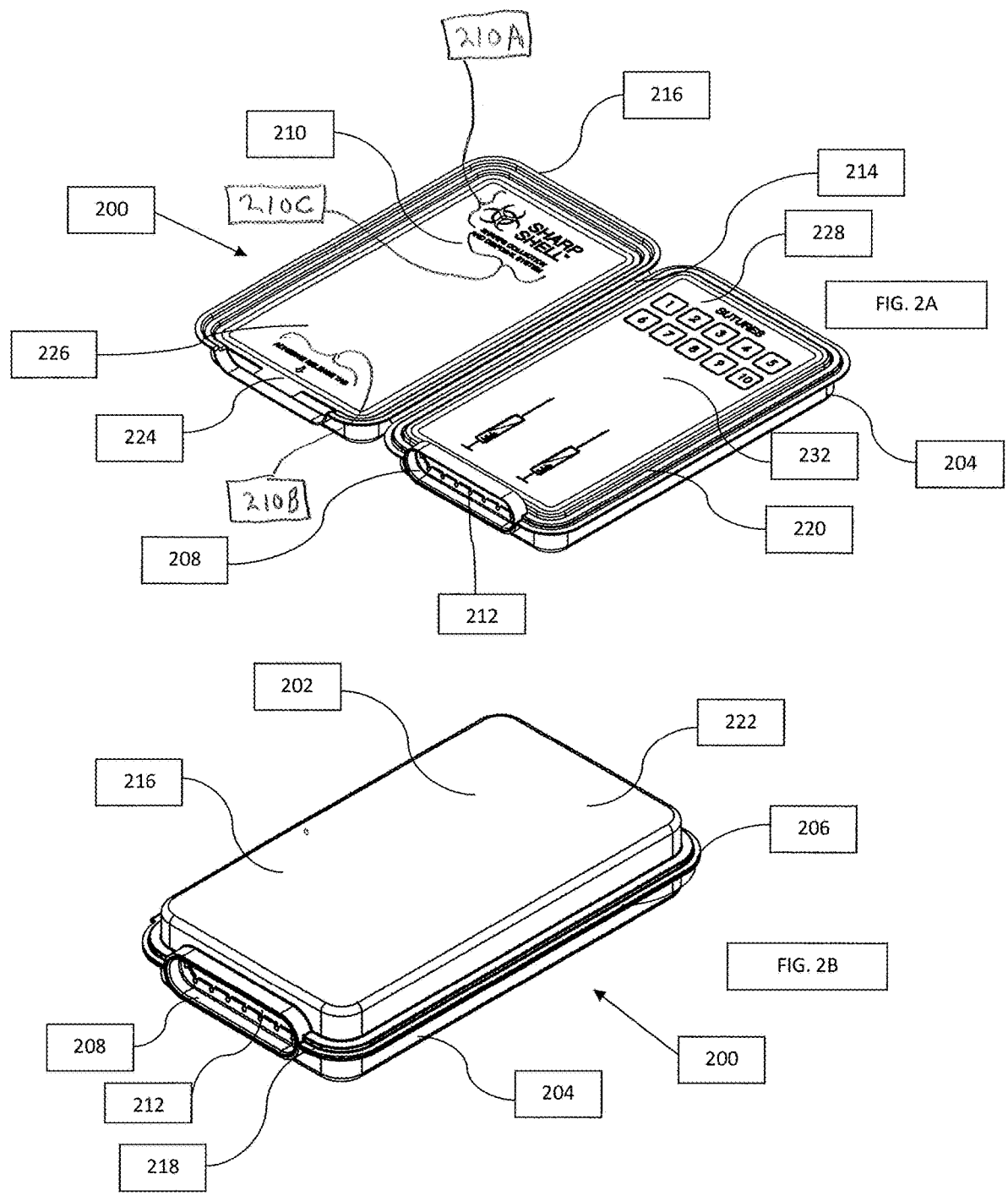

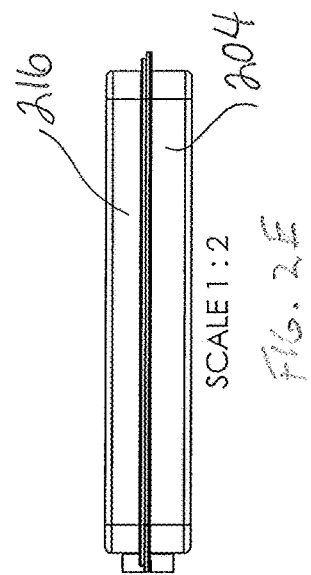
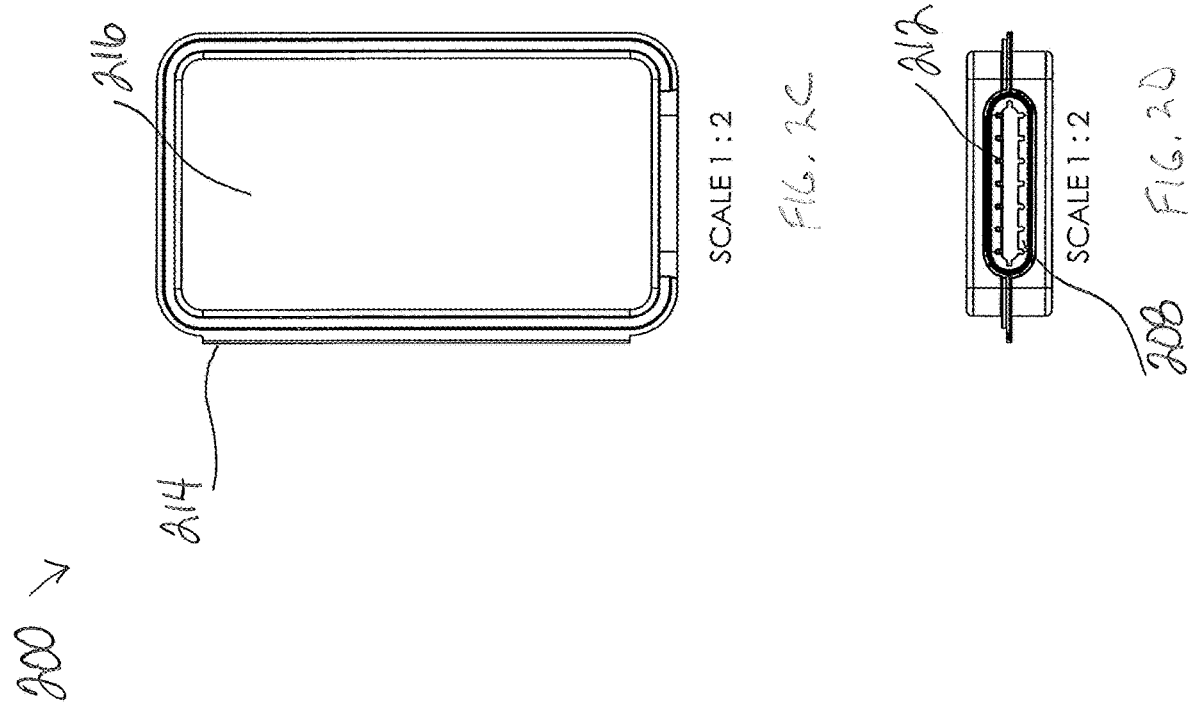

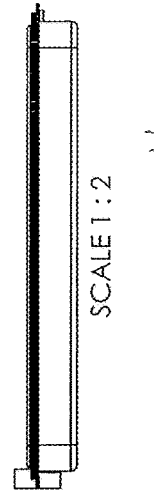
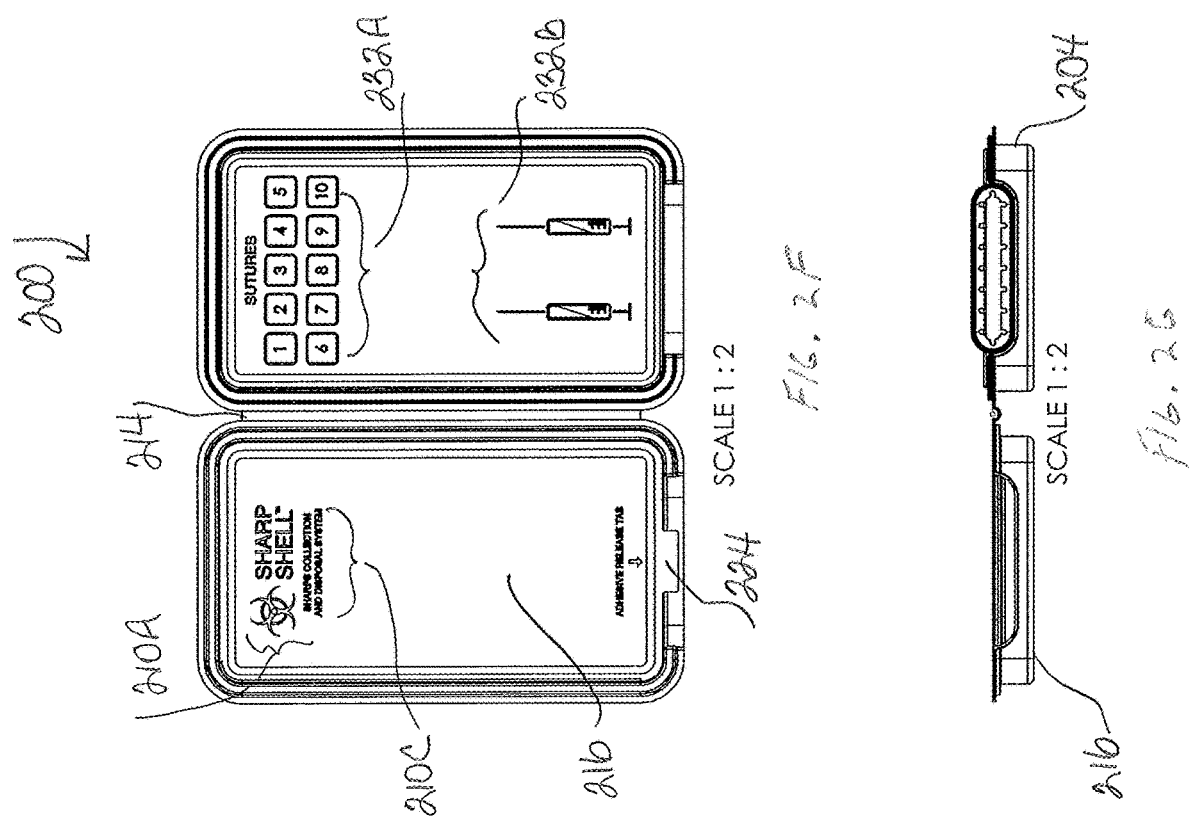

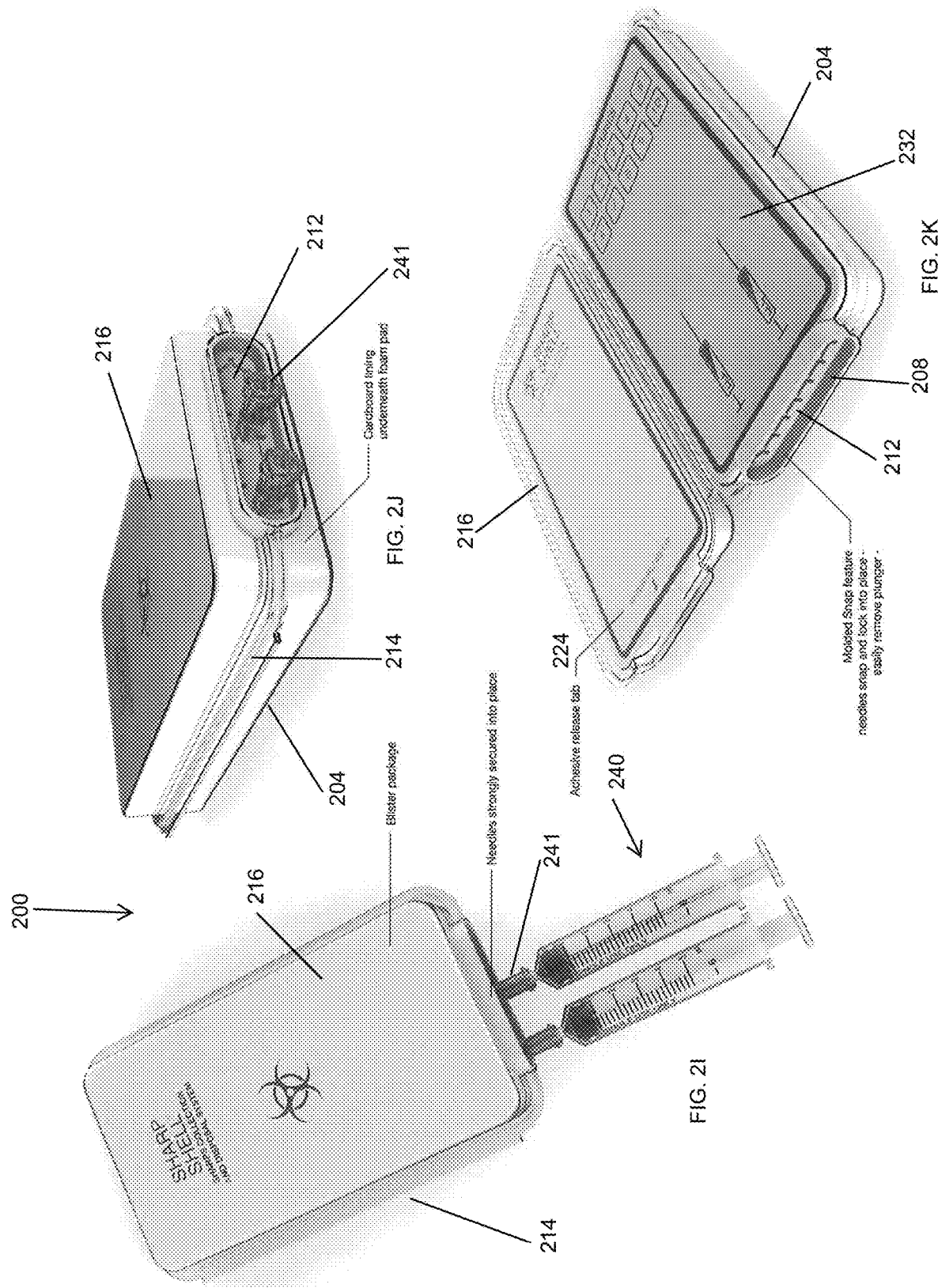

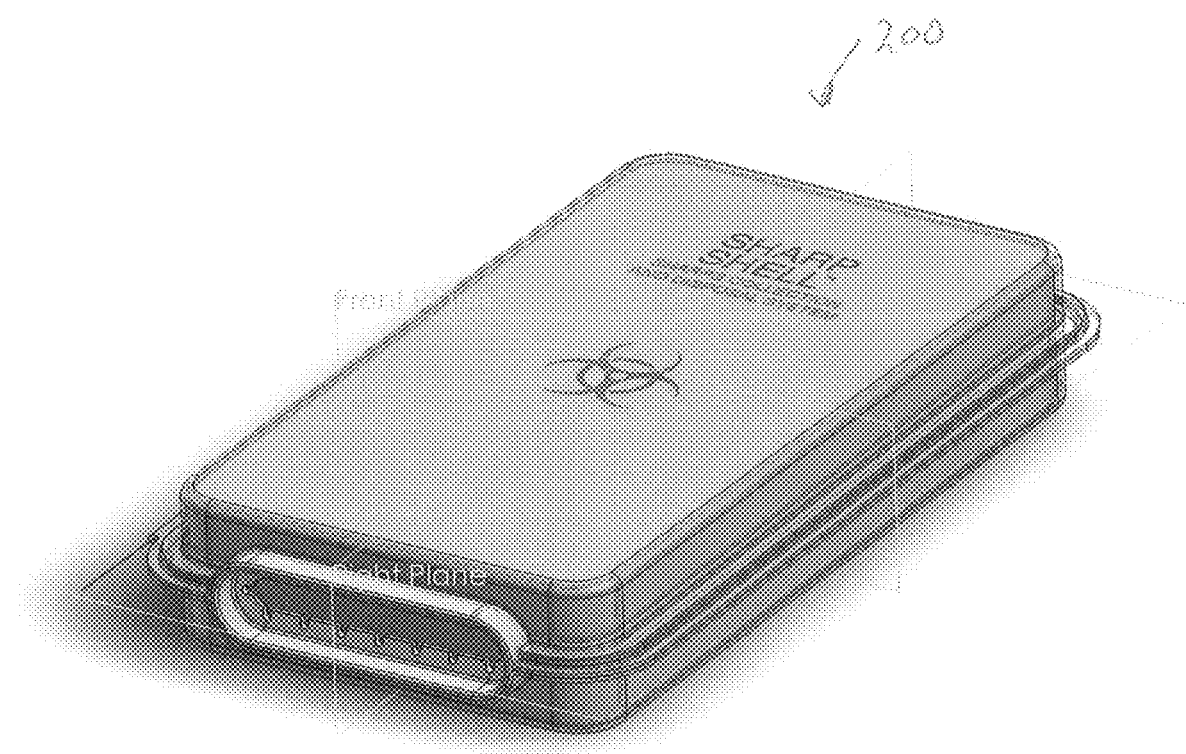

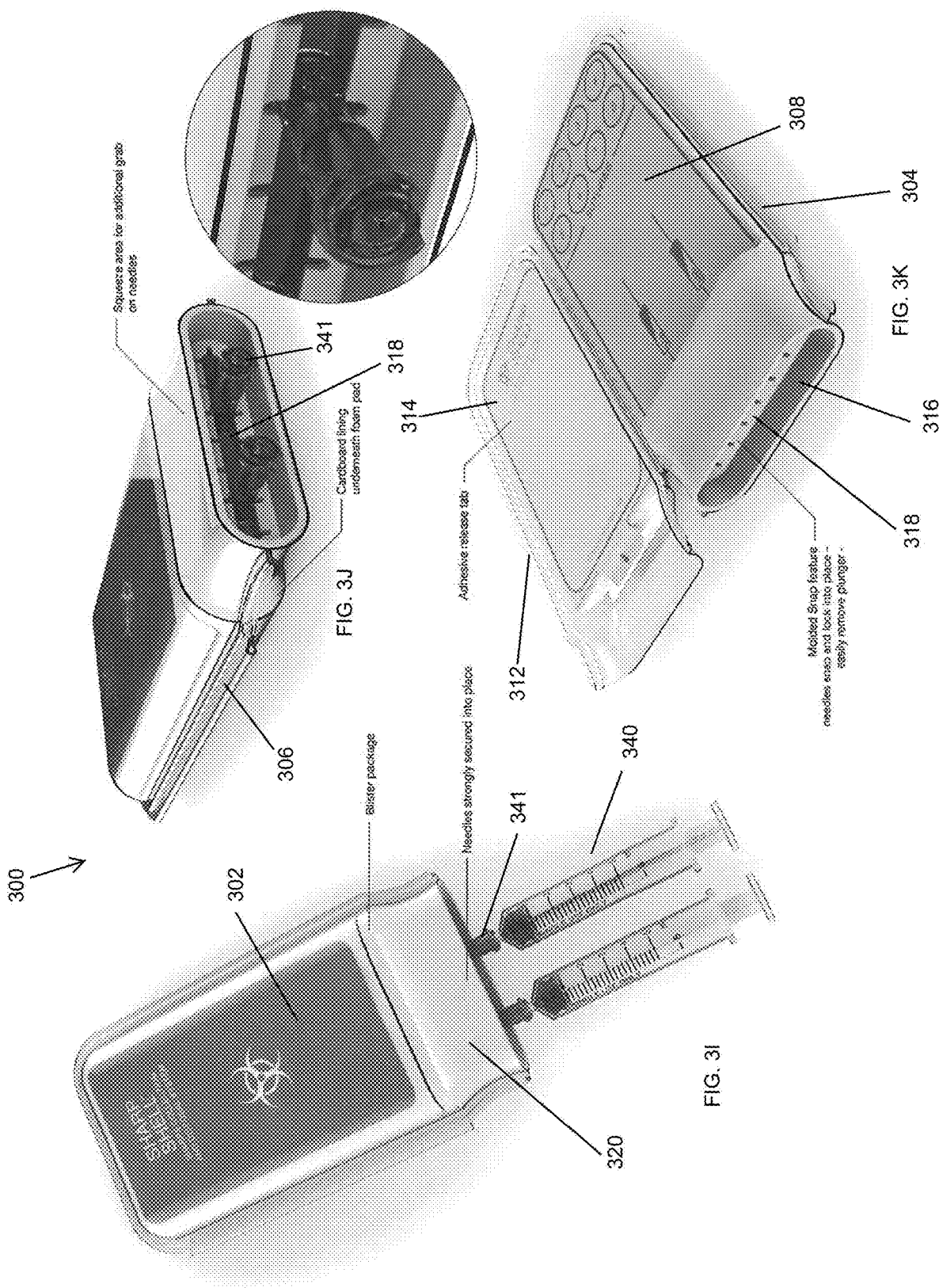

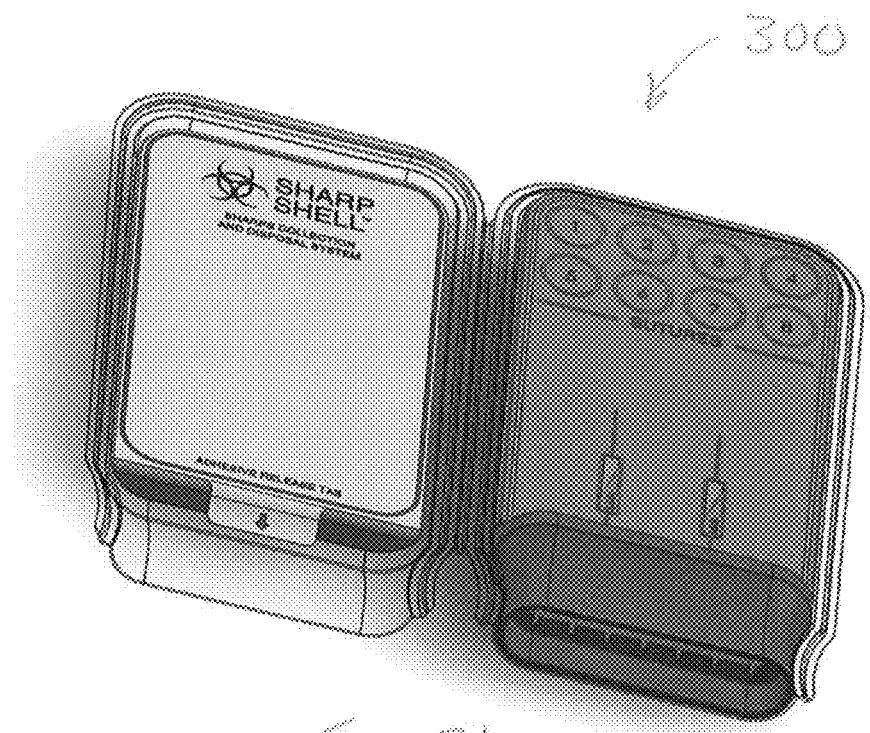

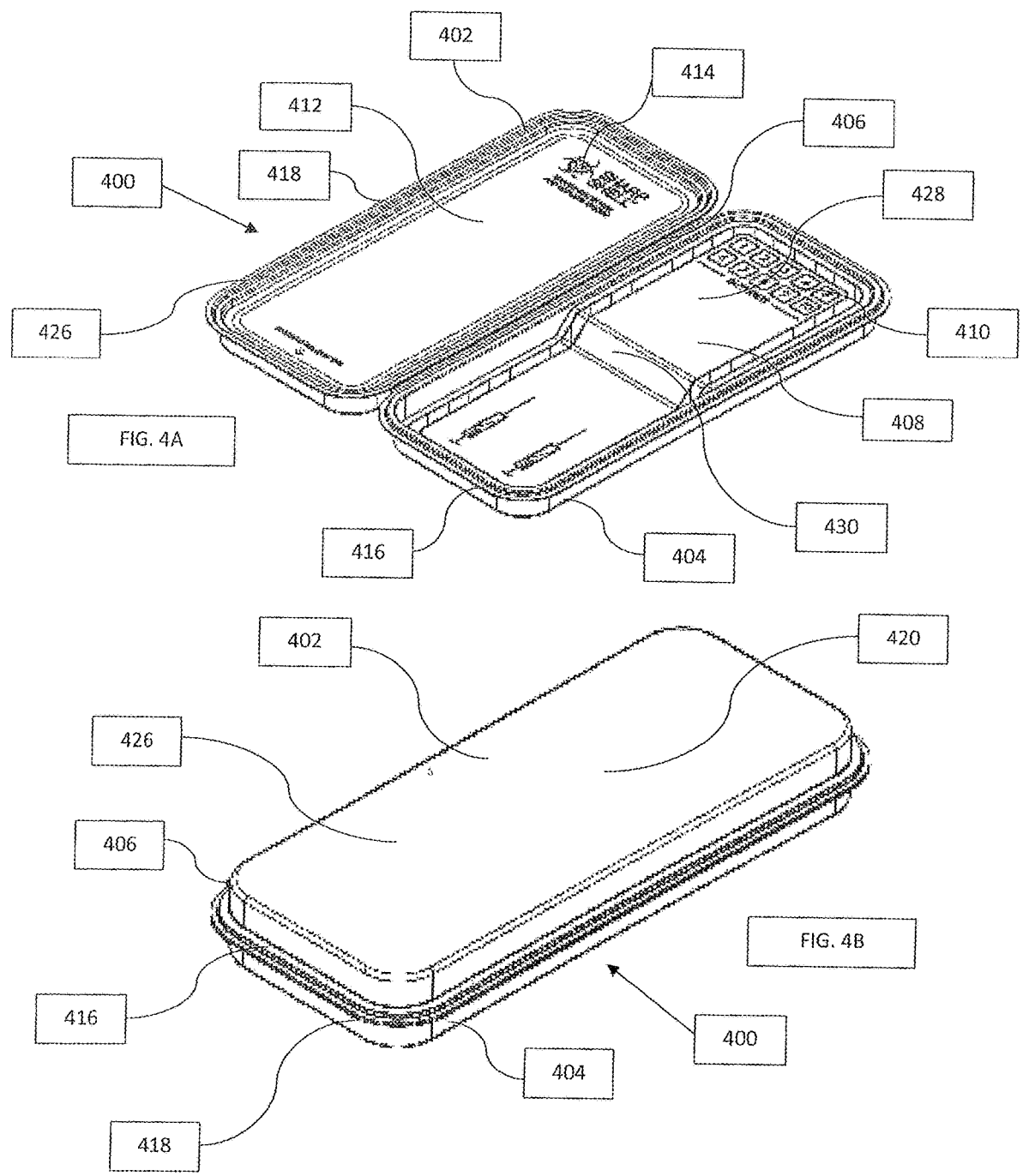

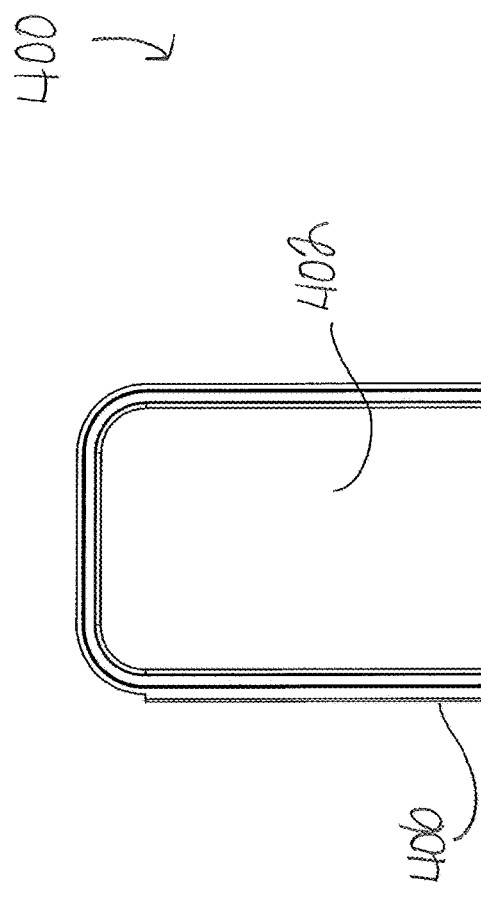
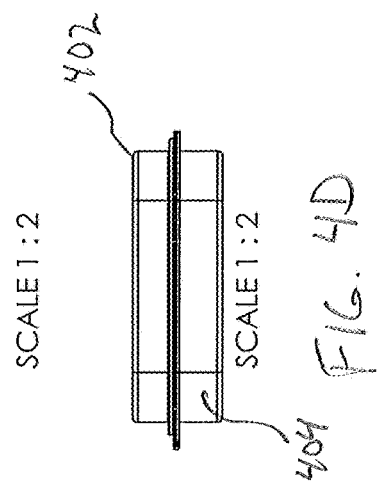

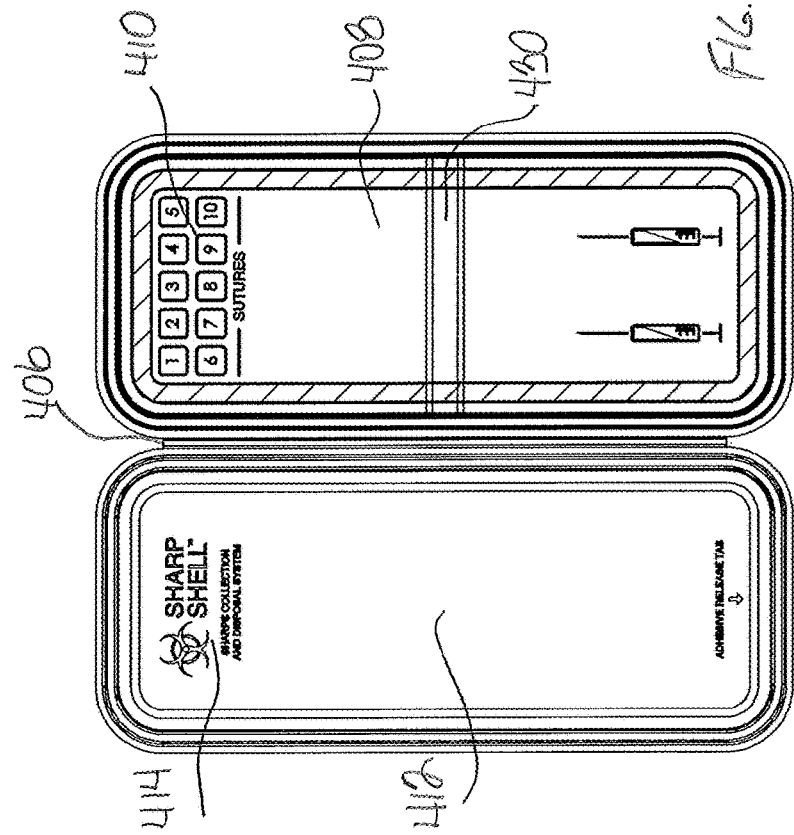
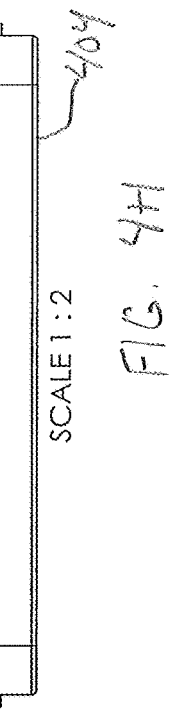
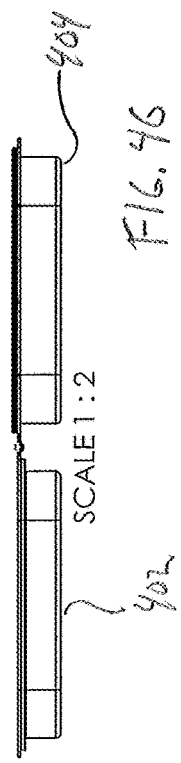

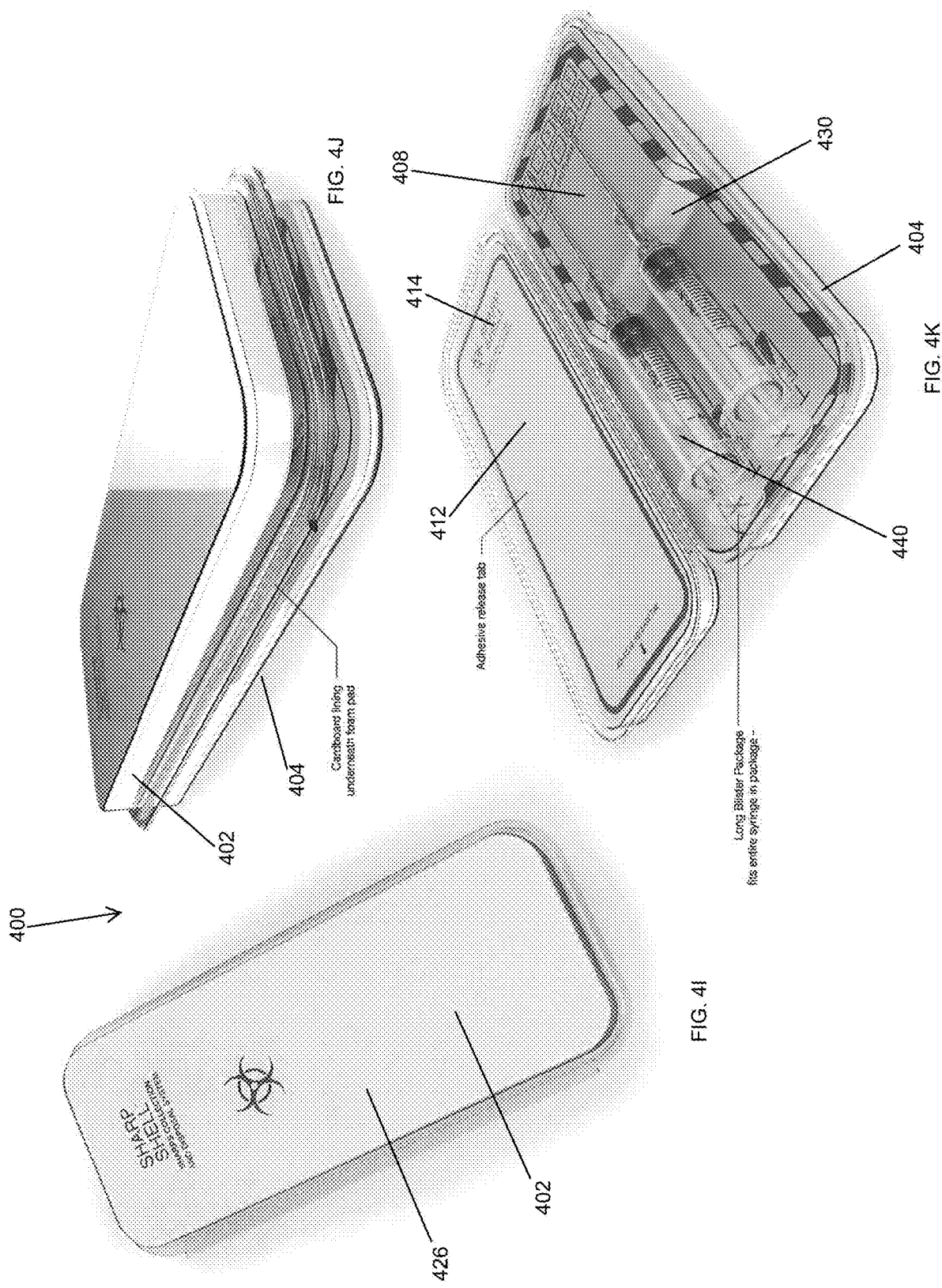

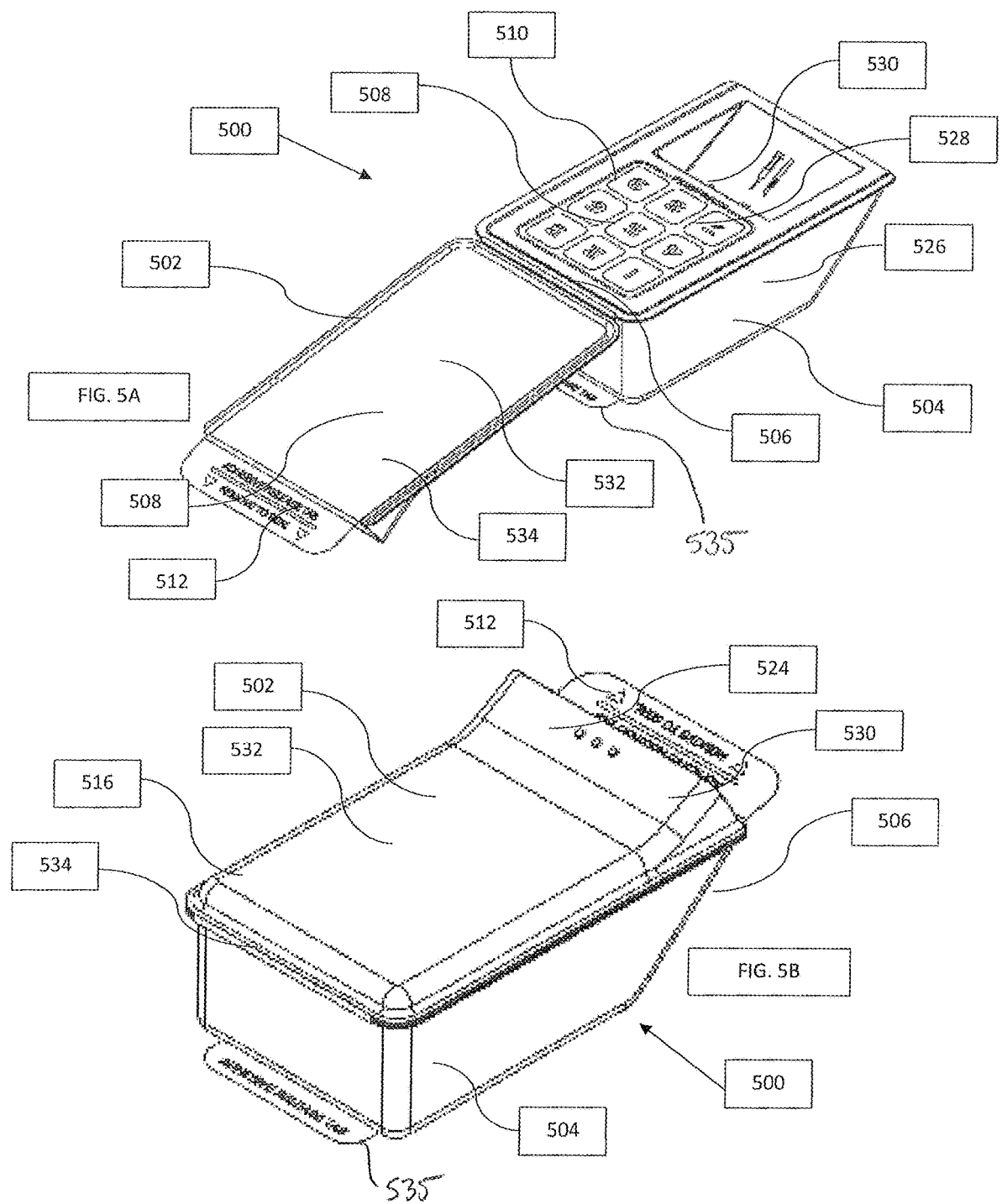

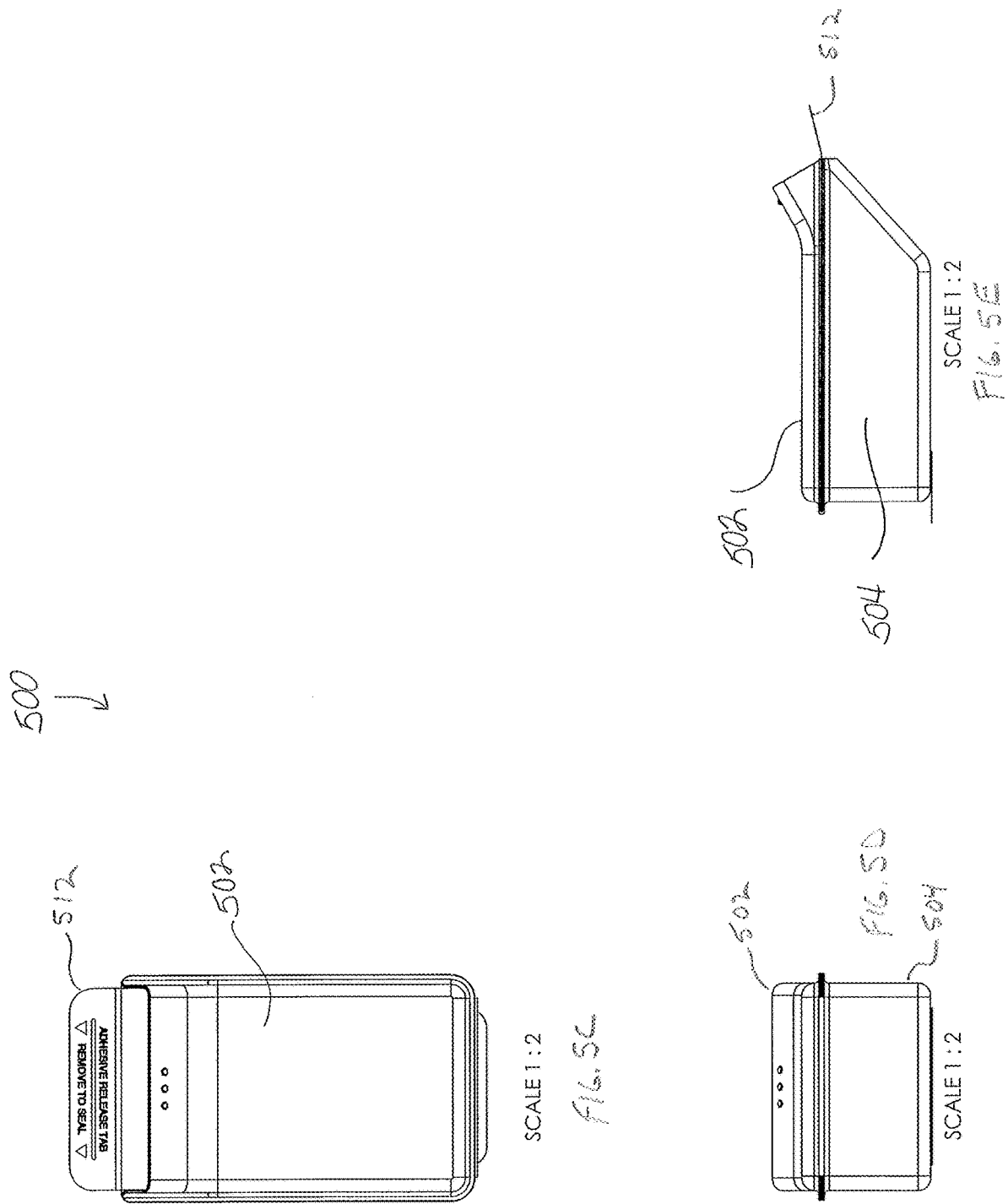

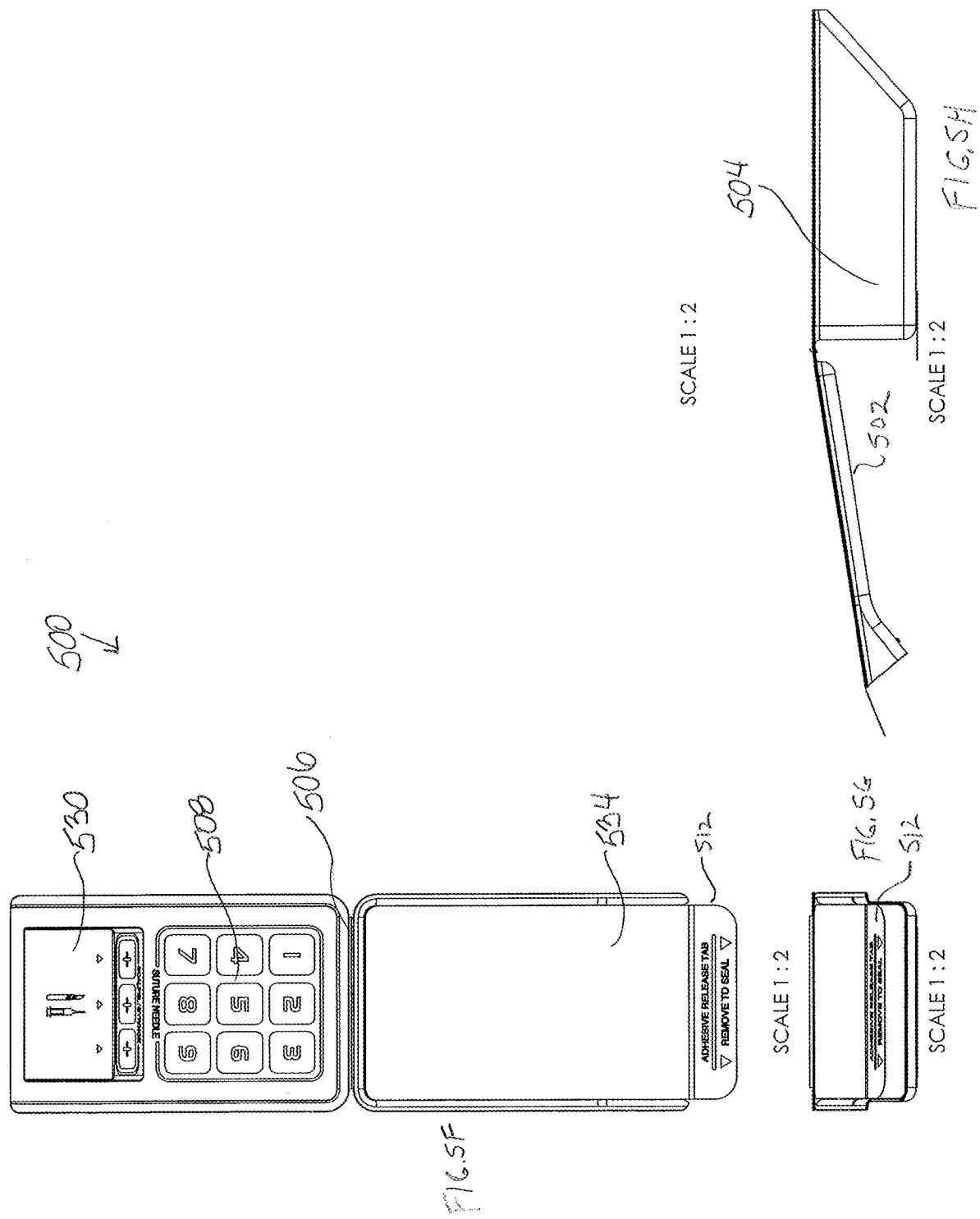

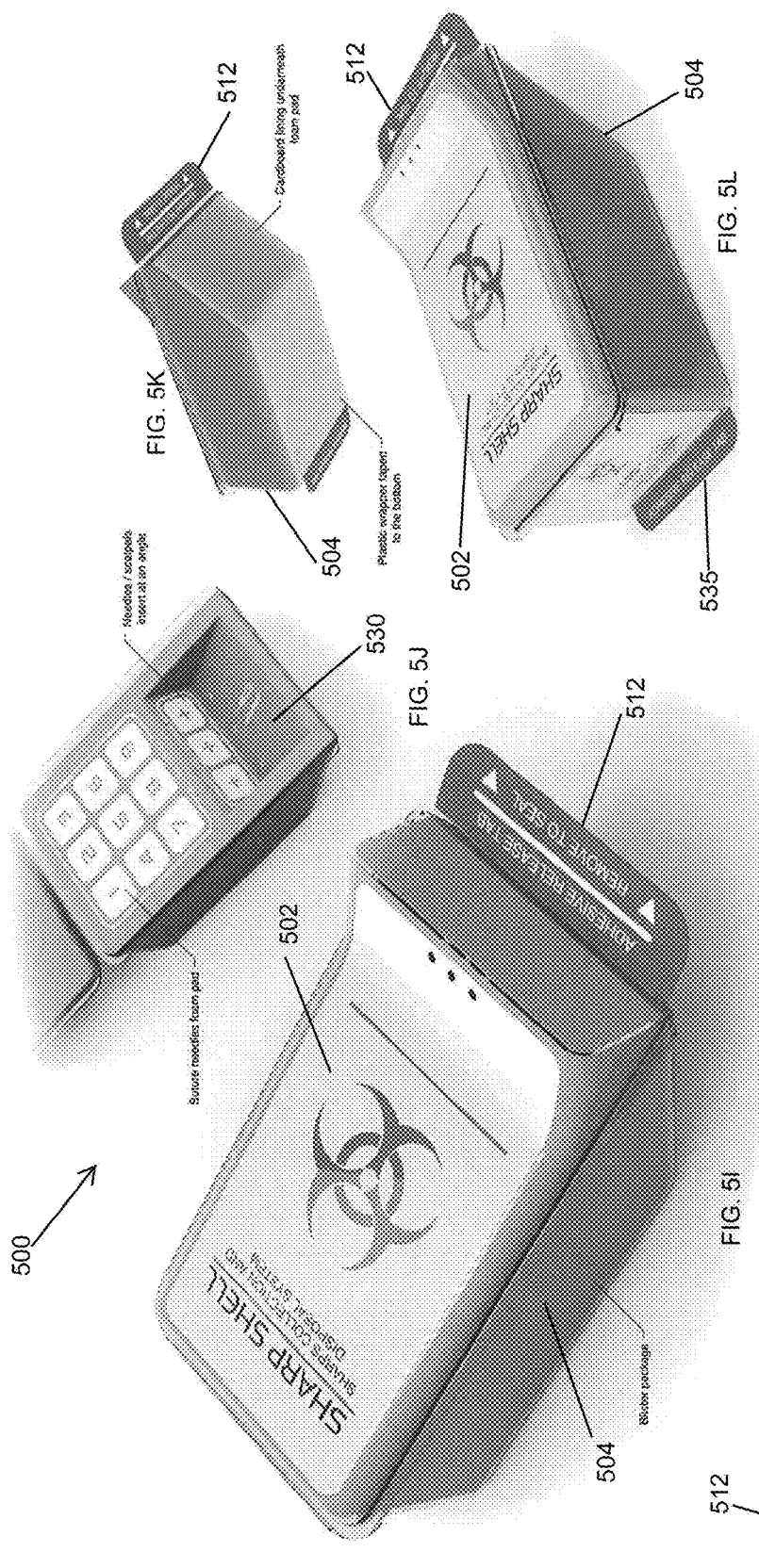
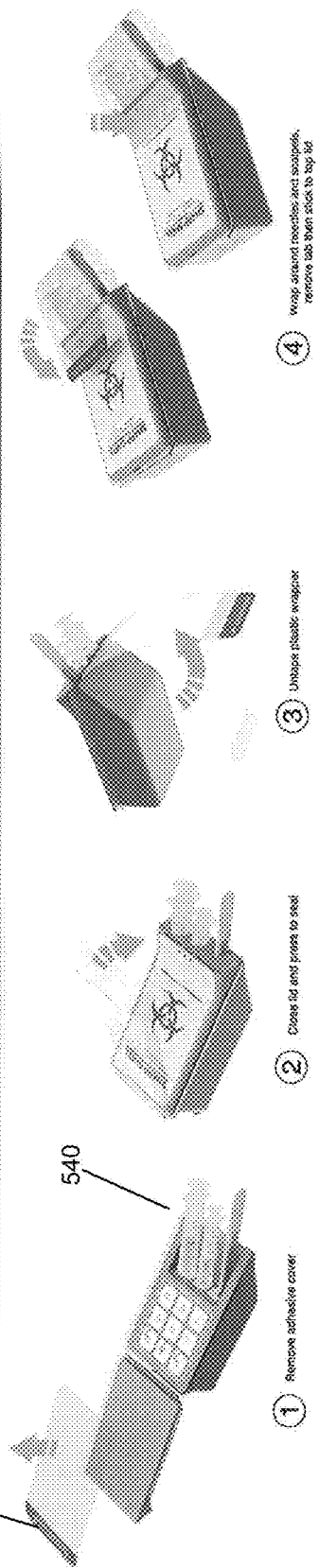

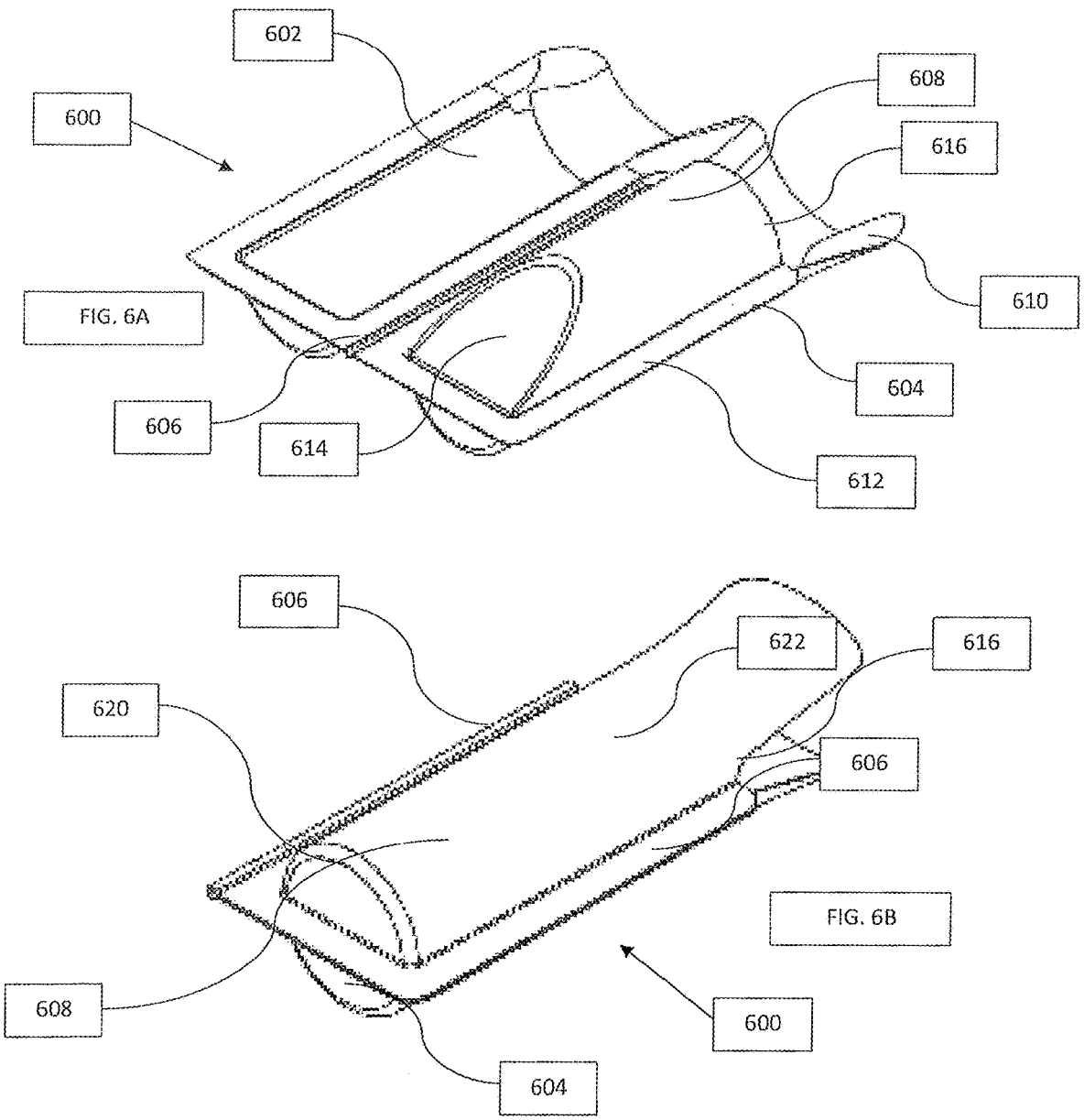

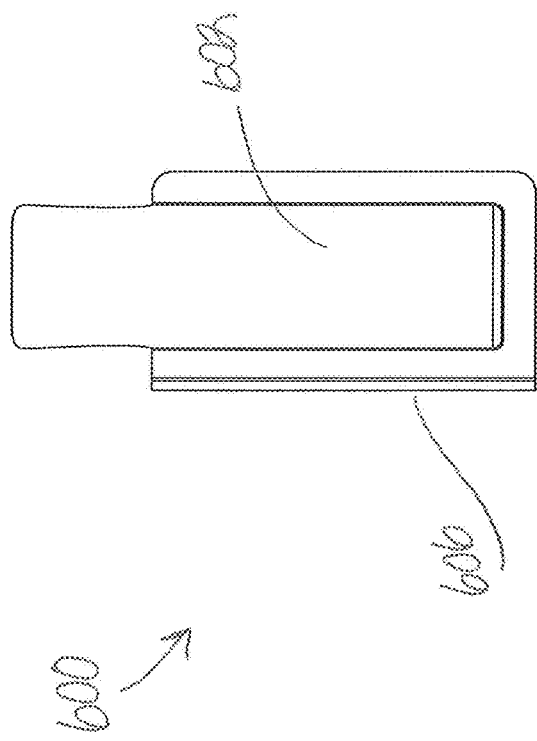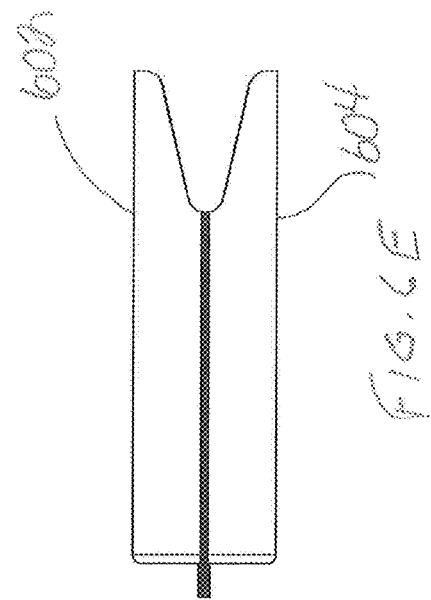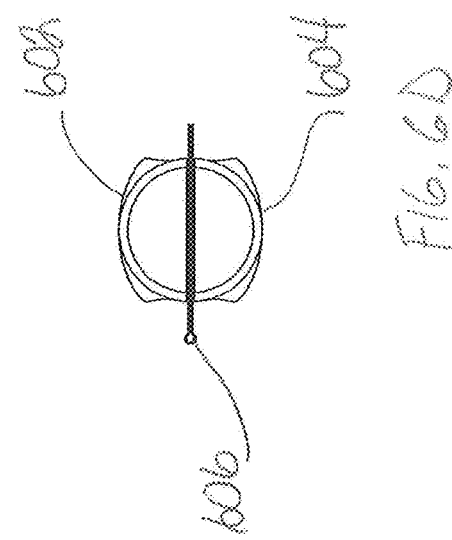

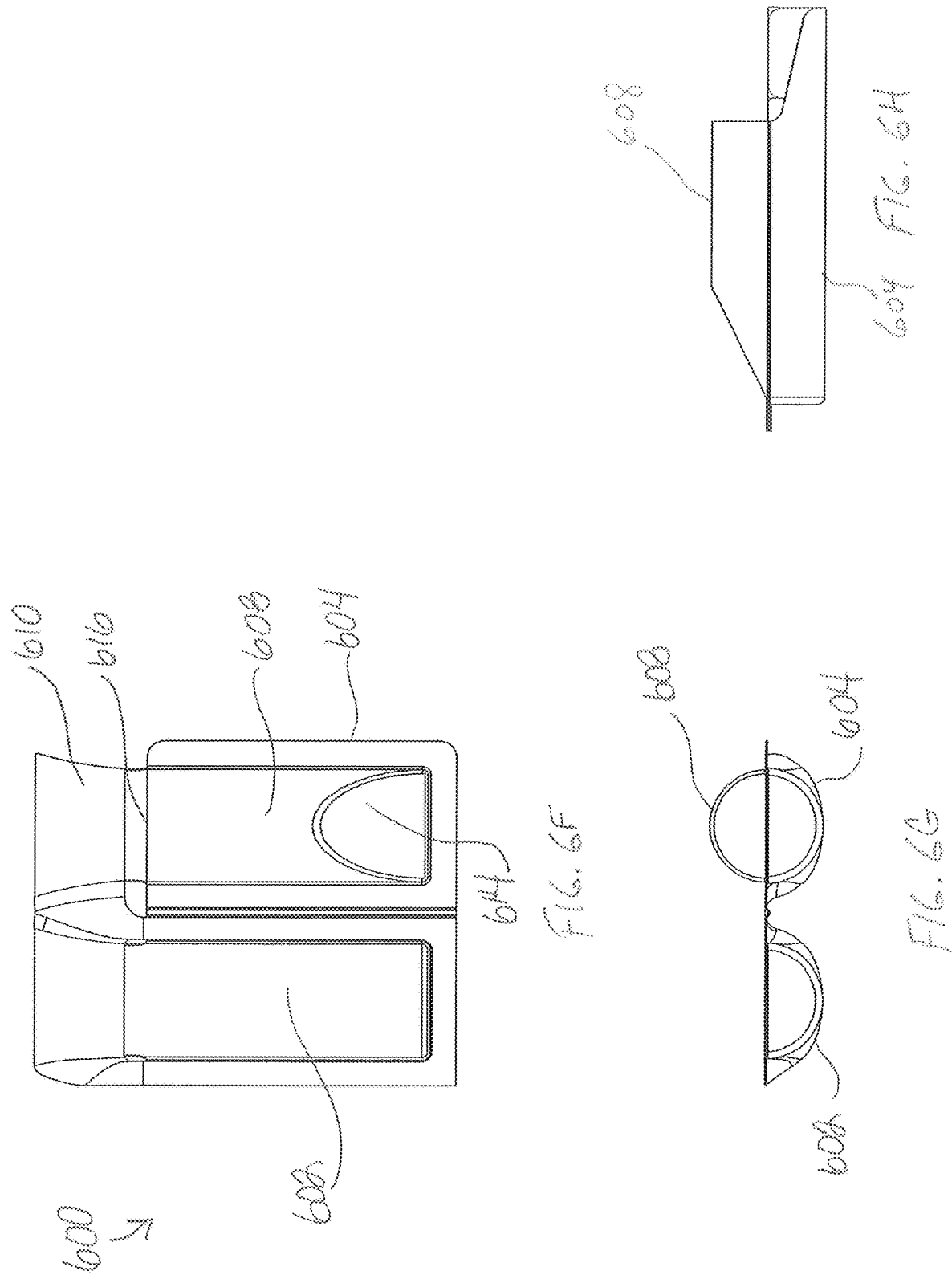

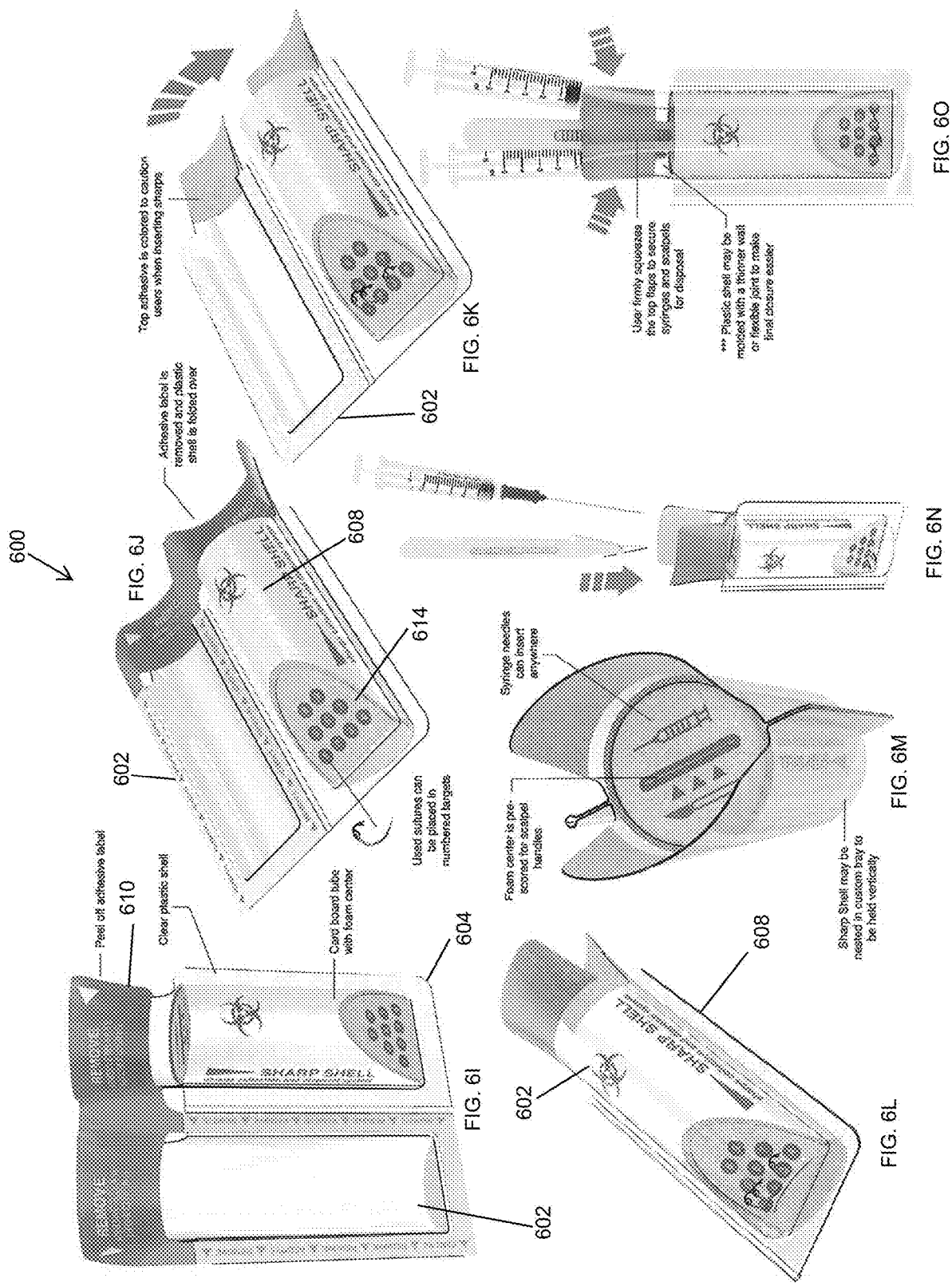

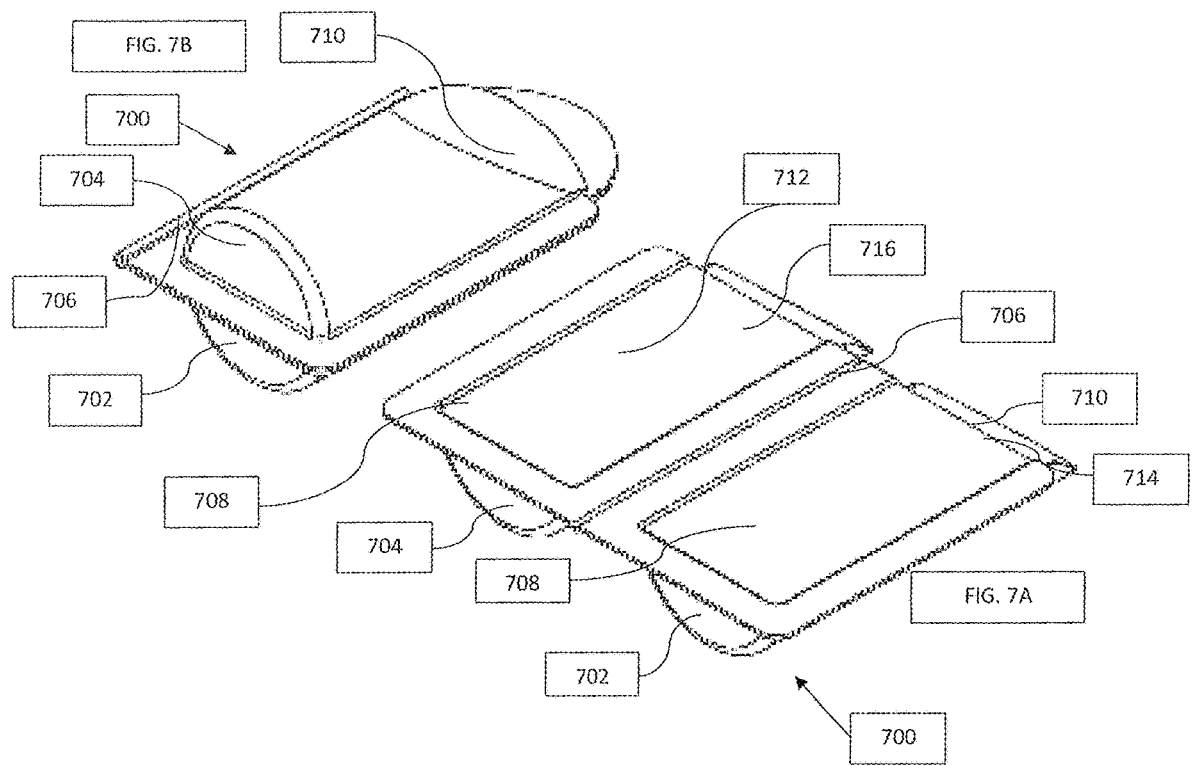

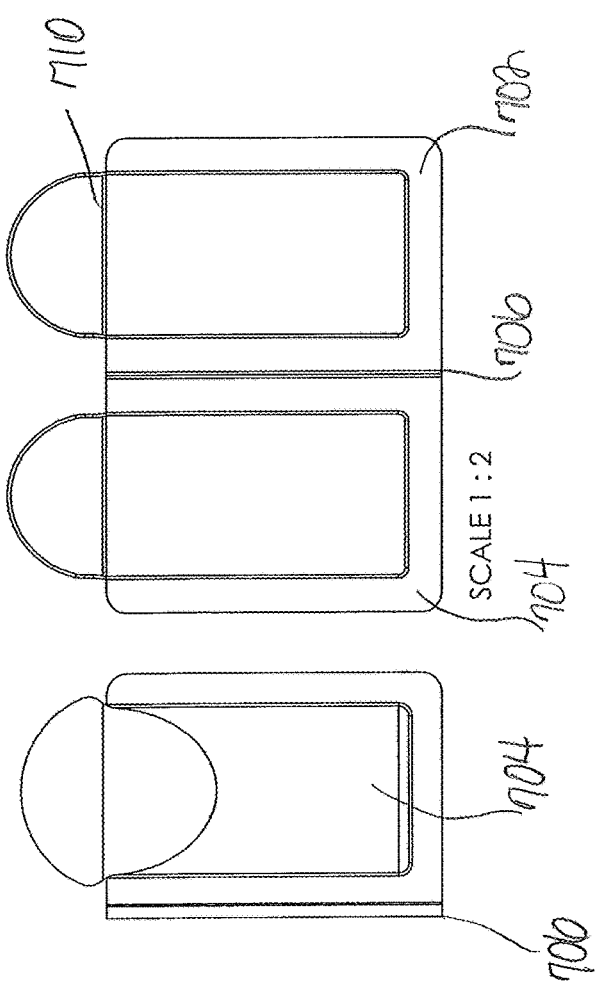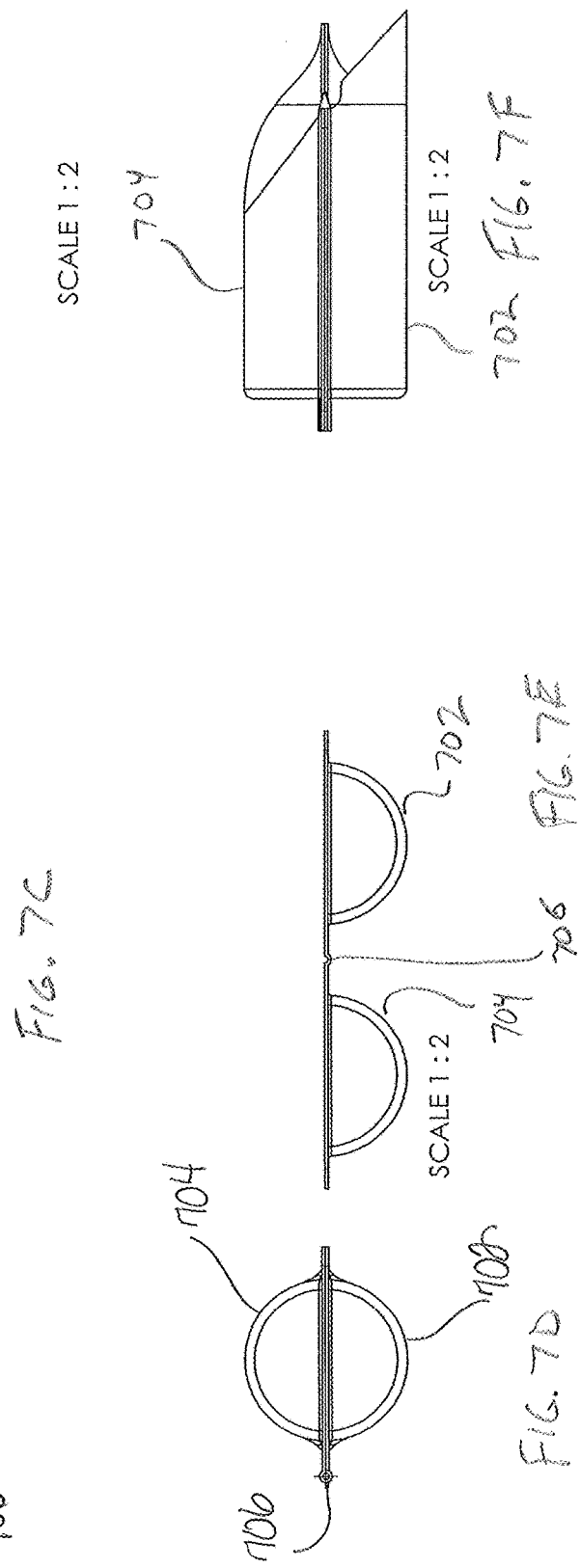

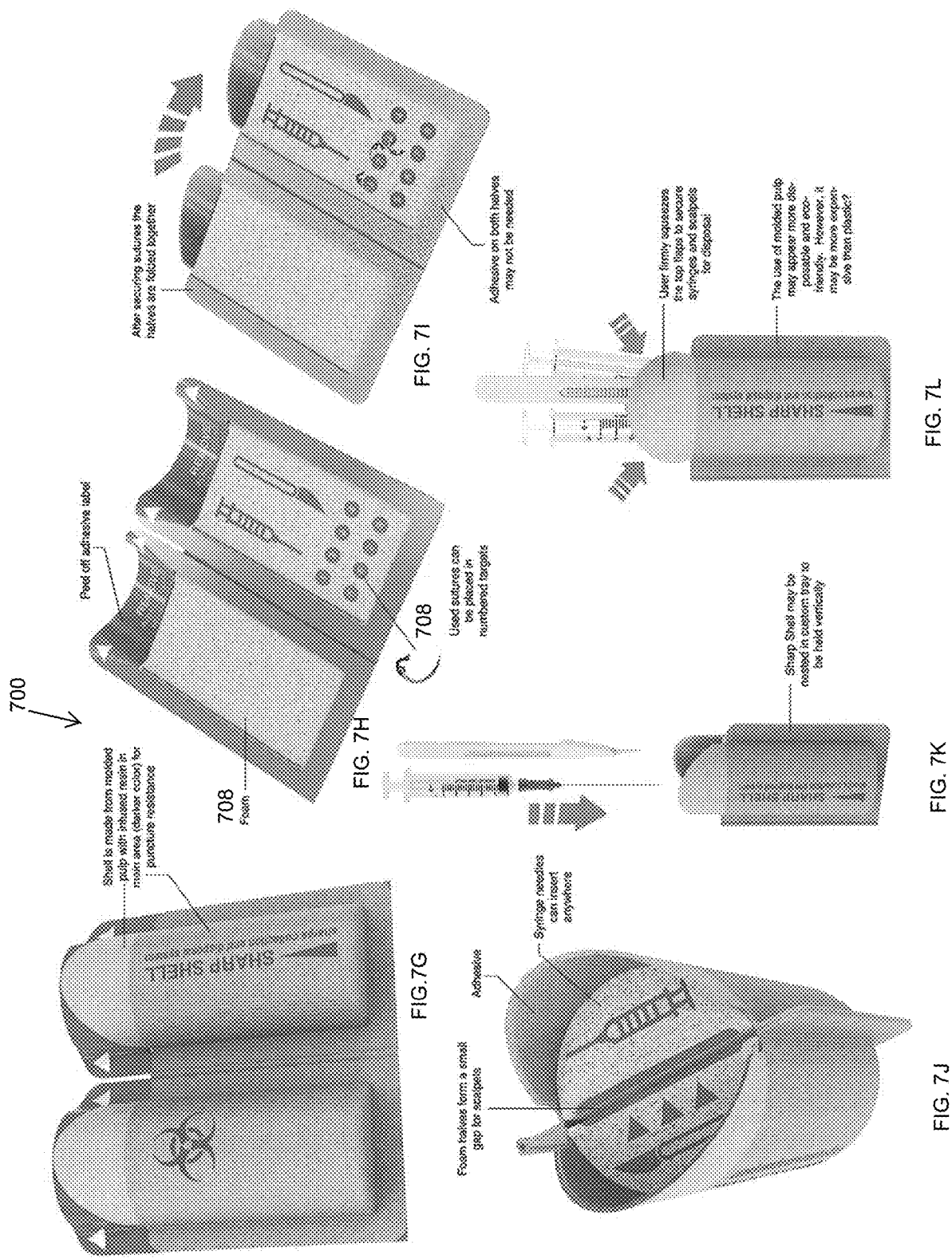

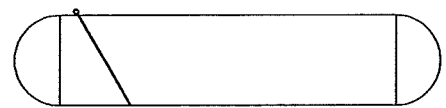
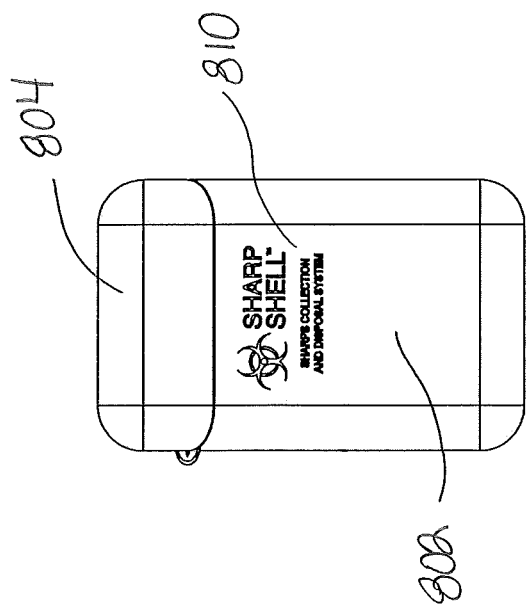
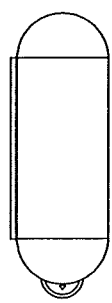

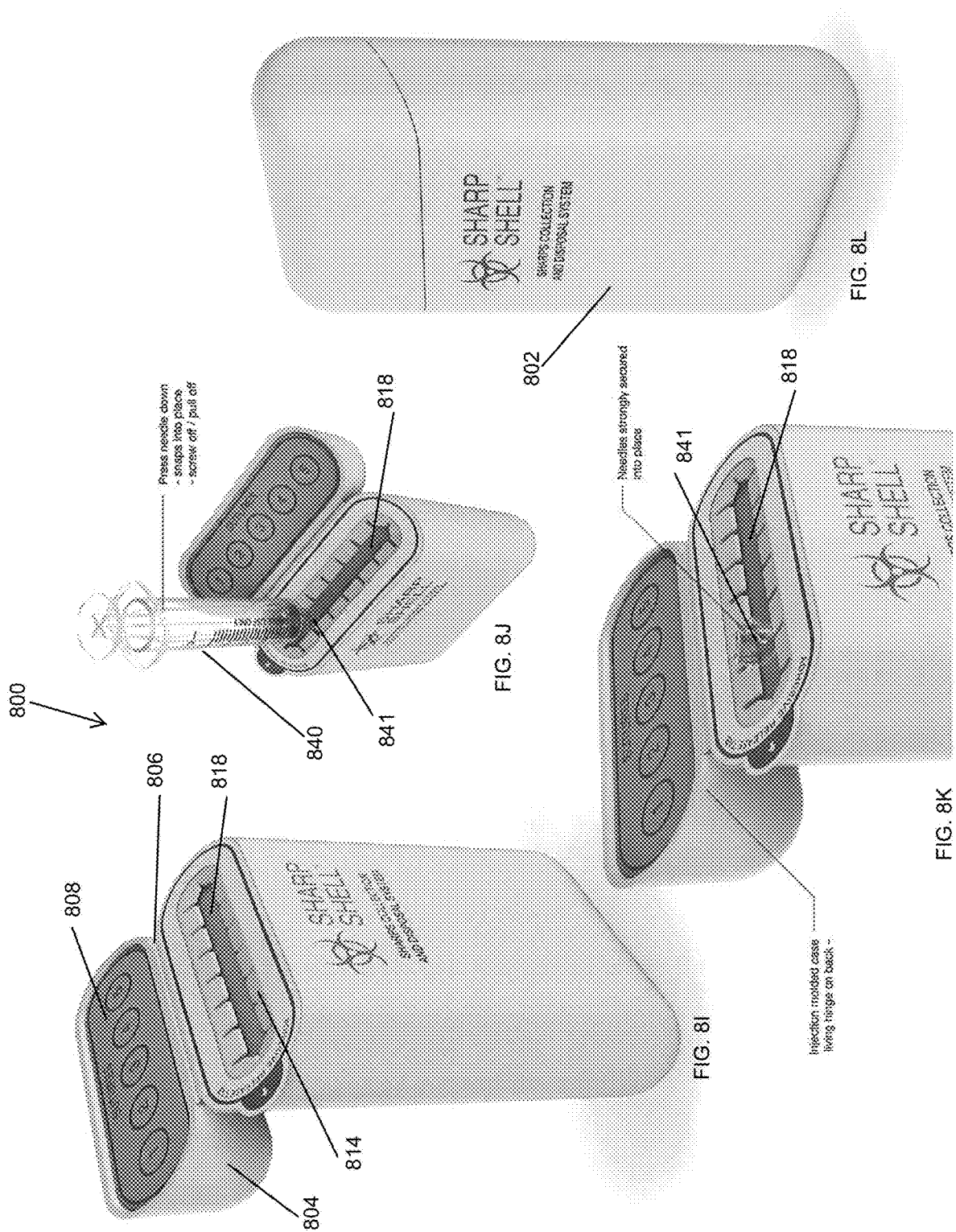

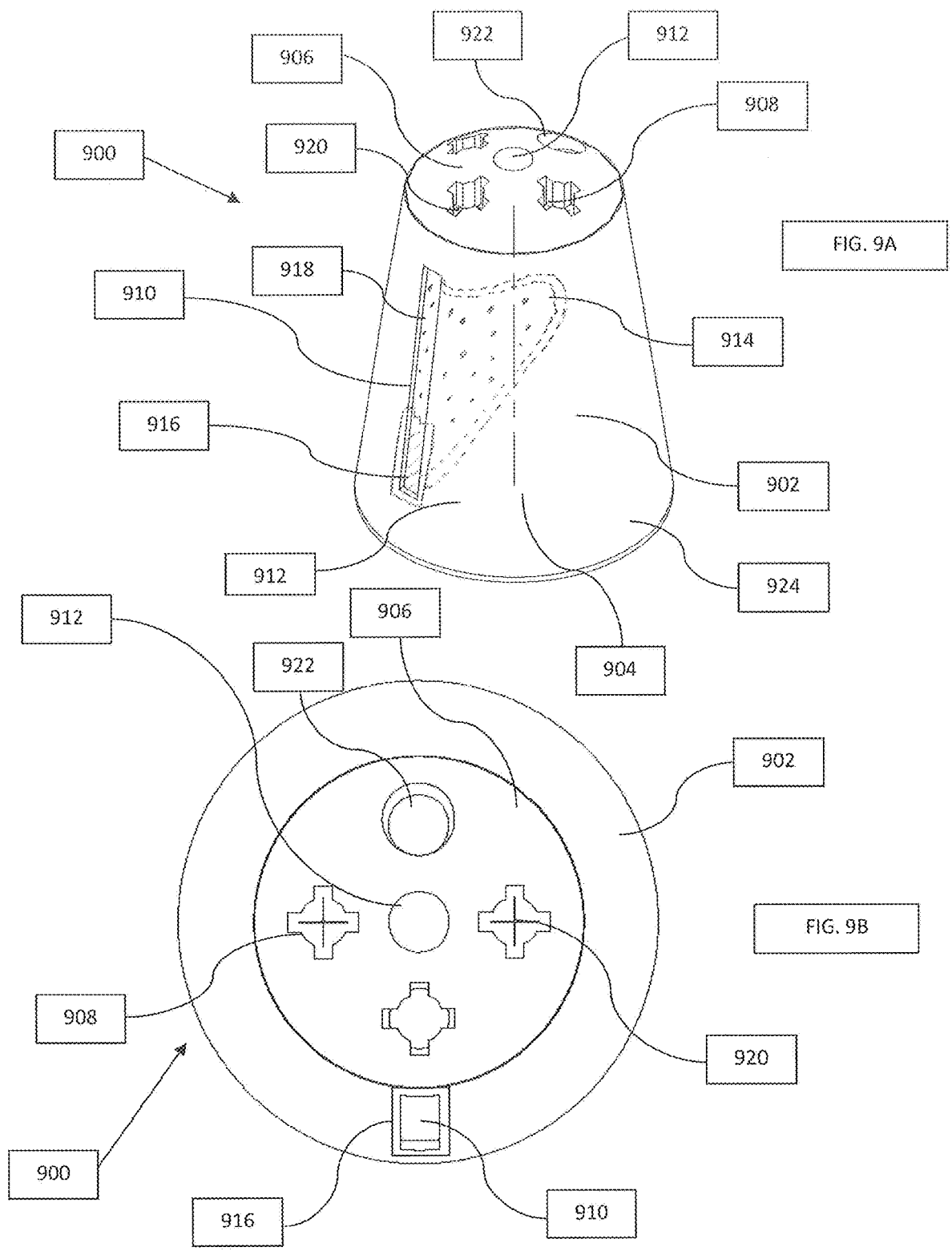

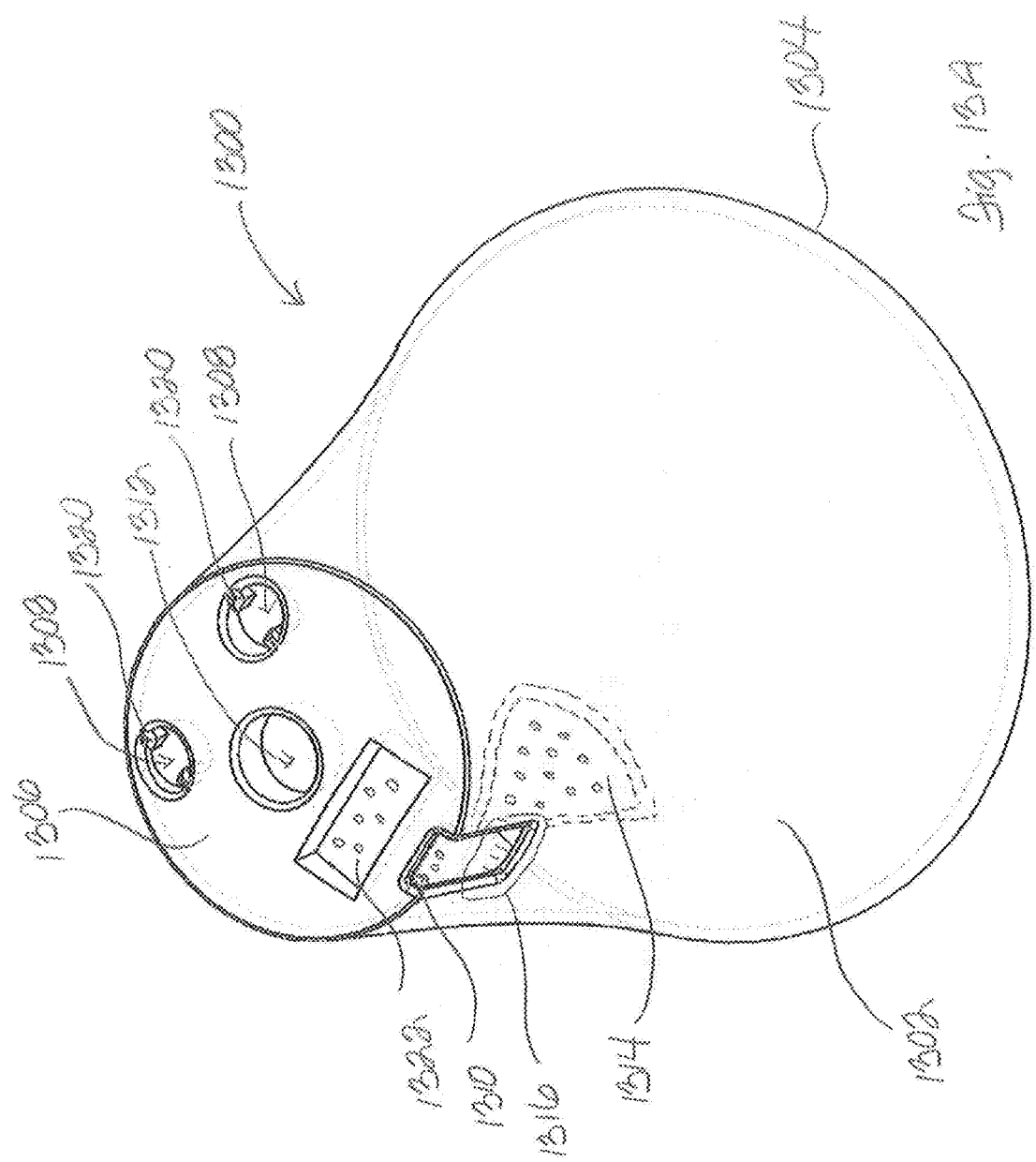

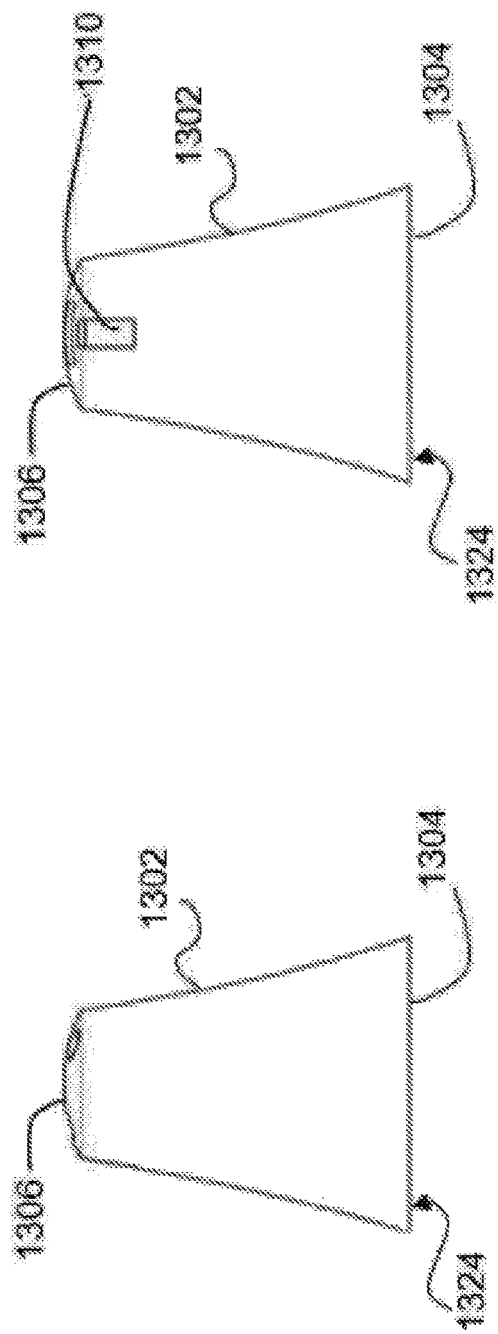
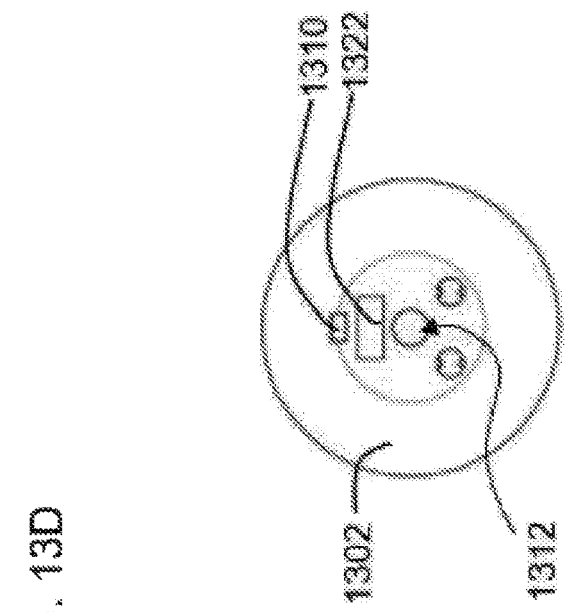
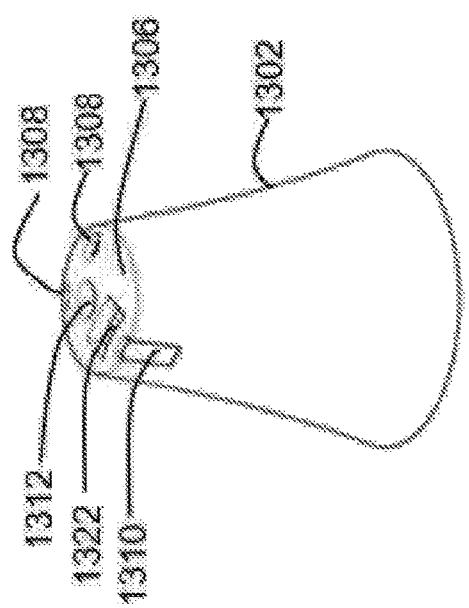
FIG. 13B
FIG. 13C
FIG. 13D
FIG. 13E

METHOD AND APPARATUS FOR SHARPS PROTECTION

RELATED APPLICATIONS

This application claims the priority benefit of U.S. Provisional Application Ser. No. 62/183,967, filed Jun. 24, 2015, which is hereby incorporated in its entirety herein by reference.

FIELD

This invention relates to devices and methods to protect individuals from infectious disease spread due to cuts and puncture wounds made by sharp, contaminated objects. More particularly, the invention relates to a protective container for safely sequestering and disposing of used medical sharps.

BACKGROUND

Pathogenic microorganisms may be present in human blood, body fluids or other infected materials and can cause infection and disease in persons who are percutaneously, or mucocutaneously, exposed. These pathogens include, but are not limited to, hepatitis B virus (HBV), hepatitis C virus (HCV) and human immunodeficiency virus (HIV). In this context, contaminated blood, body fluids or other infected materials may mean the presence or reasonably anticipated presence of pathogenic microorganisms on the surface or in a device.

A medical sharp is an object that can penetrate the skin and includes devices such as, but not limited to, needles, scalpels, tubes, wires, and other medical procedure objects, devices or instruments. Accidental injury or puncture with contaminated, sharp needles or surgical instruments, referred to as medical sharps or sharps, remains a significant risk to healthcare workers. All healthcare workers, such as physicians, nurses, paramedics, emergency medical technicians, ambulance staff, airmedics, airmedic staff technicians, janitorial staff, office staff, and even patients and their families are potentially at risk from this dangerous situation.

Typically, injuries resultant from accidental needle and scalpel sticks occur after the instruments have been used. As a result, healthcare workers are subject to serious diseases, including but not limited to hepatitis B virus (HBV), hepatitis C virus (HCV) and human immunodeficiency virus (HIV).

Most often, needle and scalpel punctures occur during the handling of used sharp instrumentation prior to permanent disposal. Healthcare workers can accidentally stick themselves or others in the vicinity while carrying contaminated instruments to a centrally located disposal container for used sharps. Often, needles dangerously protrude from the designated container, often located on a peripheral wall of a given room and often located behind furniture, fixtures, and medical equipment. This increases the risk of puncture to the healthcare worker placing the sharp in the container, or emptying the used sharps container.

The true cost of the problem is difficult to measure. For every "needlestick" exposure, the health care worker is subjected to batteries of tests that are repeated 3 to 4 times over the following year. If the risk is determined to be substantial, in terms of exposure to known or likely HIV, Hepatitis, or other pathogens, there may also be medication costs involved. There are side effects to medications administered for suspected disease transmission and the costs, both societal and monetary, are significant for such treatments. If a disease is actually transmitted by the event, the costs, both personal and financial, are staggering, and the event can prove to be career ending as well as adversely affecting the family and social life of the healthcare worker. Disease transmission, in the worst scenario, can be life ending for the exposed healthcare worker. Bearers of these costs, both tangible and intangible, include health care organizations, their insurers, governmental agencies, the health care workers and their families, and society as a whole.

Current solutions in the prior art include needle guards and covers, retractable needles, scalpel protectors and needleless connecting systems for intravenous solutions.

Although needle guards and covers, needles and needleless systems address part of the solution to the problem, they do not offer a universal solution that will manage the risks posed by other types of medical sharps, including scalpel blades, trocars, and the like.

A typical sharps collector and disposal device is a mailbox-style container with or without a pull-down opening allowing access to the container. The user pulls the lid open, deposits the used sharp, and releases lid, which swings shut, much like mailing a letter. Mailbox-style containers without the pull-down opening have a tortuous path that the sharp must traverse to enter the container. The mailbox-style containers can be found in a variety of sizes and uses, such as in-hospital room containers, multi-purpose containers, mail-away containers, large volume and pharmacy containers, specialized containers, transportable containers, and the like.

A typical problem with mailbox-style receptacles is that they are frequently overfilled with needles, such that the needles stick out of the container opening. In addition, it may be difficult to put certain types of sharps, such as butterfly needles, needles attached to syringes, suture needles, trocars, cannulae, and the like, into them. An overfilled mailbox-style receptacle may result in healthcare workers becoming cut and infected by an already disposed-of sharp when they try to insert a new sharp into the receptacle and force their hand on the protruding sharp object, or by the new sharp itself. An additional risk of the mailbox-style receptacle includes the user being stuck as the sharp is being placed into the unit due to the difficulty of inserting the sharp into the tortuous pathway opening.

Not only are health care workers themselves at risk because of inadequate or unsafe disposal systems, but there are significant risks to housekeeping personnel within healthcare institutions and even to the public, who may encounter an improperly disposed, contaminated, unprotected, medical sharp device. Areas at risk include in-patient hospitals, outpatient facilities, emergency or ambulatory facilities, patient homes, offices, public restrooms, physician's offices, nursing homes, laboratories, emergency medical facilities, military facilities, helicopters, airplanes, airmedic facilities, employer facilities, hospice care facilities, needle dispensing facilities for heroin addicts and diabetics, and the like. Unprotected contaminated medical sharps are occasionally found in public areas such as public beaches, parks, and children's play areas.

New devices, procedures, systems, and methods are needed for guarding, dispensing, and collecting contaminated sharps to minimize the risk of accidental wounding of healthcare workers and others by infectious, sharp devices. Such devices and procedures are particularly important in any medical setting including in-hospital, pre-hospital, outpatient, military, and the emergency department.

SUMMARY

This invention relates to devices to minimize the risk of injury and infectious disease spread from one individual to another due to injuries or puncture wounds made by sharp, contaminated objects.

The apparatus described herein is termed a Sharpshell although this term is used without limitation or functional constraint throughout only for convenient reference to the apparatus of the present invention. The Sharpshell can comprise a rigid or semi-rigid shell that is puncture resistant to syringe needles, scalpel blades, suture needles and the like, under normally anticipated loading. The Sharpshell can comprise a top, or upper, portion and a bottom, or lower, portion. The top portion can be affixed to the bottom portion by means of a hinge or other connector. The top portion can be closed against the bottom portion to create a closed shell. The closed shell can comprise an internal volume capable of holding sharps. When closed, the top portion can abut the bottom portion at an interface. In some embodiments, the interface between the top portion and the bottom portion can comprise a seam. In some embodiments, when the shell is closed, the seam can be blocked by a gate that crosses the seam between the top portion and the bottom portion to prevent a sharp medical device from projecting out of the shell across the seam. The gate, or gates, can be integral or affixed to the top portion, the bottom portion, or both the top and bottom portions.

In some embodiments, the Sharpshell can comprise a lock. The lock can be configured to secure the top portion to the bottom portion, after closure. The lock can be permanent and irreversible, or it can be configured as reopenable. Activation of the lock, or even closure of the top portion against the bottom portion, in some embodiments, can cause a secondary lock to clamp serrated or sharp edges down onto sharps inserted into the Sharpshell, thus ensuring that they cannot be removed because a mechanical interlock has been generated.

In some embodiments, the Sharpshell can comprise internal high-friction materials to minimize the risk of the entrapped medical sharp moving once placed therein. Such high-friction materials can comprise top or bottom foam pads or other structures exposed therein.

In some embodiments, the Sharpshell can comprise a seal, or a plurality of seals, configured to prevent the escape of fluid from the internal volume of the shell. The seal can be affixed proximate to the perimeter of the shell to prevent fluid from escaping through the interface between the top portion and the bottom portion. A seal can also be affixed at or near a window area to prevent fluid leakage through the window, whether or not one or more medical sharp projects therethrough.

In some embodiments, the top portion, the bottom portion, or both portions of the shell can comprise substantially transparent materials so that items trapped within the shell can be visualized by a user.

In some embodiments, the Sharpshell can comprise a needle counting pattern or structure. Needles can be inserted into or through the needle counting pattern or structure. The needle counting pattern or structure can facilitate a clear observation of the presence and number of items inserted or placed therein. The needle counting pattern or structure can be affixed to a foam pad. The foam pad can be sandwiched between structures after closure of the shell. In other embodiments, the needle counting pattern or structure can be positioned adjacent to a transparent exterior wall of the shell so that the number of suture needles enclosed therein can be observed and counted, even after the shell has been closed.

In certain embodiments, the Sharpshell can comprise a needle removal mechanism. A hypodermic needle, attached to a syringe barrel by, for example, a Luer lock or slip Luer mechanism, can be inserted into the needle removal mechanism and then be safely removed from the syringe barrel by the user without risking injury. The needle removal mechanism can comprise a rigid bulkhead or rib, affixed to the Sharpshell such that a syringe needle can be inserted into a hole or a slot, gripped by the hole or slot such that the needle hub cannot rotate, and then removed from the syringe barrel by rotating the syringe barrel to disengage the Luer mechanism connecting the syringe barrel to the Luer lock syringe. Friction generating mechanisms can be comprised by the needle removal mechanism to resist or prevent the needle from backing out of the Sharpshell, once inserted. Beneficial features include one or more bulkhead or rib being substantially rigid and firmly affixed to the Sharpshell either on the interior (preferred) or the exterior. The hole or slot is beneficially visible to the user for precise alignment and engagement of the needle. The hole or slot can, in some embodiments, comprise a lead-in, funnel, or tapered entry path to guide or direct the sharp needle into the hole or slot to minimize difficulties in performing this procedure. The needle removal mechanism, in some embodiments, can be located generally proximate an end or side region of the Sharpshell shell and can be comprised by a window into the shell of the Sharpshell.

In other embodiments, the Sharpshell can be configured with a first internal volume that is sealed against fluid leakage, and a second internal volume that retains protruding blunt ends of medical sharps but does not prevent fluid leakage. A needle removal mechanism can be comprised or affixed to the interface between the sealed and non-sealed internal regions.

In other embodiments, the Sharpshell can comprise a scalpel control mechanism affixed to the Sharpshell in the same, or similar, fashion as the needle removal mechanism. The scalpel control mechanism can be configured to break the scalpel blade from the handle, to bend the scalpel blade to prevent removal, embed the scalpel blade in a foam, gel or other block of material, or the like.

In other embodiments, the Sharpshell system can be built into a sterile procedure tray. The Sharpshell can be affixed to the tray, it can rest within a region or space assigned for the Sharpshell, or it can be fabricated integral to the tray, itself. The Sharpshell can comprise a tear away portion of the procedure tray that provides for a small, compact structure that is more easily handled and disposed of within proper waste facilities than would be an entire procedure tray.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

These and other objects and advantages of the present invention will be more apparent from the following description taken in conjunction with the accompanying drawings.

Summary of Several Embodiments of the Invention

The present inventions may be understood through a description of its several features and characteristics, any of which may be included in its several embodiments independently so as to bring about the benefits thereof.

The present inventions may be understood by reference to the Figures that are intended as representative examples without limitation to other embodiments and variations that will be apparent to one of ordinary skill from the present disclosure.

Summary of a First Embodiment Exemplified by FIG. 1

An embodiment includes an apparatus adapted for entrapment and disposal of medical sharps comprising: (a) a shell having a first shell portion and a second shell portion; and (b) a hinge portion between the first shell portion and the second shell portion adapted to permit the first shell portion and the second shell portion to be moved between a first, open position and a second, closed position wherein the shell in the closed position defines a storage volume; (c) a high-friction pad enclosed within the storage volume when the shell in the closed position adapted to resist the dislodgement of an entrapped medical sharp once placed therein; and (d) an adhesive disposed so as to maintain the shell in the closed position.

The apparatus may additionally comprise an adhesive on the high-friction pad, and a releasable cover piece covering the high-friction pad, and may have the releasable cover piece comprise a releasable adhesive strip.

In one variation, the high-friction pad comprises a first portion having an upper surface and affixed to the first shell portion and a second portion having an upper surface and affixed to the second shell portion. One embodiment may additionally comprise an adhesive on the upper surface of the first portion, and may further include a releasable cover piece covering the adhesive on the upper surface of the first portion. In another variation, the apparatus may additionally include an adhesive on the upper surface of the second portion, and a releasable cover piece covering the adhesive on the upper surface of the second portion.

Summary of a Second Embodiment Exemplified by FIG. 2

An embodiment further includes an apparatus adapted for entrapment and disposal of medical sharps comprising: (a) a shell having a first shell portion and a second shell portion; (b) a hinge portion between the first shell portion and the shell second portion adapted to permit the first shell portion and the second shell portion to be moved between a first, open position and a second, closed position wherein the shell in the closed position defines a storage volume, the first shell portion and the second shell portion comprising interferant structure adapted to maintain the shell in the closed position, and the first shell portion and the second shell portion when in the closed position forming an opening located along an edge of at least one of the first shell portion and the second shell portion, the opening configured to allow the sharp end of a medical sharp to project into the storage volume; and (c) a high-friction pad enclosed within the storage volume when the shell in the closed position adapted to resist the dislodgement of an entrapped medical sharp once placed therein.

One embodiment may additionally comprise a plurality of engagement features disposed in the opening and shaped so as to grip the hub of a needle.

Another embodiment may additionally comprise a releasable cover piece covering the high-friction pad, and this may be a releasable adhesive strip.

In one variation, the high-friction pad may comprise a first portion having an upper surface and affixed to the first shell portion and a second portion having an upper surface and affixed to the second shell portion. This variation may also comprise a releasable cover piece covering the upper surface of the first portion and a releasable cover piece covering the upper surface of the second portion. The releasable cover pieces may comprise a releasable adhesive strip.

Summary of a Third Embodiment Exemplified by FIG. 3

An embodiment also includes an apparatus adapted for entrapment and disposal of medical sharps comprising: (a) a shell having a first shell portion and a second shell portion; (b) a hinge portion between the first shell portion and the shell second portion adapted to permit the first shell portion and the second shell portion to be moved between a first, open position and a second, closed position wherein the shell in the closed position defines a storage volume, the first shell portion and the second shell portion comprising interferant structure adapted to maintain the shell in the closed position, and the first shell portion and the second shell portion when in the closed position forming an opening located along an edge of at least one of the first shell portion and the second shell portion, the opening configured to allow the sharp end of a medical sharp to project into the sealed volume, and the first shell portion and the second shell portion forming a flexible collar portion around the opening when the shell is in the closed position; and (c) a high-friction pad enclosed within the storage volume when the shell in the closed position adapted to resist the dislodgement of an entrapped medical sharp once placed therein.

In one embodiment, the first shell portion and the second shell portion each comprise a flexible material extension that mate to form the flexible collar portion when the shell is in the closed position.

One variant may include additionally a plurality of engagement features disposed in the opening and shaped so as to grip the hub of a needle.

Another variation additionally comprises a releasable cover piece covering the high-friction pad, which may be a releasable adhesive strip.

In another variation, the high-friction pad comprises a first portion having an upper surface and affixed to the first shell portion and a second portion having an upper surface and affixed to the second shell portion; and this may additionally include a releasable cover piece covering the upper surface of the first portion and a releasable cover piece covering the upper surface of the second portion, which releasable cover pieces may comprise a releasable adhesive strip.

Summary of a Fourth Embodiment Exemplified by FIG. 4

An embodiment further includes an apparatus adapted for entrapment and disposal of medical sharps comprising: (a) a shell having a first shell portion and a second shell portion; (b) a hinge portion between the first shell portion and the shell second portion adapted to permit the first shell portion and the second shell portion to be moved between a first, open position and a second, closed position wherein the shell in the closed position defines a storage volume, the first shell portion and the second shell portion comprising interferant structure adapted to maintain the shell in the closed position; and (c) a high-friction pad enclosed within the storage volume when the shell in the closed position adapted to resist the dislodgement of an entrapped medical sharp once placed therein, the high-friction pad having a first relatively thin portion and a second relatively thin portion, whereby the high-friction pad accommodates an assembled syringe barrel and needle being supported thereupon by the first relatively thin portion being in contact with the barrel of the syringe and the second relatively thin portion being in contact with the barrel of the syringe.

In one embodiment, the apparatus additionally comprises an adhesive disposed on the high-friction pad, which optionally additionally comprises a releasable cover piece covering the high-friction pad, the releasable cover piece in one variant comprising a releasable adhesive strip.

In another embodiment, the high-friction pad has an upper surface is affixed to the first shell portion and additionally comprises a second high-friction pad having an upper surface affixed to the second shell portion. A variant of this embodiment involves the additional inclusion of an adhesive disposed on the upper surface of each the high-friction pad, with or without a releasable cover piece on the upper surface of each the high-friction pad.

Summary of a Fifth Embodiment Exemplified by FIG. 5

An embodiment further includes an apparatus adapted for entrapment and disposal of medical sharps comprising: (a) a shell having a first shell portion and a second shell portion; (b) a hinge portion between the first shell portion and the shell second portion adapted to permit the first shell portion and the second shell portion to be moved between a first, open position and a second, closed position wherein the shell in the closed position defines a storage volume, the first shell portion and the second shell portion comprising interferant structure adapted to maintain the shell in the closed position, and the first shell portion defining an opening in the shell when in the closed position, the opening configured to allow the sharp end of a medical sharp to project into the sealed volume; and (c) a high-friction pad adapted to resist the dislodgement of an entrapped medical sharp once placed therein, and having a first portion enclosed within the storage volume when the shell in the closed position, and a second portion disposed so as to be exposed through the opening.

In one embodiment, the second portion is disposed below the first portion at an angle to the first portion when the shell second portion rests on a supporting surface.

In another embodiment, the apparatus additionally comprises an adhesive on the high-friction pad, and a releasable cover piece covering the high-friction pad, which releasable cover piece may comprise a releasable adhesive strip.

In still another embodiment, the apparatus additionally comprises a releasable cover piece disposed on the bottom of the second shell portion and of sufficient length to be extended over the medical sharp extending from the opening in the shell when in the closed position, and to be adhered to the first shell portion.

Summary of a Sixth Embodiment Exemplified by FIG. 6

An embodiment also includes an apparatus adapted for entrapment and disposal of medical sharps comprising: (a) a shell having a first shell portion and a second shell portion; (b) a hinge portion between the first shell portion and the shell second portion adapted to permit the first shell portion and the second shell portion to be moved between a first, open position and a second, closed position wherein the shell in the closed position defines a storage volume, the first shell portion and the second shell portion when in the closed position forming an opening located along an edge of at least one of the first shell portion and the second shell portion, the opening configured to allow the sharp end of a medical sharp to project into the storage volume, the first shell portion and the second shell portion each comprising a flexible extension forming a flexible collar around the opening when in the closed position, the having an adhesive-bearing inner surface, and a releasable cover piece on the adhesive-bearing inner surface; (c) a high-friction pad enclosed within the storage volume when the shell in the closed position adapted to resist the dislodgement of an entrapped medical sharp once placed therein; and (d) an adhesive disposed so as to maintain the shell in the closed position.

In one embodiment, the high-friction pad is affixed to the shell second portion and the pad having a first portion and a second portion and wherein first portion is disposed at an angle to the second portion when the shell second portion rests on a supporting surface.

Summary of a Seventh Embodiment Exemplified by FIG. 7

An embodiment further includes an apparatus adapted for entrapment and disposal of medical sharps comprising: (a) a shell having a first shell portion and a second shell portion; (b) a hinge portion between the first shell portion and the shell second portion adapted to permit the first shell portion and the second shell portion to be moved between a first, open position and a second, closed position wherein the shell in the closed position defines a storage volume, the first shell portion and the second shell portion when in the closed position forming an opening located along an edge of at least one of the first shell portion and the second shell portion, the opening configured to allow the sharp end of a medical sharp to project into the storage volume, the first shell portion and the second shell portion each comprising a flexible extension forming a flexible collar around the opening when in the closed position, the having an adhesive-bearing inner surface, and a releasable cover piece on the adhesive-bearing inner surface; (c) a high-friction pad enclosed within the storage volume when the shell in the closed position adapted to resist the dislodgement of an entrapped medical sharp once placed therein, wherein the high-friction pad comprises a first portion having an upper surface and affixed to the first shell portion and a second portion having an upper surface and affixed to the second shell portion; and (d) an adhesive disposed so as to maintain the shell in the closed position.

In one embodiment, the apparatus additionally comprises a releasable cover piece disposed over the adhesive.

In another embodiment, the apparatus according additionally comprises a sharp-penetration-resistant sleeve disposed on the side of the first portion opposite its upper surface, and a sharp-penetration-resistant sleeve disposed on the side of the second portion opposite its upper surface, or only on either of these surfaces.

In yet another embodiment, the high-friction pad comprises a first portion having an upper surface and affixed to the first shell portion and a second portion having an upper surface and affixed to the second shell portion, and wherein the adhesive is disposed upon at least one of the surfaces, and in one variant may additionally comprises a releasable cover piece disposed over the adhesive, such as a releasable adhesive strip.

In another variant the adhesive is disposed upon both of the upper surfaces and additionally comprising a releasable cover piece covering the upper surface of the first portion and a releasable cover piece covering the upper surface of the second portion, and optionally each of the releasable cover pieces may comprise a releasable adhesive strip.

Summary of an Eighth Embodiment Exemplified by FIG. 8

An embodiment also includes an apparatus adapted for entrapment and disposal of medical sharps comprising: (a) a shell having a first shell container portion having an opening, and a second shell lid portion; and (b) a hinge portion between the first shell container portion and the shell second lid portion adapted to permit the first shell container portion and the second shell lid portion to be moved between a first, open position and a second, closed position wherein the shell in the closed position defines a storage volume, the first shell container portion and the second shell lid portion comprising interferant structure adapted to maintain the shell in the closed position, and the first shell portion and the second shell lid portion each containing a high-friction pad adapted to resist the dislodgement of an entrapped medical sharp once placed therein; wherein the edge portion of the opening comprises an engagement feature disposed in the opening and shaped so as to grip the hub of a syringe needle, and wherein the first shell container portion is adapted to stand upright and wherein the first shell container portion is of sufficient length to contain a syringe needle when extended therein and its hub is engaged by the engagement feature, and wherein the storage volume is of sufficient length to contain a syringe needle and syringe needle hub when the shell in the closed position.

In one embodiment, the apparatus additionally comprising an adhesive on the high-friction pad contained in second shell lid portion, and a releasable cover piece covering the adhesive, and this may be a releasable adhesive strip.

Summary of a Ninth Embodiment Exemplified by FIG. 9

An embodiment further includes an apparatus adapted for entrapment and disposal of medical sharps comprising: a shell defining storage volume, the shell having a top portion, a side wall portion and a bottom base portion, the base portion being at least as large in area as the top portion, the shell adapted to stand upright upon the base so as to present an exposed the top portion and an exposed the side wall portion; the top portion comprising (a) at least one syringe cap holding aperture adapted to releasably accept a syringe cap so as to allow a capped syringe to be releasably extended into the storage volume and (b) at least one syringe capture aperture adapted to capture and hold a syringe hub as its syringe needle extends into the storage volume; and wherein the shell comprises a suture needle aperture adapted to receive suture needles into the storage volume. In different variants, this embodiment of the invention may have only the syringe cap holding aperture, or only the syringe capture aperture.

In one embodiment, the side wall portion comprises the suture needle aperture, and in one variation the apparatus may additionally comprise a high-friction pad contained within the shell and the friction pad being exposed through the at least one syringe capture and the suture needle aperture.

In another embodiment, the side wall portion comprises the suture needle aperture, and one variant features a releasable cover piece covering the suture needle aperture which may be a releasable adhesive strip.

In a further embodiment, the base portion is of a material adapted to resist sliding friction as compared to the material comprised by the a top portion and side wall portion. As an alternative, the entire shell may be made from the same material, which is resistant to sliding friction Summary of a Tenth Embodiment Exemplified by FIG. 10

An embodiment further includes an apparatus adapted for entrapment and disposal of medical sharps comprising: a shell defining storage volume, the shell having a top portion, a side wall portion, a bottom wall portion and a base portion, the base portion adapted to rest upon a supporting surface so as to present an exposed the top portion and an exposed the side wall portion, with the bottom wall portion supported above the supporting surface; the top portion comprising a suture needle aperture; the side portion comprising and (a) at least one syringe capture aperture adapted to capture and hold a syringe Luer fitting as its syringe needle extends into the storage volume; and (b) a scalpel aperture adapted to receive and secure scalpel blades into the storage volume; and an extension panel extending below the bottom wall portion when it is supported above the supporting surface, the extension panel comprising a syringe cap holding aperture adapted to releasably accept a syringe cap so as to allow a capped syringe to be releasably extended therethrough and astride the bottom wall portion. In different variants, this embodiment of the invention may have only the syringe capture aperture, or only the scalpel aperture.

One embodiment involves the base portion comprising the extension panel.

In another embodiment, the syringe cap holding aperture has a central axis, and additionally comprises a blocking wall portion extending across the central axis, to prevent the syringe cap from being extended further than operationally required to permit the syringe cap to be placed and removed during a procedure. The base portion may include this blocking wall portion.

In still another embodiment, the syringe cap holding aperture has a central axis, and additionally comprises a blocking wall portion extending across the central axis, and a secondary wall portion disposed at an angle to the blocking wall portion; and wherein the base portion comprises the extension panel, the blocking wall portion and the secondary wall portion.

One variation involves additionally including a releasable cover piece covering the suture needle aperture, which may be a releasable adhesive strip.

Summary of an Eleventh Embodiment Exemplified by FIG. 11

An embodiment also includes an apparatus adapted for entrapment and disposal of medical sharps comprising: (a) a shell having a first portion comprising (1) a top portion and (2) at least three side wall portions, and an extension panel, and a second portion comprising (1) a bottom wall portion (2) at least three side wall portions and (3) a base portion; and (b) a hinge between the first portion and the second portion adapted to permit the first portion and the second portion to be moved between a first, open position and a second, closed position wherein the shell in the closed position defines a storage volume and positions the base portion so as to rest upon a supporting surface so as to present an exposed the top portion, an exposed bottom portion and one of the side wall portions, with the bottom wall portion supported upon the supporting surface; and wherein: the storage volume of the bottom portion optionally comprising a foam or foam-like insert adapted to releasably accept a suture needle; the side wall portion comprising (a) at least one syringe capture aperture adapted to capture and hold a syringe Luer fitting as its syringe needle extends into the storage volume; and (b) a scalpel aperture adapted to receive and secure scalpel blades into the storage volume; and an extension panel extending below the top portion when the shell is in an open position and is supported above the supporting surface, the extension panel comprising a syringe cap holding aperture adapted to releasably accept a syringe cap so as to allow a capped syringe to be releasably extended therethrough and astride the top wall portion. In different variants, this embodiment of the invention may have only the syringe capture aperture, or only the scalpel aperture.

In one embodiment, the base portion comprises the extension panel.

In another embodiment, the syringe cap holding aperture has a central axis, and additionally comprises a blocking wall portion extending across the central axis, to prevent the syringe cap from being extended further than operationally required to permit the syringe cap to be placed and removed during a procedure. The base portion may include this blocking wall portion.

In yet another embodiment, the syringe cap holding aperture has a central axis, and additionally comprises a blocking wall portion extending across the central axis, and a secondary wall portion disposed at an angle to the blocking wall portion; and wherein the base portion comprises the extension panel, the blocking wall portion and the secondary wall portion.

This hinged design does not have a suture needle aperture in the top portion like the unhinged variant shown in Figure. Instead, the suture needles may be are inserted into foam (or another high-friction material) that fills the larger bottom portion.

Summary of a Twelfth Embodiment Exemplified by FIG. 12

An embodiment also includes an apparatus adapted for entrapment and disposal of medical sharps comprising: a shell defining storage volume, the shell having a top portion, a side wall portion and a bottom base portion, the base portion being at least as large in area as the top portion, the shell adapted to stand upright upon the base so as to present an exposed the top portion and an exposed the side wall portion; the top portion comprising (a) at least one syringe cap holding aperture adapted to releasably accept a syringe cap so as to allow a capped syringe to be releasably extended into the storage volume and (b) at least one syringe capture aperture adapted to capture and hold a syringe hub as its syringe needle extends into the storage volume; and (c) a suture needle and scalpel aperture adapted to receive suture needles and scalpel blades into the storage volume. In different variants, this embodiment of the invention may have only the syringe cap holding aperture, only the syringe capture aperture, or only the scalpel aperture.

In one embodiment, the apparatus additionally comprises a high-friction pad contained within the shell and which high-friction pad is exposed through the at least one syringe capture and/or the suture needle aperture, and this may include a releasable cover piece covering the suture needle and scalpel aperture, which releasable cover piece may comprise a releasable adhesive strip.

In another variant, the base portion is of a material adapted to resist sliding friction as compared to the material comprised by the a top portion and side wall portion, or the entire shell may be made of such material.

Additionally an adhesive pad may be included in the base portion to temporarily attach the base portion to the procedure tray or table.

Summary of a Thirteenth Embodiment Exemplified by FIG. 13A-13E

The present embodiment further includes an apparatus adapted for entrapment and disposal of medical sharps comprising: a shell defining storage volume, the shell having a top portion, a side wall portion and a bottom base portion, the base portion being at least as large in area as the top portion, the shell adapted to stand upright upon the base so as to present an exposed the top portion and an exposed the side wall portion; the top portion comprising (a) at least one syringe cap holding aperture adapted to releasably accept a syringe cap so as to allow a capped syringe to be releasably extended into the storage volume and (b) at least one syringe capture aperture adapted to capture and hold a syringe hub as its syringe needle extends into the storage volume; and wherein the shell comprises a suture needle aperture adapted to receive suture needles into the storage volume, and (c) at least one scalpel blade window in the top portion.

In one embodiment, the side wall portion comprises the suture needle aperture, and in one variation the apparatus may additionally comprise a high-friction pad contained within the shell and exposed through at least one the syringe capture and the suture needle aperture.

In another embodiment, the side wall portion comprises the suture needle aperture, and one variant features a releasable cover piece covering the suture needle aperture which may be a releasable adhesive strip.

In still another embodiment, the suture needle aperture may extend into both the top portion and side wall portion.

In a further embodiment, the base portion is of a material adapted to resist sliding friction as compared to the material comprised by the a top portion and side wall portion, or the entire shell may be made of such material.

The present invention includes all medical, clinical or surgical uses of the apparatus embodiments and variants of the present invention, as well as generally for the attachment, containment or entrapment and disposal of any hazardous materials or items to which the apparatus embodiments and variants of the present invention might find beneficial application.

Any of the apparatus embodiments of the present invention may be contained within a procedure tray or kit, or may be affixed to a procedure tray or kit, for any given medical, clinical or surgical procedure involving the use of medical sharps.

An embodiment includes medical, clinical or surgical post-procedure involving the use of any of the apparatus embodiments and variants of the present invention for the attachment, containment or entrapment and disposal of contaminated medical sharps, including without limitation, sutures, scalpels and syringes.

An embodiment further includes performing these methods within the examination or treatment room, office or operating suite where any given medical, clinical or surgical procedure involving the use of medical sharps occurs.

The method may also include optionally disposing of contaminated medical sharps entrapped or contained in any of the apparatus embodiments and variants of the present invention, such as by placing the apparatus embodiments and variants of the present invention in another sharps disposal container, such as any of those known in the art.

A method for attachment, containment or entrapment and disposal of contaminated medical sharps comprises generally the steps of providing, at the point of use or contamination, any of the apparatus embodiments and variants of the present invention in a sterile package, removing it from the sterile package, placing it in the sterile field in an position so as to expose the areas or spaces for sharps insertion, attachment or entrapment, inserting used/contaminated medical sharps into the apparatus of the present invention, sealing, closing, adhering the medical sharps as the case may be through action of the apparatus of the present invention, and disposing of the apparatus of the present invention bearing the attached, contained or entrapped contaminated medical sharps.

The method may also include optionally the step of providing the apparatus of the present invention within a procedure tray or kit, such as by affixing it to the procedure tray or kit.

The method may also include optionally the step of separating the apparatus of the present invention from the procedure tray or kit after the apparatus has been filled with medical sharps and closed to attach, contain or entrap contaminated medical sharps.

The method may also include optionally the further step of preventing removal of medical sharps from the apparatus of the present invention by clamping down on the inserted medical sharp with a jam cleat or jaw apparatus.

One variation of the method for entrapment and disposal of contaminated medical sharps comprises generally the steps of: providing, at the point of use, a container comprising a puncture resistant shell, wherein the puncture-resistant shell comprises a first portion, a second portion, and a pre-defined hinge separating the first portion from the second portion and allowing the first portion to rotate about an axis such that the first portion can be brought into apposition against the second portion, and a window; wherein the window comprises apparatus configured for removal and retention of medical sharps inserted therethrough; removing the container from a sterile package; placing the container in the sterile field with the first portion rotated away from the second portion such that the shell is open; inserting used medical sharps into the shell, through the window; grabbing the medical sharps within the window; removing handles, barrels, or other grasping components from the medical sharps; and preventing removal of the medical sharps from the window area.

The method may also include optionally the step of providing the puncture resistant shell within a procedure tray or kit, such as by affixing it to the procedure tray or kit.

The method may also include optionally the step of separating the puncture resistant shell from the procedure tray or kit after the apparatus has been filled with medical sharps and closed to attach, contain or entrap contaminated medical sharps.

The method may also include optionally the further step of preventing removal of medical sharps from the window area by clamping down on the inserted medical sharp with a jam cleat or jaw apparatus.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIGS. 1C-10 provide additional views of the Sharpshell of FIGS. 1A and 1B.

FIG. 2A illustrates an oblique view of an open Sharpshell A comprising a shell having upper or top portion and bottom or lower portion, a lower layer of foam, an upper layer of foam, a puncture-resistant shell, projections and receivers positioned at the end of the interface between the upper and bottom portions of the shell, and an opening configured to entrap and retain medical sharps inserted therethrough;

FIG. 2B illustrates an oblique view of the closed Sharpshell of FIG. 2A, comprising an opening configured to stabilize, entrap, and retain the hub of hypodermic needles inserted therethrough, according to one embodiment;

FIGS. 2C-2L provide additional views of the Sharpshell of FIGS. 2A and 2B.

FIGS. 3C-3L provide additional views of the Sharpshell of FIGS. 3A and 3B.

FIG. 4A illustrates an oblique view of an open Sharpshell C comprising a two part shell separated by a hinge and including an internal volume sufficiently large to completely entrap a hypodermic needle and syringe barrel according to one embodiment;

FIG. 4B illustrates an oblique view of the Sharpshell of FIG. 4A in the closed configuration, according to one embodiment;

FIGS. 4C-4L provide additional views of the Sharpshell of FIGS. 4A and 4B.

FIG. 5A illustrates an oblique view of an open Sharpshell D comprising a two part shell separated by a hinge and including a lower sharps collection pad, a lid, and a shroud to overlap and contain the protruding blunt ends of medical sharps, according to one embodiment;

FIG. 5B illustrates an oblique view of the Sharpshell of FIG. 5A in the closed configuration, according to one embodiment;

FIGS. 5C-5N provide additional views of the Sharpshell of FIGS. 5A and 5B.

FIG. 6A illustrates an oblique view of an open Sharpshell comprising a two part shell separated by a hinge and a rounded exterior cross-section with a lower collection pad that protrudes into the top portion and a collapsible adhesive collar around an opening to the collection pad, further comprising a beveled collection pad on the end that is distal to the adhesive collar, according to one embodiment of the invention;

FIG. 6B illustrates an oblique view of the Sharpshell of FIG. 6A in the closed configuration wherein suture needles in the counting region are visible through a beveled portion of the clear top portion and wherein the collar can be folded inward to secure any medical sharps projecting out of the collection pad through the opening, according to one embodiment;

FIGS. 6C-6P provide additional views of the Sharpshell of FIGS. 6A and 6B.

FIG. 7A illustrates an oblique view of an open Sharpshell F comprising a shell and a lid separated by a hinge with a suture needle counting and collection pad within the lid of the shell and an opening to the central volume of the shell, the housing of the opening being affixed to the shell, the opening further comprising features for removing medical sharps from their handles or barrels, according to one embodiment;

FIG. 7B illustrates an oblique view of the Sharpshell of FIG. 7A in the closed configuration wherein the top has been closed to encase the sharps and the opening, according to one embodiment;

FIGS. 7C-7M provide additional views of the Sharpshell of FIGS. 7A and 7B.

FIGS. 8C-8M provide additional views of the Sharpshell of FIGS. 8A and 8B.

FIG. 9A illustrates an oblique view of a Sharpshell comprising an inverted, flared, axially elongate shell, a closed top, bottom and side surfaces, features for hypodermic needle exchange, suture needle counting and retention area, and syringe needle entrapment and removal features, according to one embodiment;

FIG. 9B illustrates a top view of the Sharpshell of FIG. 9A showing the needle exchange and needle removal mechanism in more detail, according to one embodiment;

FIG. 10 illustrates a Sharpshell comprising rectilinear geometry and stability enhancing standoffs, a non-openable central volume, and features to accept syringe needles, suture needles, and scalpels, according to one embodiment;

FIG. 13A illustrates an oblique view of a Sharpshell comprising an inverted, flared, axially elongate shell, a closed top, bottom and side surfaces, features for hypodermic needle exchange, suture needle counting and retention area, and syringe needle entrapment and removal features, according to one embodiment of the invention;

FIG. 13B illustrates a top view of the Sharpshell of FIG. 13A showing the needle exchange and needle removal mechanism in more detail, according to one embodiment of the invention;

FIGS. 13C-13E provide additional views of the Sharpshell 1300 of FIGS. 13A and 13B.

DETAILED DESCRIPTION

In accordance with one or more embodiments of the present invention, a plurality of embodiments of a Sharpshell system is described herein. In order to fully specify this preferred design, various embodiment specific details are set forth, such as the shape and size of the receptacle as well as the dispenser. It should be understood, however that these details are provided only to illustrate the presented embodiments, and are not intended to limit the scope of the present invention.

Figure 1A:
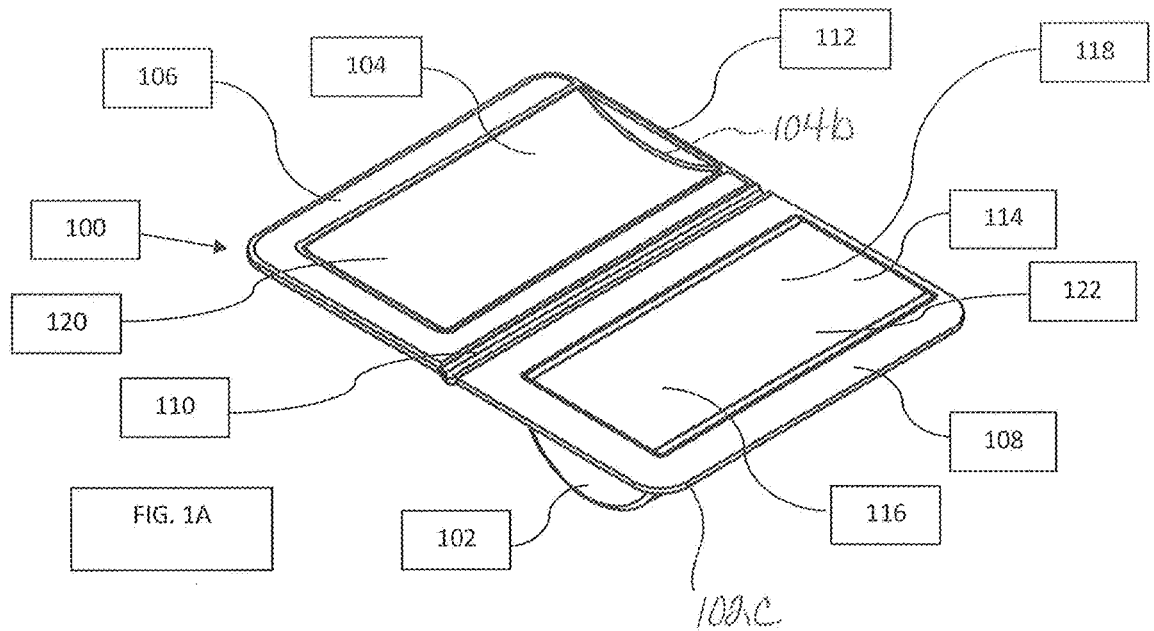
FIG. 1A illustrates an oblique view of an open Sharpshell H comprising curvilinear surfaces, a flat bottom, which can comprise a slightly curvilinear contour, and transparent shell materials, according to one embodiment.
Figure 1B:
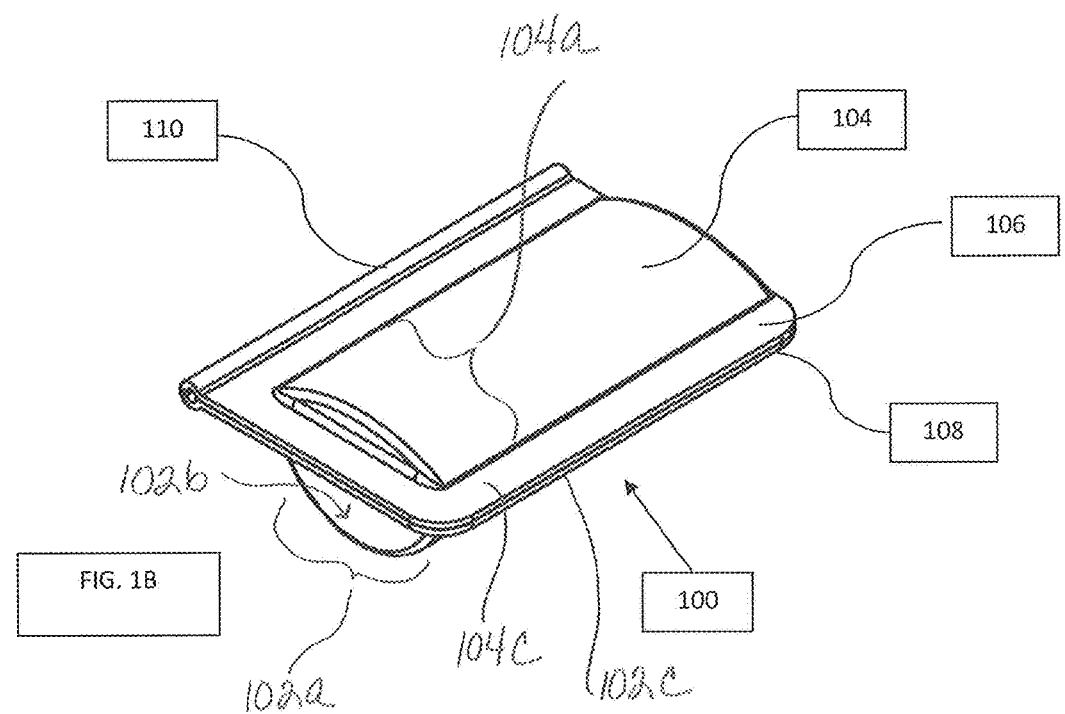
FIG. 1B illustrates an oblique view of the Sharpshell device of FIG. 1A following closure of the top portion against the bottom portion, according to one embodiment.
Figure 1E:
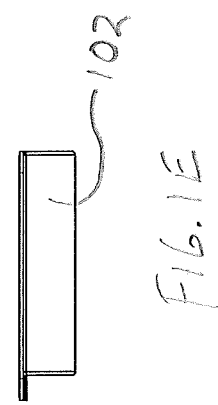
Figure 1C:
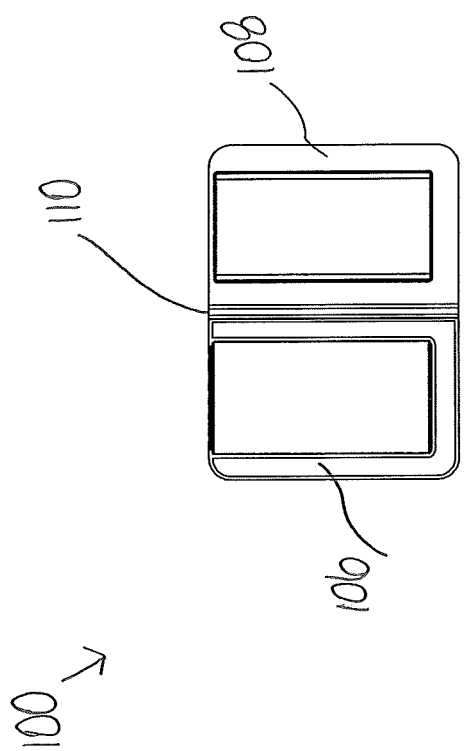
Figure 1D:
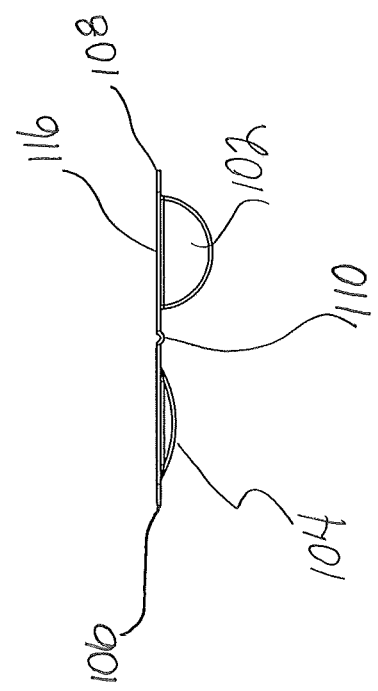

FIG. 1A illustrates an oblique view of an open Sharpshell 100 comprising a bottom portion 102 further defining a first portion of an interior volume 118, a top portion 104 further defining a second portion of an interior volume 120 (the interior volumes 118 and 120 defining the interior volume of the Sharpshell 100 when in the closed position shown in FIG. 1B), a bottom lip 108, a top lip 106, a hinge 110, a flat bottom 112, a foam receiver pad 114, and a label 116. The Sharpshell 100 can further comprise a needle or scalpel hub release mechanism.

Referring to FIG. 1A, the bottom shell 102 is affixed to the top portion 104 by the hinge 110, which can be affixed (or integral) to the bottom portion 102, the top portion 104, or both. The foam receiver pad 114 can be placed in whole or in part within the interior volume 118 of the bottom portion 102 or it can be affixed to one or more of the interior walls of the bottom portion 102. The foam receiver pad 114 can be retained within the bottom portion 102 by friction, compression, adhesion or the like. The bottom lip 108 and the top lip 106 can be formed integrally, or affixed to, to the bottom portion 102 and the top portion 104 respectively. In an embodiment, there is no foam within the volume of the top portion. In other embodiment, the top portion volume 118 is filled, wholly or at least in part, by foam. In another embodiment, the bottom portion lip 106 can comprise a receiver while the top portion lip 108 comprises a projection that mates with the bottom portion receiver, serving as a gate to block passage of any sharp object through the interface between the bottom lip 108 and the top lip 106. The projection and the receiver can be formed integrally to the top lip 106 and bottom lip 108 respectively. The Sharpshell 100 can further comprise a suture needle counting region or receiver 122.

The label 116 can be affixed to the foam receiver pad 114 using adhesives or it can be directly printed thereon. The label 116 can comprise images of suture needle counting areas, or the like. In other embodiments, a recapping and needle exchange mechanism can be comprised by a structure affixed within the foam receiver pad 114. The re-capping structure can comprise features similar or the same as to of a hypodermic needle cover or cap. In other embodiments, the recapping needle exchange mechanism may allow for temporary holding of a hypodermic needle cover or cap.

The top portion 104, the bottom portion 102, and the hinge 110, which henceforth shall be characterized as the shell, can be fabricated by processes such as, but not limited to, thermoforming, injection molding, or the like. The shell can comprise materials such as, but not limited to, polyester (PET), polyimide (Nylon), poly amide, polypropylene, polyethylene (PE), high density polyethylene (HDPE) polyether ether ketone (PEEK), polyurethane (PU), polyvinyl chloride (PVC), polysulfone, polyacetal, acrylic, copolymers of the aforementioned, or the like. The shell can further comprise additional layers of cellulose or other laminates or composites of the aforementioned. The materials chosen are considered for their puncture resistance to sharp medical devices such as, but not limited to, scalpel blades, hypodermic needles, suture needles, and the like. The shell materials are configured to resist puncture with the aforementioned devices under normal manipulation and forces encountered in handling. The shell materials described above are usable for all of the embodiments described within this specification.

In a preferred embodiment, the top portion 104 is visually transparent to allow the user to observe the presence and count the numbers of sutures, needles, scalpels, or other medical sharps contained therein. In another embodiment, the end of the shell away from the flat end 112 comprises an opening or window further comprising a needle hub, a scalpel blade, or both, detachment mechanism. In a preferred embodiment, the bottom 112 can be slightly curvilinear, rather than being substantially flat.

FIG. 1B illustrates an oblique view of the closed Sharpshell 100. The closed Sharpshell 100 comprises the top portion 104, the bottom portion 102, the top lip 106, the bottom lip 108, and the hinge 110. The construction includes curvilinear central portion (i.e., 102a and 104a) with a flattened end cap (i.e., 102b and 104b) at one end and a flange lip (i.e., 102c and 104c) protruding outward and surrounding the end cap at the other end.

Referring to FIG. 1B, in an embodiment, the closed shell in this exemplary embodiment is approximately 1.5 to 2.0 inches wide, approximately 2 to 4 inches long, and about 1 to 2 inches thick. The size of the closed shell is such that the closed Sharpshell fits easily within the human hand and can be transported securely and disposed of using existing sharps disposal containers, such as by being placed therein. The shell material in this exemplary embodiment may have a thickness ranging from about 0.01 to about 0.10 inches, with a preferred thickness of about 0.02 to about 0.06 inches with a more preferred range of about 0.03 to about 0.05 inches.

In the illustrated embodiment, the bottom portion 102 and the top portion 104 are curvilinear in longitudinal cross-section. In other embodiments, the bottom portion 102 and/or the top portion 104 can comprise flat or rectilinear surfaces which can enhance stability and facilitate placement on a table, suture tray, procedure kit, or the like.

When closed, the Sharpshell top portion 104 can lock to the bottom portion 102 by way of interference tabs or locks which are located proximate the flanges 106 and 108. The interference tabs are affixed or integrally formed with the flanges of top lip 106 and bottom lip 108, or some other portion of the shell, such that male portions of the interference tabs project into and lock with complementary structures integral to the female portions of the interference tabs. These interference tabs can connect the top portion 104 to the bottom portion 102 with a tactile and audible snap that confirms closure and prevents re-opening.

The foam or pad 114 can comprise the receiver or counting region 122 for the placement of suture needles. This receiver or counting region 122 can be disposed such that it is visible through the closed shell. The receiver or counting region 122 can be disposed such that it is situated up against a top portion 104 of the closed shell 100 or it can be spaced away from the envelope of the shell.

Additional views of the Sharpshell 100 are provided in FIGS. 1C-1O wherein like numerals refer to the features and portions described above.

FIG. 1I-1K shows the top portion 104 to the bottom portion 102 such as in the form of a clear plastic shell, top portion 104 being a lid with label indicia, and which may be provided with a blister package covering, as well as optional tab 124 with peel off adhesive label. This Figure also shows that the bottom portion 102 may contain a cardboard tube containing a foam center portion, as the foam or pad 114, and that the shell may be a clear plastic material.

This allows used suture needles to be inserted from above into the foam pad in numbered targets for accounting purposes, while syringe needles and scalpels may be inserted at the top of the device as shown in latter FIGS. 1M-1N.

FIG. 1L shows how entrapped suture needles are visible through the clear lid of 104.

FIGS. 1M-1N show the insertion of syringe needles in the closed shell from above. FIG. 1M shows a top oblique view of the Sharpshell 100 showing the foam center portion marked to direct users when inserting sharps, with scoring to accommodate scalpels.

FIG. 1M shows an elevation oblique view of the Sharpshell 100 showing the insertion of sharps into the top foam portion of the device.

FIG. 1N shows an elevation oblique view of the Sharpshell 100 showing the insertion of sharps into the top foam portion of the device for further processing and/or disposal.

FIG. 2A illustrates an oblique view of another embodiment of an open Sharpshell 200 comprising an top portion shell 216, a bottom portion shell 204, a hinge 214, an upper foam layer 210, a lower foam layer 232, an upper volume 226, a lower volume 228 (the top or upper volume 226 and bottom or lower volume 228 defining the interior volume of the Sharpshell 200 when in the closed position shown in FIG. 2B), an opening or window 208, a needle removal mechanism 230 (See FIG. 2B), a plurality of needle removal features 212, a projecting engagement feature 220, a release paper 224, and a projection receiver 218 (See FIG. 2B).

Referring to FIG. 2A, this embodiment is somewhat larger in length and width than the device of FIG. 1A as described above. The needle removal features 212 can be affixed to, or integral with, the window 208. The needle removal features 212 can be affixed to, or integral with, the window needle removal mechanism 230.

The lower foam pad 232 comprises labeling which can include suture needle counting targets 232A, syringe orientation guides 232B, optional syringe needle recapping features, and the like. The upper foam pad 210 can comprise biohazard labeling 210A, instructions for use 210B, safety instructions 210C, and the like. The upper foam pad 210, the lower foam pad 232, or both can optionally comprise adhesive to assist with retention of sharps placed within the Sharpshell 200. The adhesives can be pressure sensitive and can further comprise a release paper 224, which is removed prior to inserting used medical sharp devices within the Sharpshell 200. The release paper 224 can comprise a lift tab for easy grip and/or labeling such as instructions for use, warnings, and the like. The release paper 224 can comprise a siliconized paper or polymer structure. The adhesive can be affixed as a laminate to the foam pads 210, 232, or it can be applied as a liquid or aerosol spray thereto. The adhesives can comprise materials such as, but not limited to, cyclohexane, 2-methylpentane, isobutene, propane, dimethyl ether, 3-methlpentane, 2,3 dimethylbutane, 2,2 dimethylbutane, hexane, polyurethane, and the like.

The opening 208 allows syringes, scalpels, or the like, to be inserted therein such that the needle hub removal features 212 can grip the hub of the hypodermic needle. The needle removal features 212 are configured to grip the polymeric hub of the hypodermic needle and permit friction, polymeric blocking or interference fit therein and prevention of rotary motion of the hypodermic needle hub while the hypodermic syringe barrel can be unscrewed therefrom and detached. In an embodiment, the needle removal features 212 comprise star shaped or cross-shaped fenestrations into which the needle hub, comprising star or cross-shaped projections can be inserted and gripped. In another embodiment, the needle removal feature 212 can comprise a plurality of teeth-like inserts that protrude into the needle removal feature 212 into which the needle hub can be inserted and gripped. Preferably the needle removal mechanism 212 is fabricated from rigid materials that can reliably grip the polymeric hub of the hypodermic needle and permit friction.

The needle shaft removal mechanisms 230, which can be located proximate the opening 208 are configured to grasp or grip the shaft of the hypodermic needle or scalpel and prevent or resist removal of an inserted needle or scalpel. The needle shaft removal mechanism 230 can, in an embodiment, comprise a jam-cleat function the splits open easily upon insertion of the medical sharp therethrough but closes against the medical sharp with increasing force as the medical sharp is withdrawn proximally. The needle shaft removal mechanism 230 can comprise metal or polymeric planar structures that are split radially and can be bent or curved distally away from the point of entry of the medical sharp. A small fenestration, hole, or window, smaller in diameter than that of the envisioned hypodermic needle, can be located within the slit to facilitate insertion of the medical sharp. Preferably the needle shaft removal mechanism is fabricated from extremely hard metals that can dig into the stainless steel shaft of the hypodermic needle or scalpel blade. Once inserted, proximal withdrawal of the syringe needle causes the split, sharp metal surfaces to dig into the syringe needle with increasing force as the hypodermic needle is withdrawn, thus preventing withdrawal.

In other embodiments, a braided tubular structure can be comprised within the opening 208. The braided tubular structure can further comprise aggressive adhesives on its interior to grab a syringe needle. The braided tubular structure is affixed to the opening 209 at its distal end farthest from the window. Proximal withdrawal of the syringe needle causes the braided tubular structure to reduce in diameter and grab the syringe needle, thus preventing its withdrawal. The braided tubular structure can comprise metallic or polymeric materials.

The materials of the Sharpshell 200 can be similar to, or the same as, those of the Sharpshell 100 of FIG. 1A.

FIG. 2B illustrates an oblique view of a closed Sharpshell 200 comprising a shell 202 further comprising a bottom portion 204, an top portion 216, an interface 206 between the top portion 216 and the bottom portion 204, a projecting gate receiver 218 in the top portion 216, a projecting gate 220 (See FIG. 2A) in the bottom portion 204, a hinge 214, and an opening 208. The Sharpshell 200 further comprises an inner volume 226+228 when the top portion is closed against the bottom portion. The Sharpshell 200 also comprises, a label 222, a needle hub receiver 212 (See FIG. 2A) located within the opening 208 and further comprising one or more hub grasping features configured to reside adjacent or within the needle removing feature 212.

Referring to FIG. 2B, the top portion 216 is affixed to the bottom portion 204 by the hinge 204, which can be integral or affixed to the top portion 216, the bottom portion 204, or both. The opening 208 comprises an operable entry into the inner volume 222 through which the sharp ends of hypodermic needles can be inserted into the inner volume 222. The hubs of the hypodermic needles are used to releasably connect the hypodermic needle to a syringe barrel, generally by way of a slip Luer or Luer lock adapter. Such connections can also be made using threaded adapters, bayonet mounts, quick connects, or the like. The hub receiver 212, in the illustrated embodiment comprises a series of grooves arrayed in a star or cross-pattern. A needle hub can be inserted into the receiver 212 until the hub of the needle undergoes an interference fit with the receiver 212. The star or cross pattern can further grab a complementary star or cross feature on the needle hubs and permit unscrewing or release of the syringe barrels. The opening 208 can further comprise an elastomeric membrane which serves to seal the opening 208 if the needle is withdrawn for any reason. The opening 208 can, in other embodiments, comprise a hardened, sprung jam-cleat that comprises a center hole or plurality of slits, or both, such that a hypodermic needle can be inserted therethrough but upon withdrawing of the hypodermic needle, the jam cleat closes with increasing tightness around the needle and prevents its removal.

The shell 202 is substantially puncture-resistant to hypodermic needles and scalpel blades and can comprise polymeric materials, organic fiber materials, metals, or a combination thereof in the form of laminates or extra layers. For example, a fiberboard liner can be disposed within the top portion 216, the bottom portion 204, or both to enhance the resistance to sharp penetration through the walls of the Sharpshell.

The dimensions of the closed Sharpshell 200 can range from approximately 1.5 to 4.0 inches wide, approximately 2 to 6 inches long, and about 0.5 to 2 inches thick.

The opening 208 can comprise an optional guard, shield, frame, flange, or boss, which surrounds the opening 208 and defines the window region.

The adhesive is configured such that when the top portion 216 is closed against the bottom portion 204, the adhesive can grip the shaft of an inserted sharp and assist with retention. The adhesive further acts as a locking mechanism to assist in retaining the top portion 216 closed against the bottom portion 204.

In other embodiments, the Sharpshell 200 can comprise an optional irreversible lock. The irreversible lock includes features that prevent grabbing the lock to disengage it. In yet other embodiments, the lock can be reversible such that the lock can be grasped and opened. The lock can comprise features such as a tab, oversnap, latch, threaded feature, or the like.

The projection and the receiver serve not only to block penetration of the interface by a medical sharp when the shell is closed, but also serves to enhance the fluid-tight seal of the shell when the Sharpshell is closed. Furthermore, a polymeric, elastomeric membrane can be affixed within the Sharpshell, preferably in the region of the opening 208 to serve as a seal to prevent any leakage through the opening 208.

Additional views of the Sharpshell 200 are provided in FIGS. 2C-2L wherein like numerals refer to the features and portions described above.

FIG. 2I shows that the top portion 216 may be provided with a blister package covering.

FIG. 2J shows that the bottom portion 204 may contain a cardboard lining or equivalent material beneath the foam pad contained therein, as shown in FIG. 2K.

FIG. 2K shows the release paper 224 with adhesive release tab. From this Figure one can also appreciate how hub receiver 212 may provide a molded engagement structure to allow the Luer locks 241 to be snapped into place and held while the syringe barrels are disconnected.

FIG. 2I shows how syringes 240 may be placed so as to engage hub receiver 212 as the syringe needles extend into the Sharpshell 200. The syringe barrels may then be removed while the syringe Luer locks 241 remain secured in hub receiver 212 as shown in FIG. 2J.

Figure 3A:
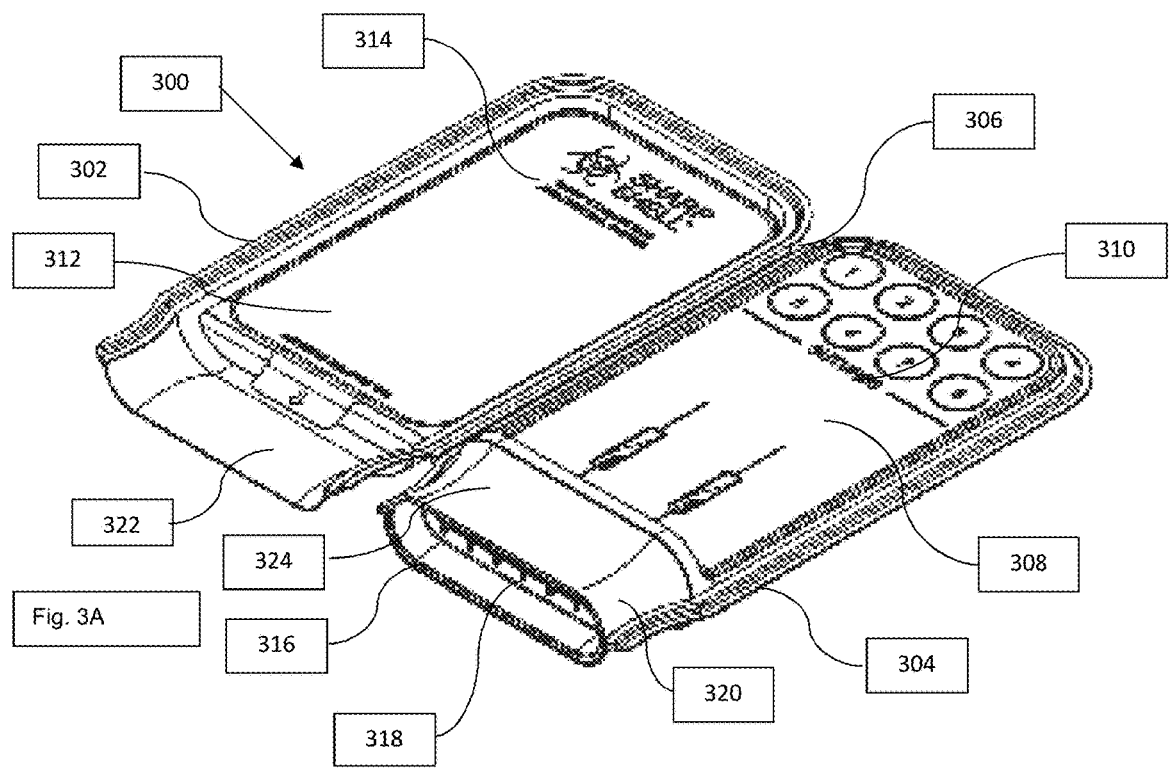
FIG. 3A illustrates an oblique view of an open Sharpshell B comprising the elements of the apparatus of FIG. 2A but with the addition of a deformable collar surrounding the opening, according to one embodiment.

FIG. 3A illustrates a Sharpshell apparatus 300 in the open configuration comprising an top portion 302, a bottom portion 304, a hinge 306, a lower foam layer 308, a lower label area 310, an upper form area 312, an upper label area 314, an opening 316, a sharps detachment mechanism 318, and a deformable collar system 320, further comprising a collar support 322 and a collar 324. The top portion 302 and the bottom portion 304 comprise all or a portion of a shell 326.

Figure 3B:
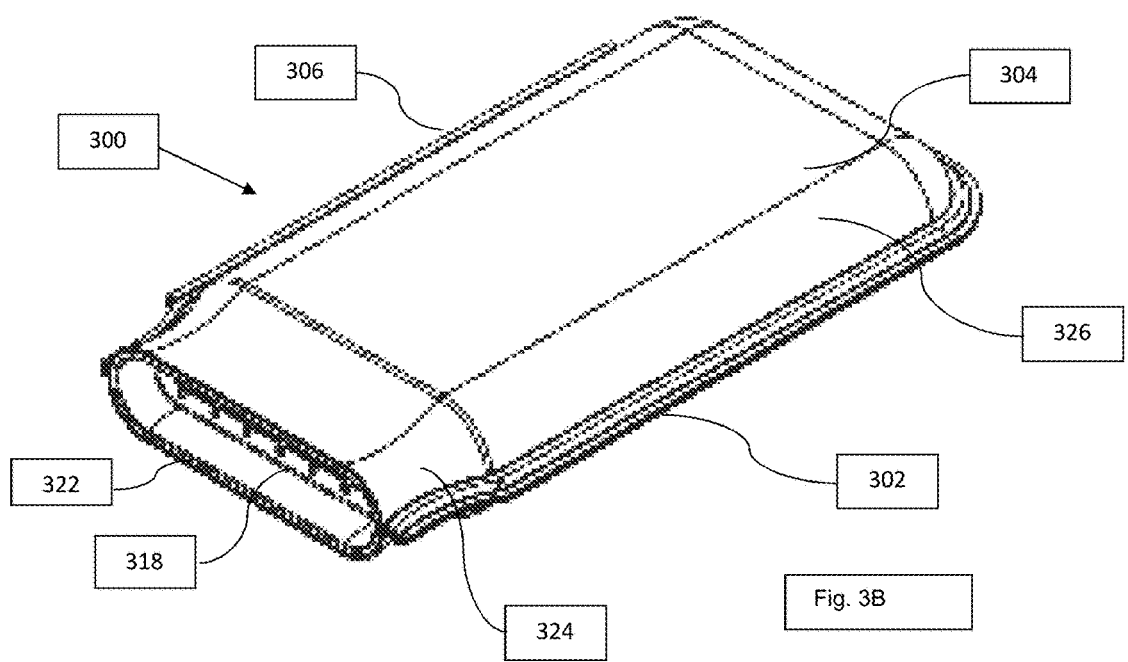
FIG. 3B illustrates an oblique view of the Sharpshell of FIG. 3A in the closed configuration, according to one embodiment.
Figure 3E:
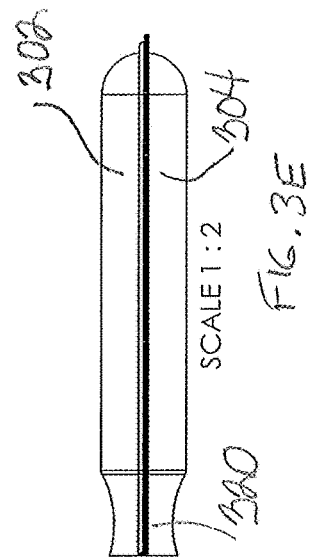
Figure 3C:
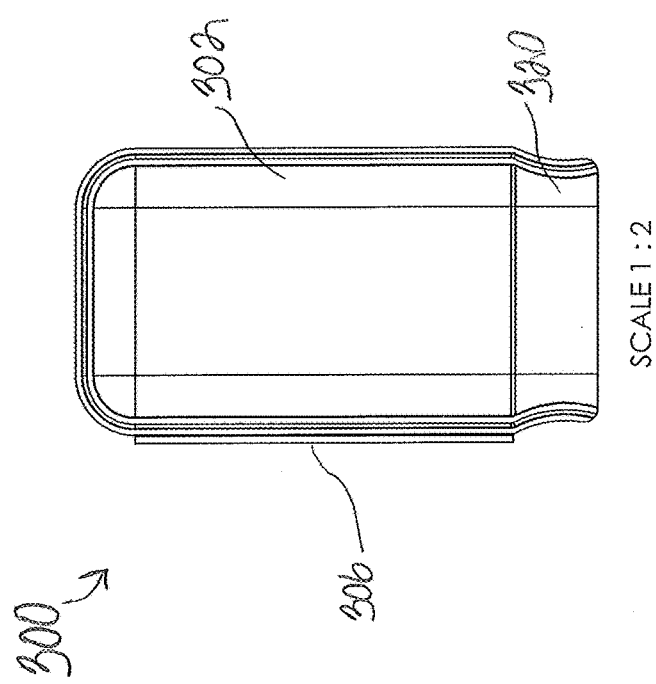
Figure 3D:
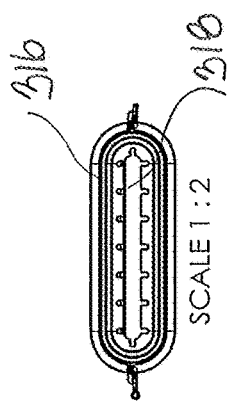
Figure 3H:
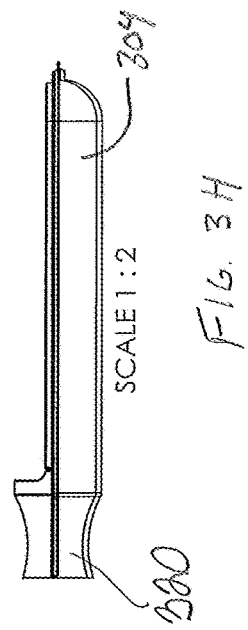
Figure 3F:
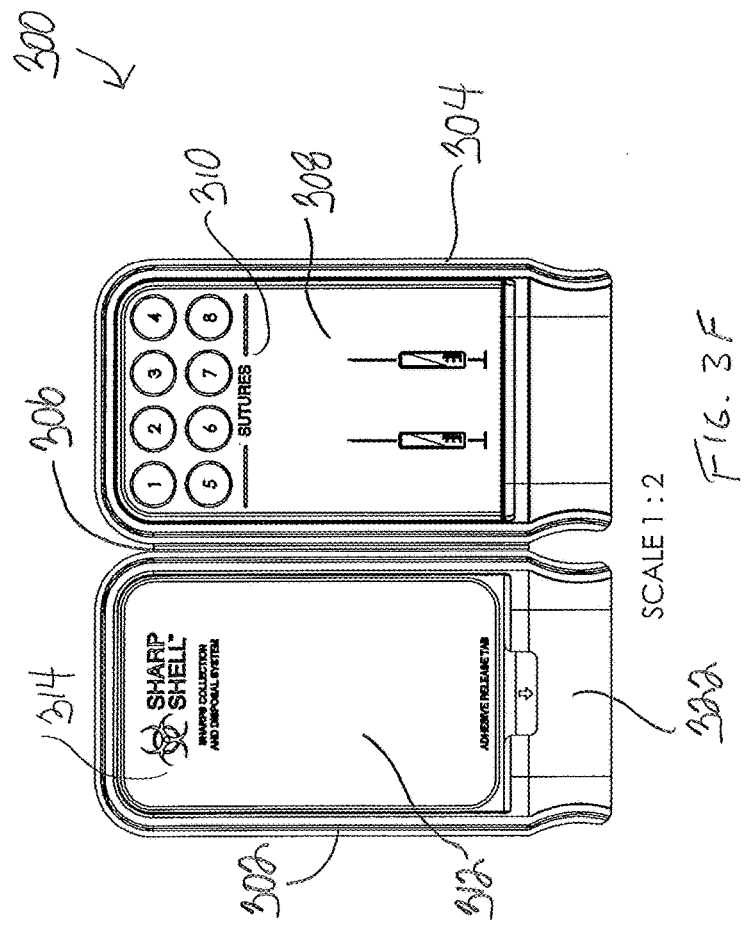
Figure 3G:
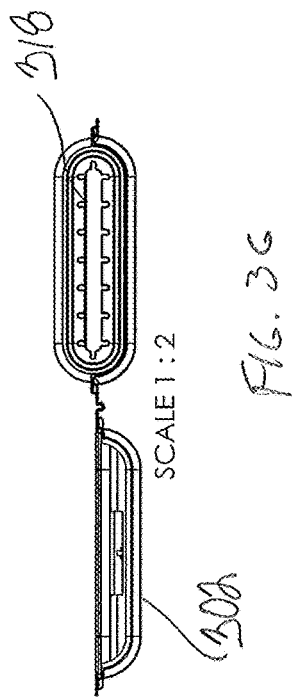

FIG. 3B illustrates the Sharpshell apparatus 300 in the closed configuration. The Sharpshell 300 comprises a shell 326, further comprising the top portion shell 302 and the bottom portion shell 304, and an internal volume 328. The collar 324 has been deformed inward and pressed against the collar support 322 such that a trapped sharp is restrained by the collapsed collar 324.

Referring to FIG. 3B, the deformable collar 324 can comprise flexible materials. The deformable collar 324 can comprise polymeric materials. The deformable collar 324 can be affixed to the top portion 302, the bottom portion 304, or both. The deformable collar 324 can comprise adhesives affixed to interior surfaces of the deformable collar 324 to facilitate grabbing and holding any medical sharps projecting therethrough. The deformable collar 324 can comprise construction that assumes a first relaxed, open shape, a second, high energy state, and a third relaxed state. The collar 324 can be forced past the high energy state configuration to achieve the third relaxed state, which is preferably a closed or semi-closed configuration. This high energy state can be achieved with the use of elastomers, semi-rigid or rigid materials, or the like. The deformable collar 324 can be sized to grab the sides of projecting medical sharps or it can be sized to completely encapsulate the length and even the ends of medical sharps. In yet other embodiments the deformable collar 324 can be replaced or augmented by a strap that is affixed to the shell 326 and wraps around the end of projecting medical sharps and then can be affixed to the shell 326 at a second (or same) location. Such a strap can comprise adhesive or friction generating materials or properties. The purpose of the deformable collar 324 is to irreversibly lock or secure a medical sharp to the Sharpshell 300. The collar support 322 can comprise rigid materials and be configured to snap the collar 324 across its high-energy second configuration and into the third, low energy configuration.

The needle removal apparatus 318 can be affixed proximate the opening 316. The syringe needle removal system 318 can be configured similarly to other sharp detachment mechanisms described herein.

Additional views of the Sharpshell 300 are provided in FIGS. 3C-3L wherein like numerals refer to the features and portions described above.

FIG. 3I shows that the upper label area 314 may be provided with a blister package covering.

FIG. 3J shows that the bottom portion shell 304 may contain a cardboard lining or equivalent material beneath the foam pad contained therein, as shown in FIG. 3K.

FIG. 3K shows the release paper 224 with adhesive release tab. From this Figure one can also appreciate how sharps detachment mechanism 318 may provide a molded engagement structure to allow the Luer locks 341 to be snapped into place and held while the syringe barrels are disconnected.

FIG. 3I shows how syringes 340 may be placed so as to engage sharps detachment mechanism 318 as the syringe needles extend into the Sharpshell 300. The syringe barrels may then be removed while the syringe Luer locks 341 remain secured in sharps detachment mechanism 318 as shown in FIG. 3J.

Figure 4L:
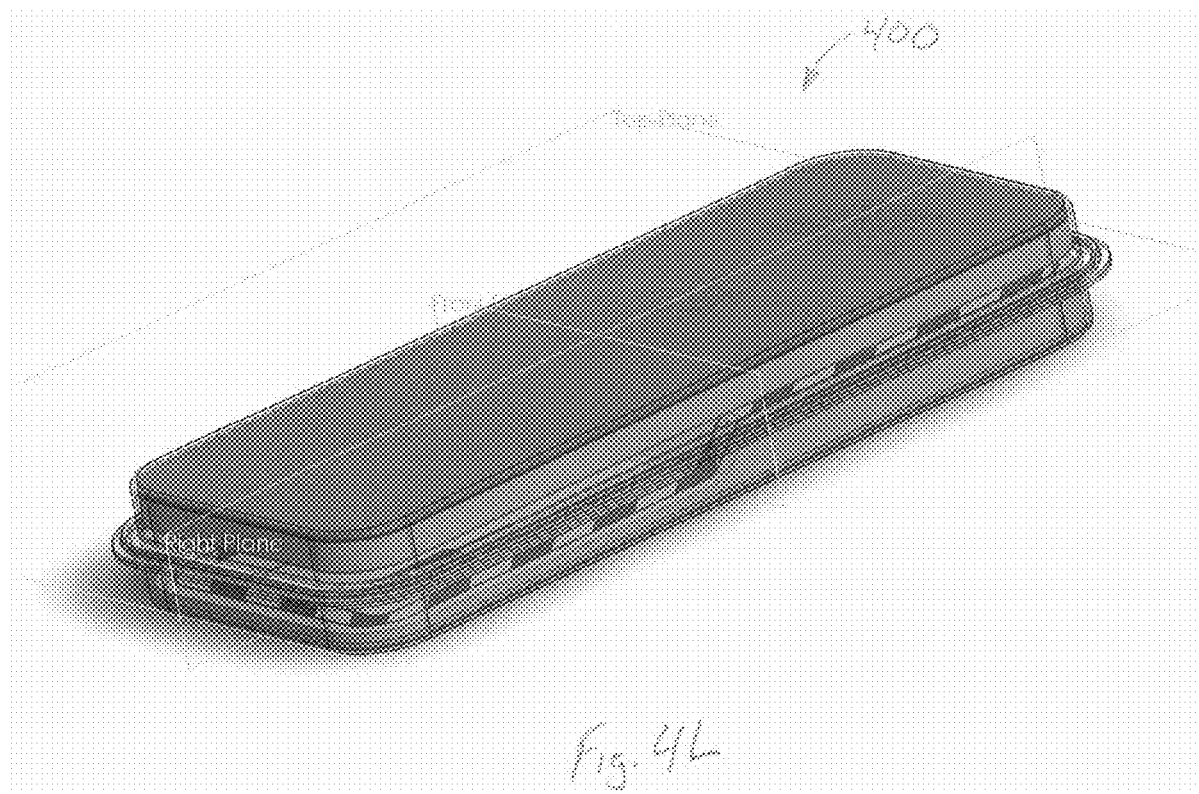

FIG. 4A illustrates a Sharpshell apparatus 400 in the open configuration. The Sharpshell apparatus 400 comprises a bottom portion 404, and top portion 402, defining a shell 426 having an internal volume 428, and a hinge 406. The Sharpshell apparatus 400 further comprises a lower pad 408, further comprising a step 430, an upper pad 412, a lower pad label 410, and an upper pad label 414. The lip of the bottom portion 402 further comprises a gate feature 416 that fits into a complementary gate feature 418 on the top portion 404.

Referring to FIG. 4A, the step 430 permits insertion of a hypodermic needle or other medical sharp while keeping the handle or barrel roughly parallel to the plane of the lower shell portion 404. The top portion 402 and the bottom portion 404 are sufficiently large as to completely enclose a pre-defined range and number of syringe barrels, scalpel blades, or the like.

The lower pad label 410 can comprise a needle counting area with a plurality of boxes and numbers, letters, or the like. The lower pad label 410 can also comprise images of sharps such as syringes or scalpels to illustrate the orientation of insertion, cautions, warnings, instructions, and the like.

FIG. 4B illustrates the Sharpshell apparatus 400 comprising the top portion 402, the bottom portion 404, and the hinge 406. The top portion 402 has been rotated about the hinge 406 and closed against the bottom portion 404 to form an internal volume (not visible). There are no windows in the top portion 402 or the bottom portion 404 and nothing projects out of the Sharpshell 400. The Sharpshell 400 is configured to completely enclose a medical sharp and any handles, barrels, or the like such that no part of the used medical device projects beyond the boundaries of the shell 426. The exterior of the shell 426 can comprise one or more labels 420 including descriptions, warnings, cautions, instructions, and the like.

The Sharpshell 400 can further comprise openable or irreversible locks to maintain closure once the upper shell portion 402 is closed against the bottom portion 404. Such locks can comprise snaps with edges that are hidden and cannot be grasped for re-opening, adhesive closure systems, snaps that grab and lock with no opening structures, and the like.

The Sharpshell 400 can further comprise edge seals to prevent fluid leakage out through the interface between the top portion 404 and the bottom portion 402. The edge seals can comprise mechanisms such as, but not limited to, close-fitting structures, gaskets, adhesive layers, and the like. The edge seals can be integrated into the gate features 416, 418, or both.

The Sharpshell 400 can further comprise gates 418, 416 surrounding a portion, or all, of the perimeter of the top portion 402, the bottom portion 404, or both. The gates 418, 416 can be configured to project across the interface between the bottom portion 404 and the top portion 402 to prevent a sharp device from projecting out across the interface. The gates can be affixed, or integral, to the top portion 402, the bottom portion 404, or both. The gates can be fabricated from the same, or different, puncture resistant materials as the top portion 402 and the bottom portion 404.

Additional views of the Sharpshell 400 are provided in FIGS. 4C-4L wherein like numerals refer to the features and portions described above.

FIG. 4I shows the exterior of the shell 426 with label indicia.

FIG. 4J shows that the bottom portion shell 404 may contain a cardboard lining or equivalent material beneath the foam pad 430 contained therein, as shown in FIG. 4K.

FIG. 4K shows how syringes 440 may be placed in bottom portion 404 so as to be completely contained in the Sharpshell 400 once closed. The syringe barrels are accommodated by the step-down taper of the foam pad 430 contained therein.

Figure 5N:

FIG. 5A illustrates a Sharpshell apparatus 500 in the open configuration. The Sharpshell apparatus 500 comprises a shell 526, further comprising a bottom portion 504, a top portion 502, an internal volume 528, and a hinge 506. The Sharpshell apparatus 500 further comprises a lower pad 508, further comprising an angled syringe or scalpel target 530, an exterior shell label 514, an adhesive layer 534, a cover strip 532, a securing strap 512, and a lower pad label 510.

Referring to FIG. 5A, the adhesive layer 534 is affixed to the top portion lid 502. The release paper or cover strip 532 covers the adhesive layer 534 and is removed before closing the lid or top portion 502.

Referring to FIG. 5A, the target 530 is disposed at an angle to the planes of the shell 526 to allow for stability against a flat surface but the ability to insert medical sharps into the lower pad 508, through the target 530. The shell 526 can be transparent, translucent, or opaque.

Labels 510 can comprise instructions for use, suture needle counting patterns, orientation of syringes or scalpels, warnings, cautions, or the like.

The top portion 502 can comprise the strap 512, which can be pulled out from the bottom portion 504 and secured to the top portion 502.

The pad 508 can comprise open-cell absorbent foam, gel, adhesive or the like.

FIG. 5B illustrates the Sharpshell 500 of FIG. 5A in the closed position. The Sharpshell 500 comprises the bottom portion shell 504 and the top portion shell 502, which is a lid. The adhesive layer 534 locks the lid or top portion 502 down against the bottom portion 504. The strap 512 can be pulled around the extents of a projecting blunt handle of a medical sharp to secure the handle to the Sharpshell apparatus 500 at the top portion 502. The strap 512 can be secured with a lock, snap, fastener, adhesive, or the like by the user and is preferably pre-secured to the shell 526, either by affixation or integral construction. The shell 526 can comprise a shroud 524 that surrounds the target area 530.

In one embodiment, bottom portion 504 may be provided on its bottom with a plastic wrapper that may be released by release tab 535 which wrapper and or tab may be provided with adhesive so as to be wrapped about the closed Sharpshell apparatus 500 to cover the target area 530 once having engaged scalpels and/or syringes for disposal.

The perimeter of the top portion 502 and the bottom portion 504 can be configured to seal to each other to prevent fluid leakage around the perimeter. The target area 530 can comprise a membrane or gasket to prevent fluid leakage out through the target area 530 even with medical sharps projecting therethrough.

The shroud 524 can comprise rigid or flexible materials and can further comprise adhesive interior surfaces. The shroud 524 can be configured to collapse inward from a first low energy configuration, across a second, high energy configuration to a third, low energy, closed configuration.

Additional views of the Sharpshell 500 are provided in FIGS. 5C-5N wherein like numerals refer to the features and portions described above.

FIG. 5I shows the bottom portion shell 504 and the top portion shell 502, which is a lid with label indicia, and which may be provided with a blister package covering.

FIG. 5J shows that the target 530 is disposed at an angle to the planes of the shell 526 to allow for stability against a flat surface but the ability to insert medical sharps into the lower pad 508, through the target 530. This allows suture needles to be inserted from above into the foam pad, while syringe needles and scalpels may be inserted at an angle.

FIG. 5K shows a lower oblique view of the shell 526 with bottom portion 504 provided on its bottom with a plastic wrapper that may be released by release tab 535 which wrapper and or tab may be provided with adhesive so as to be wrapped about the closed Sharpshell apparatus 500 to cover the target area 530 once having engaged scalpels and/or syringes for disposal.

FIG. 5L shows an upper oblique view of the shell 526.

FIG. 5M shows a progression of views showing (1) the opening of the shell 526, and removal of the cover by tab 512 to expose the adhesive target area and to expose the target area 530 for insertion of medical sharps 540, (2) the closure of the top portion 502 to close shell 526 with pressure to seal, (3) the untaping of the plastic wrapper by tab 535 which then (4) is wrapped around the shell 526 to capture medical sharps 540 with the adhesive tab sticking to the top of top portion 502 to be secured for further processing and/or disposal.

FIG. 6A illustrates an oblique view of an open Sharpshell 600 comprising a first portion 602 of a shell 612, a second portion 604 of the shell 612, a hinge 606, a collection pad 608, a beveled collection pad facet 614, and a collapsible collar or shroud 610.

Referring to FIG. 6A, the first portion 602 and the second portion 604 of the shell 612 comprise a rounded exterior cross-section. The collection pad 608 can comprise an oblique facet 614 on one end. The collection pad 608 is affixed to one of the shell portions and protrudes into the other portion. The collection pad 608 is illustrated as being affixed or inserted into the second portion 604. The collapsible collar 610 can be affixed to one or more portions 602, 604, and surrounds an opening 616 to the collection pad 608.

The collection pad 608 is fabricated from materials that are environmentally friendly, such as cellulose or other biodegradable materials. The shell 612 can be fabricated from puncture resistant materials and can be opaque, translucent, or substantially transparent so as to be able to visualize the contents. Due to the materials selection, the Sharpshell 600 is generally larger in dimensions that the Sharpshell 100, although they are similar in configuration. The facet 614 can comprise a suture needle counting area or other features.

The collection pad 608 can further comprise a syringe needle exchange mechanism, feature, or structure, integrally formed therein or affixed thereto. Such syringe needle exchange mechanism can be comprised by any of the Sharpshell devices described within this specification.

FIG. 6B illustrates an oblique view of the Sharpshell 600 in the closed configuration wherein suture needles in a counting region printed onto the oblique portion 614 (see FIG. 6A) of the collection pad 608 can be rendered visible through a clear region 620 comprising some, or all, of the shell portion 602. The collar 610 can be folded inward to secure any medical sharps projecting out of the collection pad through the opening 616. The collar 610 can be affixed to the first portion 602, the second portion 604, or both.

Referring to FIG. 6B, the interior of the collar 610 can comprise adhesives or other friction generating structures to retain any sharps contained therein.

The collapsible collar 610 can comprise adhesive internal surfaces or surfaces comprising high friction, such as soft rubbers or silicone elastomers. The collapsible collar 610 can comprise a high-energy state through which it is manually forced to move it from a first, open, low energy state to a third close, low energy state.

Figure 6P:
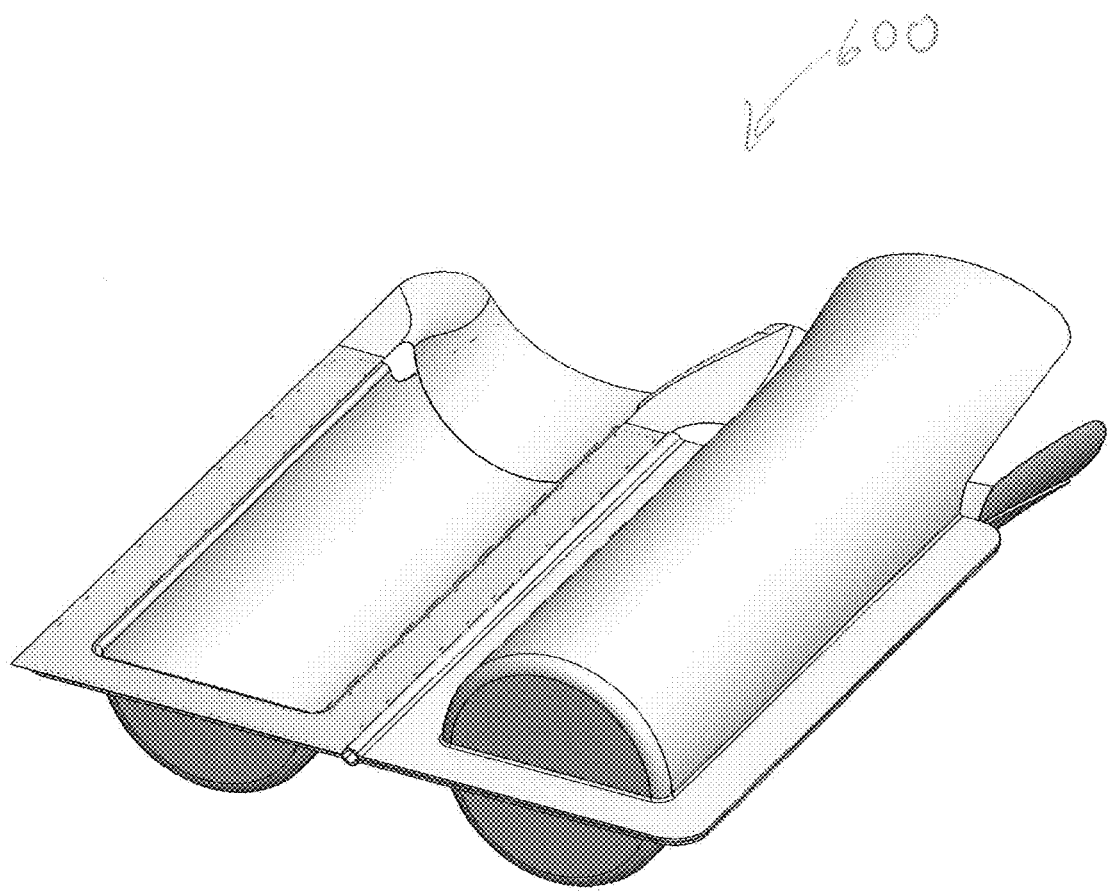

Additional views of the Sharpshell 600 are provided in FIGS. 6C-6P wherein like numerals refer to the features and portions described above.

FIG. 6I shows the first portion 602 and the second portion 604, which is a lid with label indicia, and which may be provided with a blister package covering, as well as the collar 610. This Figure also shows that the second portion 604 may contain a cardboard tube with a foam center portion, and that the shell may be a clear plastic material. The collar 610 is shown with a peel-off adhesive label.

FIG. 6J shows that the oblique portion 614 is disposed at an angle to the planes of the shell 608 to allow for stability against a flat surface but the ability to insert medical sharps into oblique portion 614. This allows used suture needles to be inserted from above into the foam pad in numbered targets for accounting purposes, while syringe needles and scalpels may be inserted at the top of the device as shown in latter Figures. This view also shows the removal of the adhesive label prior to the folding of the first portion 602.

FIG. 6K shows an upper oblique view of the shell 608 after the adhesive label is removed, the adhesive label being colored or provided with indicia to caution users when inserting sharps.

FIG. 6L shows an upper oblique view of the shell 608 after first portion 602 is folded over.

FIG. 6M shows a top oblique view of the shell 608 showing the foam center portion marked to direct users when inserting sharps, with scoring to accommodate scalpels.

FIG. 6N shows an elevation oblique view of the shell 608 showing the insertion of sharps into the top foam portion of the device.

FIG. 6O shows an elevation oblique view of the shell 608 showing the insertion of sharps into the top foam portion of the device, and the closure of the adhesive collapsible collar 610 about the inserted sharps for further processing and/or disposal.

Figure 7M:
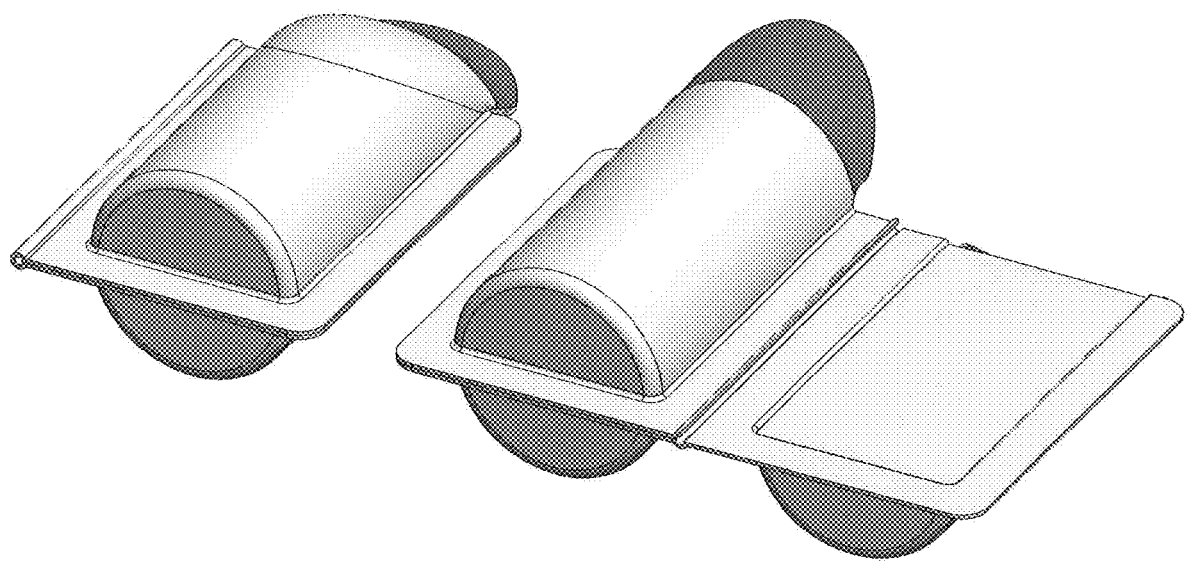

FIG. 7A illustrates an oblique view of an open Sharpshell 700 comprising a bottom shell 702 and a lid 704 operably connected by a hinge 706. The bottom shell 702 comprises a suture needle counting and collection pad 708. The shell 702 comprises an opening 710 to a central volume 712 of the shell 702, the opening 710 being affixed to the shell 702. The opening 710 can comprise features 714 for removing medical sharps from their handles or barrels. A secondary pad 716 can optionally be comprised within the central volume 712.

FIG. 7B illustrates an oblique view of the Sharpshell 700, in the closed configuration, wherein the top or lid 704 has been closed against the shell 702 to encase the sharps and the window region 710.

Referring to FIG. 7B, the shell 702, the lid 704, or both, can be opaque, translucent, or substantially transparent so as to be able to visualize the contents. The shell 702 can be fabricated from puncture resistant materials such as, but not limited to, fiberboard or other environmentally friendly materials and can be generally non-transparent. The shell 702 and the lid are fabricated from materials and structures that are puncture-resistant to medical sharps under normal handling conditions. The interface between the lid 704 and the shell 702 can optionally comprise a fluid-tight seal or gasket. A gate between the lid 704 and shell 702 can also be provided to keep suture needles from protruding through any interface.

Additional views of the Sharpshell 700 are provided in FIGS. 7C-7G wherein like numerals refer to the features and portions described above.

FIG. 7G shows the shell 702 and the lid 704, the shell may be made from molded pulp with infused resin in the main shaded area for puncture resistance.

FIG. 7H shows the suture needle counting and collection pad 708. This allows used suture needles to be inserted from above into the foam pad 708 in numbered targets for accounting purposes, while syringe needles and scalpels may be inserted at the top of the device as shown in latter Figures. This view also shows the device prior to removal of the adhesive label and prior to folding the lid 704.

FIG. 7H shows an upper oblique view of the shell 702 and the lid 704 after the adhesive label is removed. The shell 702 and/or the lid 704 also may be provided with adhesive to maintain the device in the closed position after the shell 702 and the lid 704 are folded together.

FIG. 7J shows an upper oblique view of the shell 702 after the lid 704 is folded over. This view shows the foam center portion marked to direct users when inserting sharps, with scoring to accommodate scalpels.

FIG. 7K shows an elevation oblique view of the shell 702 showing the insertion of sharps into the top foam portion of the device.

FIG. 7L shows an elevation view of the shell 702 showing the insertion of sharps into the top foam portion of the device, and the closure of the adhesive collapsible collar about the inserted sharps for further processing and/or disposal.

Figure 8A:
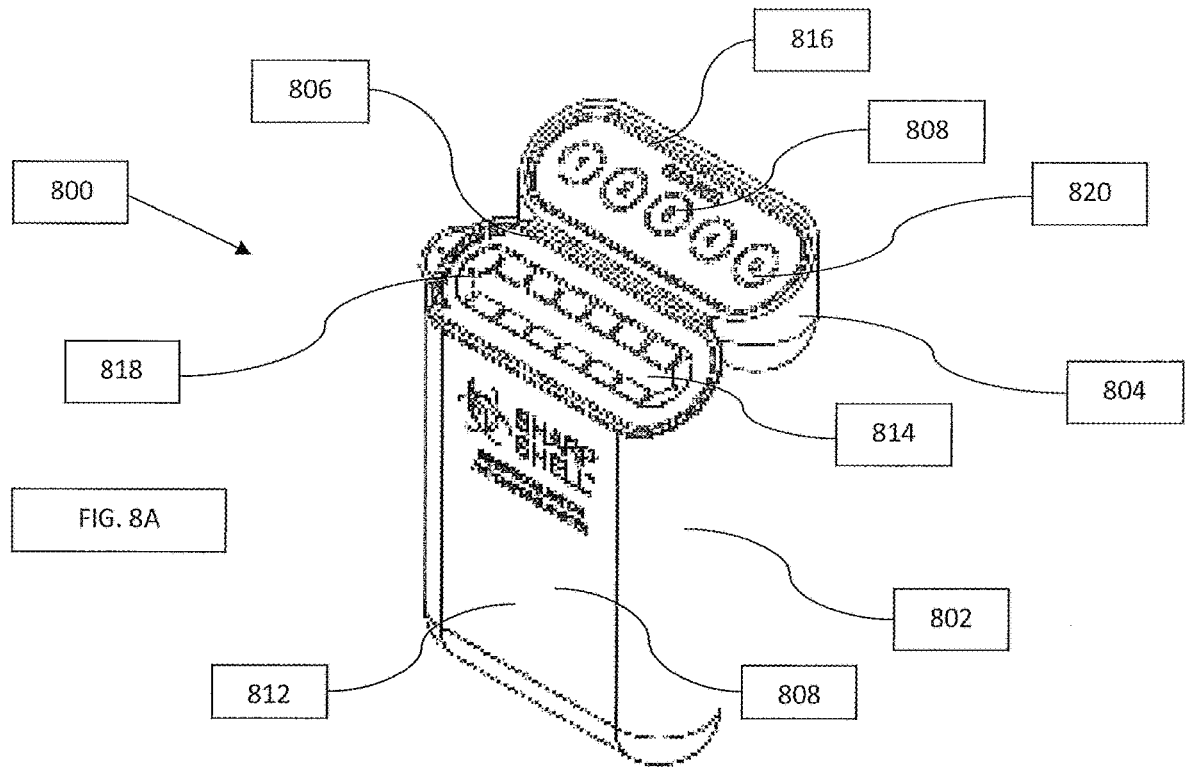
FIG. 8A illustrates an oblique view of an open Sharpshell G comprising a hard or semi-hard shell, a hollow internal volume with an optional foam internal pad, a ring around the hub grabbing element which comprises adhesive protected by release paper, and a lid separated by a hinge with a suture needle counting an collection pad within the lid of the shell and an opening to the central volume of the shell, the housing of the opening being affixed to the shell, the opening comprising features for grabbing and removing medical sharps from their handles or barrels, according to one embodiment.

FIG. 8A illustrates an oblique view of an open Sharpshell 800 comprising a hard or semi-hard shell 802, a hollow internal volume 812 with an optional foam internal pad 808, a hinge 806, a hub grabbing element 814 which comprises adhesive protected by release paper 816, and a lid 804 separated by the hinge 806 with a suture needle counting an collection pad 808 within the lid 804, and an aperture 818 operably opening to the central volume 812 of the shell 802, the window 818 region being affixed to the shell 802, the aperture 818 comprising features 814 for grabbing and removing medical sharps from their handles or barrels. The lid 804 can further comprise an optional suture needle counter 820.

Figure 8B:
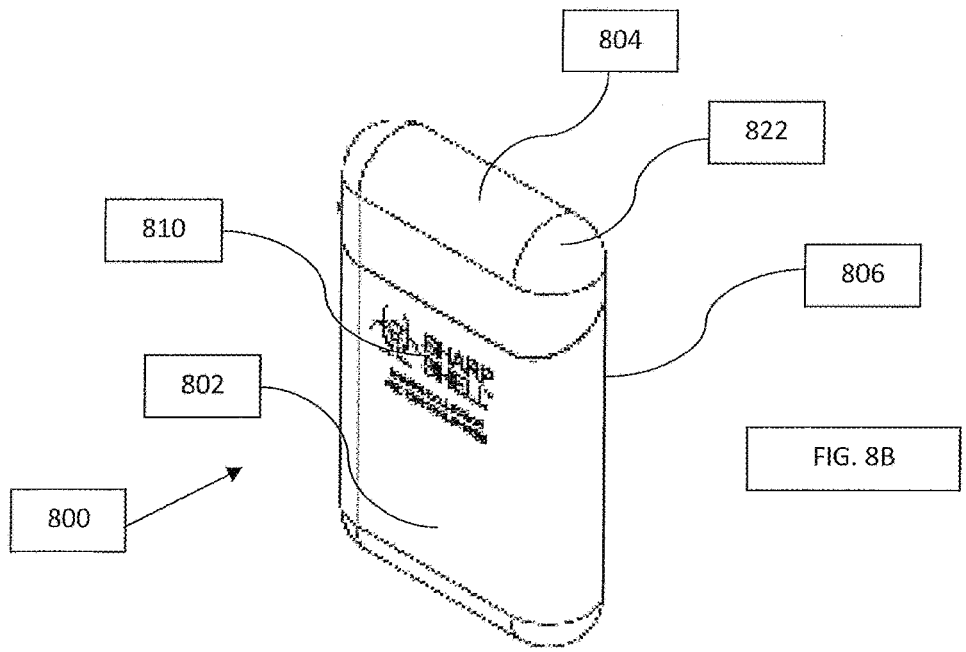
FIG. 8B illustrates an oblique view of the Sharpshell of FIG. 8A in the closed configuration wherein the top has been closed, according to one embodiment.
Figure 8A:
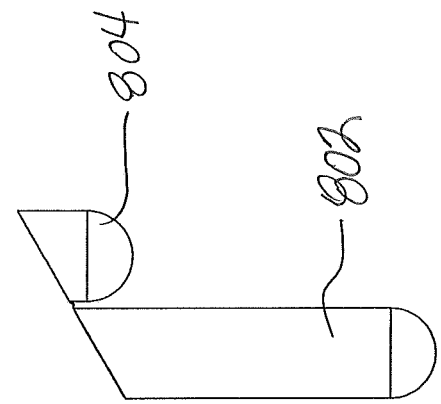
Figure 8F:
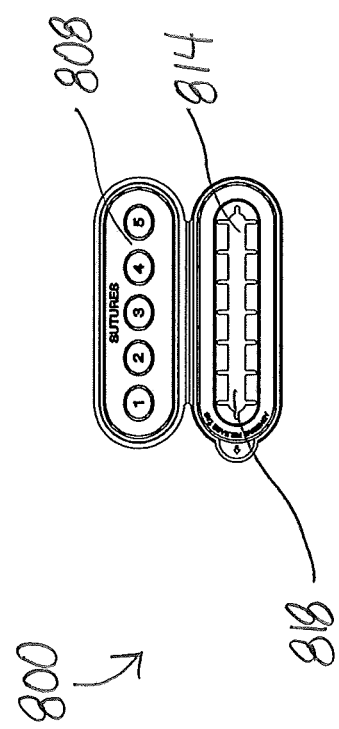
Figure 8G:
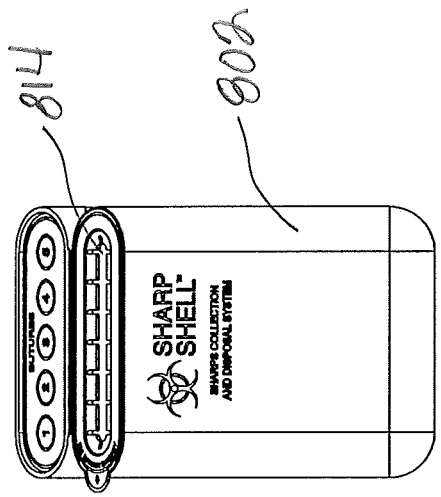
Figure 8M:

FIG. 8B illustrates an oblique view of the Sharpshell 800 in the closed configuration wherein the lid or top 804 has been closed. In other embodiments, the Sharpshell 800 can comprise a plurality of nested lids 804. The Sharpshell 800 can comprise external labeling 810.

Additional views of the Sharpshell 800 are provided in FIGS. 8C-8M wherein like numerals refer to the features and portions described above.

FIG. 8J shows how features 814 for grabbing and removing medical sharps from their handles or barrels may provide a molded engagement structure to allow the Luer locks 841 to be snapped into place and held while the syringe barrels are disconnected.

FIG. 8K shows how syringes 840 may be placed so as to engage hub receiver feature 814 as the syringe needles extend into the Sharpshell 800. The syringe barrels may then be removed while the syringe Luer locks 841 remain secured in hub receiver feature 818.

FIG. 9A illustrates another embodiment of a Sharpshell 900 comprising a side wall 902, a base 904, a top 906, a plurality of syringe needle entry apertures 908, one or more suture needle apertures 910, a needle re-capping station 912, an optional foam filler 914 shown in the cutaway portion of side wall 902, a suture needle window external cover 916, a suture needle internal retention window 918, one or more jam cleats or syringe needle retention mechanism 920, one or more scalpel blade aperture, 922, a suture needle drop port 922 (optional where a suture needle internal retention aperture 918 is provided), and an anti-skid base pad 924.

The suture needle aperture external cover 916 may be in the form of a releasable adhesive strip that may be replaced over suture needle internal retention aperture 918 after suture needles are placed into the internal storage volume of the Sharpshell 900 by inserting them through suture needle internal retention aperture 918.

The side wall 902 is shown as being axially elongate and linearly tapering from bottom to top. In other embodiments, the side wall 902 can comprise a radially concave cross-section that is flared outward more at the bottom than at the top. In one embodiment, side wall 902, base 904, and top 906 form a generally frusto-conical shape that has the concomitant advantages of placement stability, convenient manual handling by the user and ease of manufacture, such as through plastic molding techniques. In alternative embodiments, the top 906 can comprise a flat surface, a dome surface, as shown in FIGS. 9A and 9B, a conical surface, a conical shape with a flat at the top (i.e., itself frusto-conical), and the like. The side wall 902 and the top 906 (and in some embodiments the bottom 904) comprise the walls of a shell and are puncture-resistant to medical sharps under normal loading. The side wall 902, the top 906, and the bottom 904 can comprise materials such as, but not limited to, polystyrene, PVC, ABS, PET, PETG, polyamide, polyurethane, polycarbonate, polyethylene, polypropylene, and the like. The wall thickness of the side wall, 902, top 906, and bottom 904 can range from about 0.010 to about 0.125 inches with a preferred range of about 0.020 to about 0.050 inches.

The foam filler 914 can completely fill the Sharpshell 900, it can partially fill the Sharpshell 900, or it can be omitted. In alternative embodiments, the foam filler 914 may fill the Sharpshell 900 to an extent sufficient to be presented through suture needle internal retention aperture 918 and to be encountered by syringe needles extended through The foam filler 914 can comprise low density materials such as polyurethane, polycarbonate, and the like, and can further comprise materials with high friction and adhesive properties. The foam filler 914 can comprise open celled configurations that allow for absorption and capillary extraction and dispersal of liquids injected therein, thus preventing any leakage from the foam to the exterior of the Sharpshell 900.

The apertures 908 can comprise color coding, shape coding or other methodology to facilitate matching with specific sized medical sharps. The aperture 908 can be configured for the removal of hypodermic needle hubs from the syringe barrels, or for grabbing the hypodermic needle and retaining it within the Sharpshell 900.

FIG. 9B illustrates a top view of the Sharpshell 900 further comprising the side wall 902, the top 906, the one or more syringe needle apertures 908, the suture needle aperture 910, the suture needle aperture external cover 916, and the needle recapping station 912.

One or more aperture 908 can comprise a shape configured to accept a scalpel handle, blade, or combination thereof. The aperture 908 configured for a scalpel can comprise a rectangular configuration or profile and be sized to have a friction fit with the scalpel handle. The aperture 908, configured to accept a hypodermic needle can comprise a cross or X-shaped fenestration with a circular center such that a syringe needle hub will insert and catch within the aperture 908 by friction or resistance to rotation, which can facilitate removal.

The jam cleat 920 can be affixed to the side wall 902, to the top 906, or both. The jam cleat 920 can comprise a thin sheet of hardened metal comprising fenestrations and can be pre-bent to deflect in the direction of insertion of a hypodermic needle. In a preferred embodiment, the jam cleat 920 can comprise a small central hole, smaller than the diameter of a hypodermic needle, and a plurality of petals, ranging in number from two to ten or more, that can easily deflect in one direction but not the other. The metal thickness of the jam cleat 920 can range from about 0.001 to about 0.025 inches. The material can comprise stainless steel, hard steel, chrome steel, MP-32N titanium, nitinol, or the like. In a configuration for a scalpel blade, the jam cleat 920 can comprise two petals, separated along a single line, instead of three or four lines, for example, separated by a Y or X.

The jam cleat 920 can also comprise one or more hinged projections or arms with the surfaces toward which a medical sharp is inserted comprising one or more sharp edges, pins, needles, serrations, adhesives, or the like. The jam cleat 920 of this embodiment can be spring loaded to close against the medical sharp but be oriented such that the sharp can be pushed alongside the jam cleat projections which are angled away from the medical sharp entry point. As the medical sharp is withdrawn, the jam cleat closes ever more tightly and grabs the medical sharp with increasing force.

In yet another embodiment, the jam cleat 920 can comprise polymeric materials with a high-tack adhesive using similar configurations. However, the jam cleat 920 can also comprise a cylinder of gel or adhesive which grabs anything inserted therethrough and prevents or restricts extraction or withdrawal therefrom.

The jam cleat 920 can be backed up with a membrane or seal that prevents any leakage outside of the Sharpshell 900. The jam cleat 920 is advantageously positioned so that an inserted sharp, having a handle, hub or barrel, extends sufficiently through the aperture 908 and through a sharps removal feature, but does not extend into the jam cleat 920, which is configured to accept and catch only on narrow or small diameter objects such as the hypodermic needle or scalpel blade. Thus, there may be a space between the aperture 908 and the jam cleat 920.

The Sharpshell 900, is configured to be small, available at the point of use, compact, stable, and provides a secure method to increase healthcare staff needlestick safety. The Sharpshell 900 can be delivered within a medical procedure kit, or it can be provided separately. The Sharpshell 900 can be provided sterilized so it can be placed within the sterile field, which is generally the point of use. The Sharpshell 900 can be separated from a procedure kit to facilitate disposal in the smallest possible envelope. The Sharpshell 900 facilitates the collection and safe transport of contaminated medical sharps to a required disposal facility station. The Sharpshell 900 can be manipulated with one hand so another hand is not needed to stabilize it while inserting medical sharps.

The top cap 906 can be flattened around the needle re-capping station 912 to differentiate this port 912 of the Collection and Containment Station and to facilitate its use during a medical procedure. The re-capping port 912 can also comprise internal grooves or ridges to match the design of the hand grips on typical needle caps The ports 908 for the hypodermic syringes are on the curved portion of the top cap 906 to orient and direct the medical sharps to the center of the containment chamber 914. Also the port 908 can comprise an about $\frac{1}{8}$" to $\frac{1}{4}$" long internal flange, wider at the top with grooves and narrowing at the bottom to accommodate, tightly grip, and facilitate removal of various sizes of typically available needle hubs.

The suture needle drop port 922 can be round, as illustrated, or elongated, elliptical, or the like, and covers part of the top cap 906 and part of the side 902 to differentiate its function from other ports of the Sharpshell 900 and allows for convenient and stable, one handed, insertion and drop of needles and sutures when using standard suture holding devices. The suture needle drop port 900 can further comprise a covering of elastomeric material, adhesives, or the like.

The scalpel port can be located on the curved portion of the top cap 906 and can be elongated to differentiate its function from that of the suture drop port 922, hypodermic needle ports 908, or the recapping port 912. The scalpel port can also comprise an about ⅛" to ¼" molded internal flange, wider at the top to accommodate various sizes and designs of scalpels and to provide additional support for collection and containment Optionally covering the inside of the top cap 906 can include a flexible coating such as a gel/silicone type material to facilitate retention of the contaminated sharps. Opening around the suture drop is typically uncoated to facilitate dropping to the bottom. The bottom however, can also be coated with the flexible coating gel/silicone to help retain any sharps entering the containment chamber.

In a preferred embodiment, appropriate surfaces near the ports are labeled to indicate preferred use.

An external label can be attached to the side of the Sharpshell 900 to indicate the product name, instructions for use, warnings, cautions, and BIOHAZARD symbol warnings.

Figure 9C:
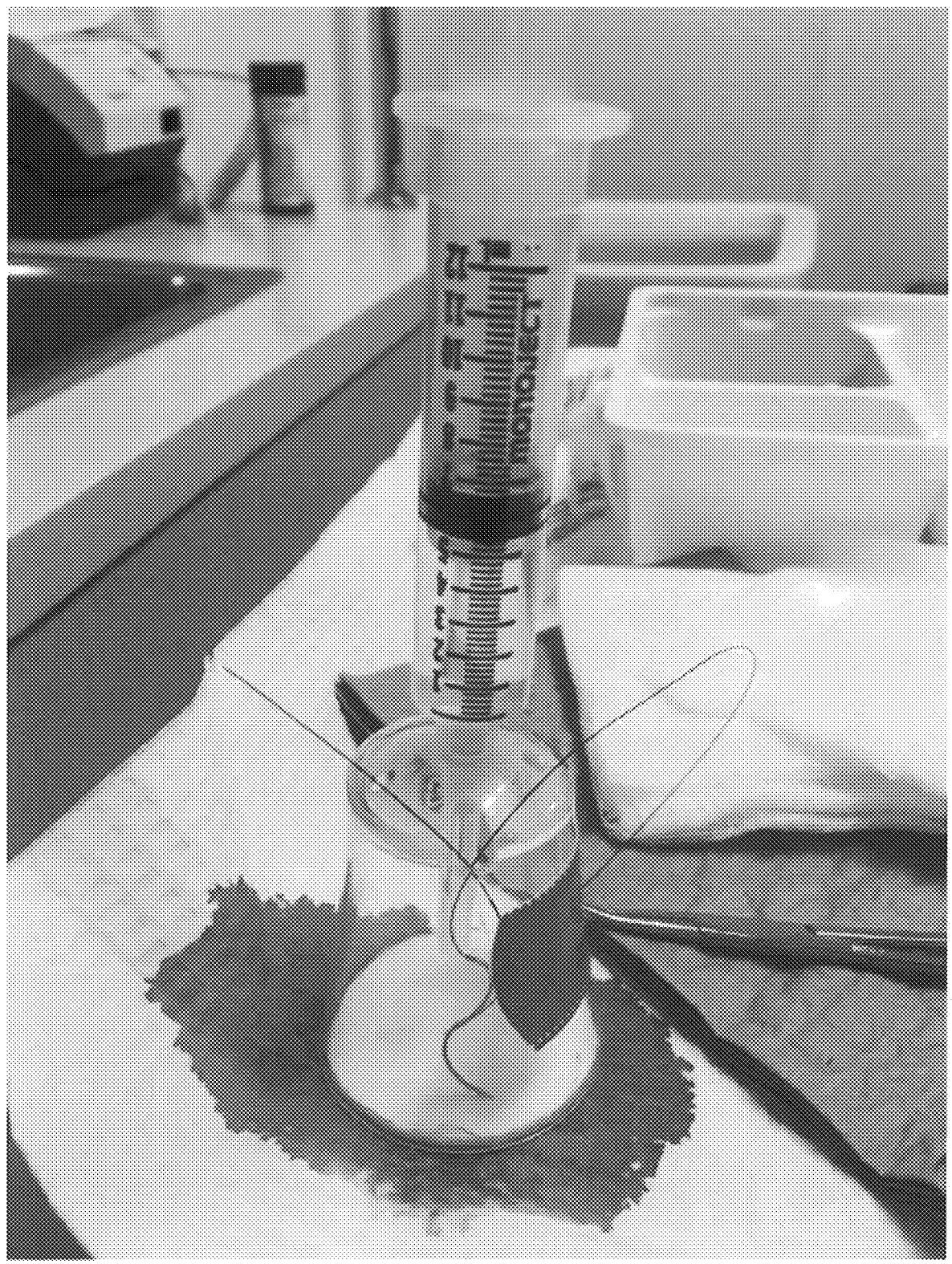
FIGS. 9C-9G provide additional views of the Sharpshell 900 of FIGS. 9A and 9B.
Figure 9D:
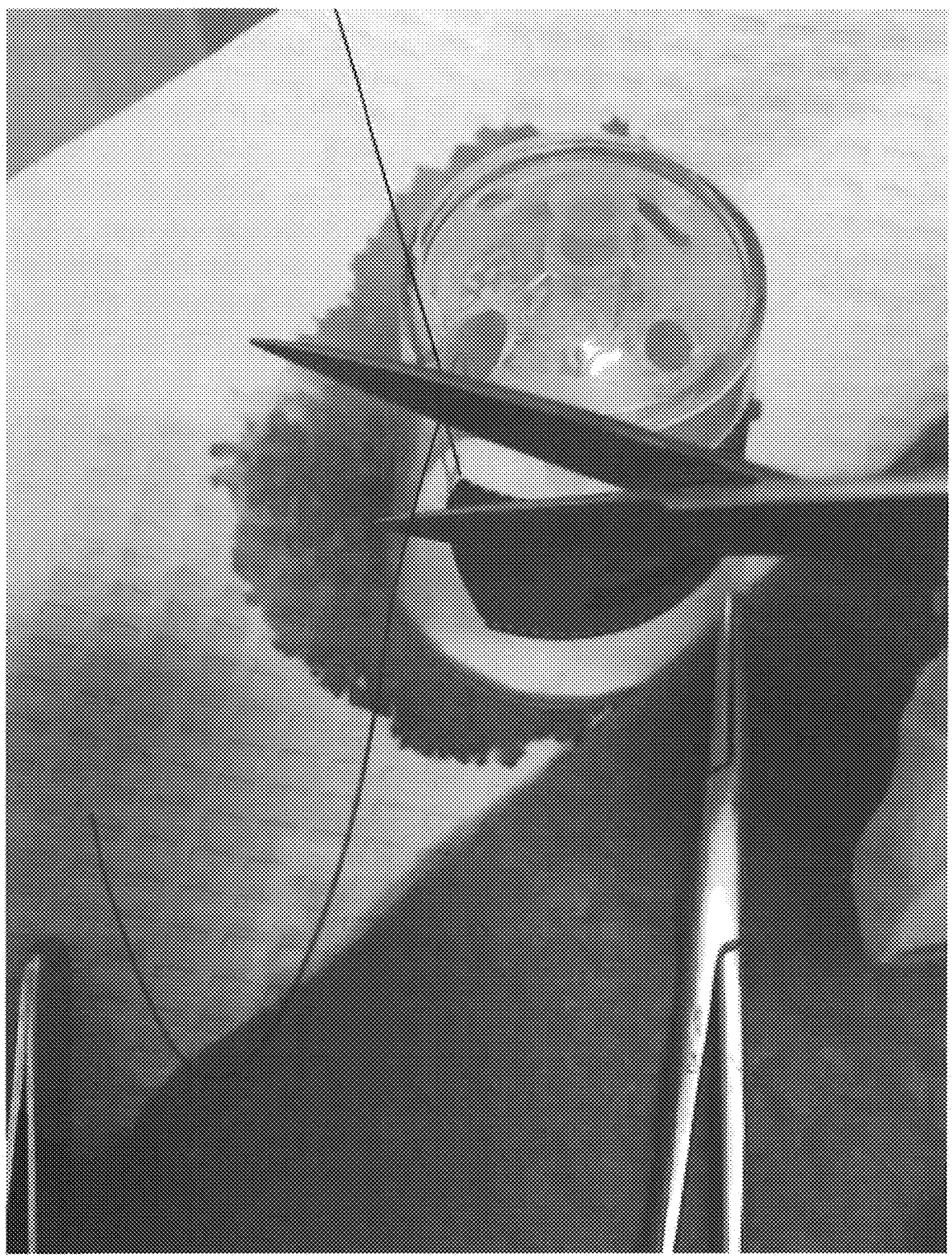
Figure 9E:
Figure 9F:
Figure 9G:
Figure 10:
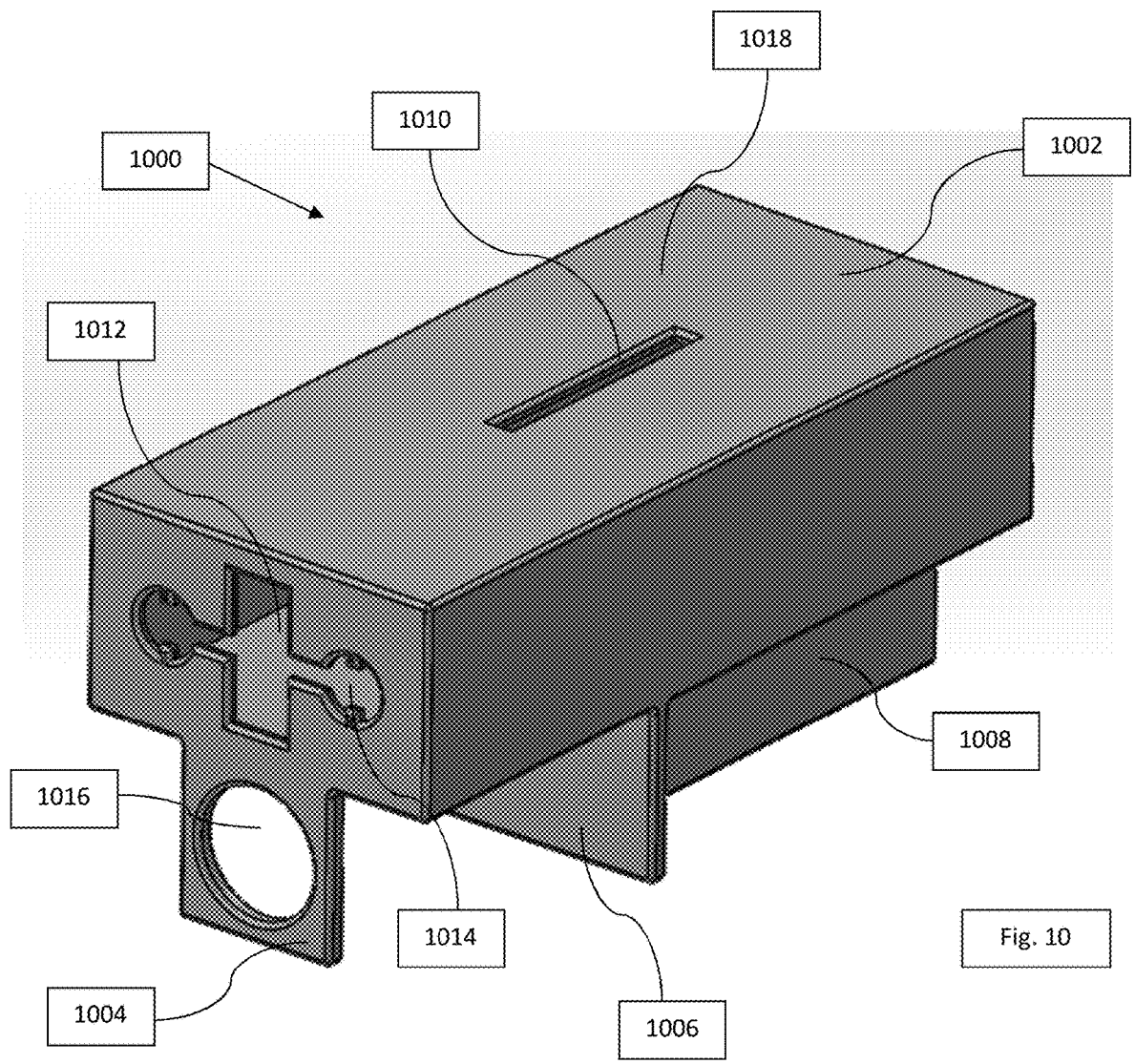

FIGS. 9C-9G provide additional photographic views of the Sharpshell 900 of FIGS. 9A and 9B in various stages of use during a medical or surgical procedure.

Figure 10:
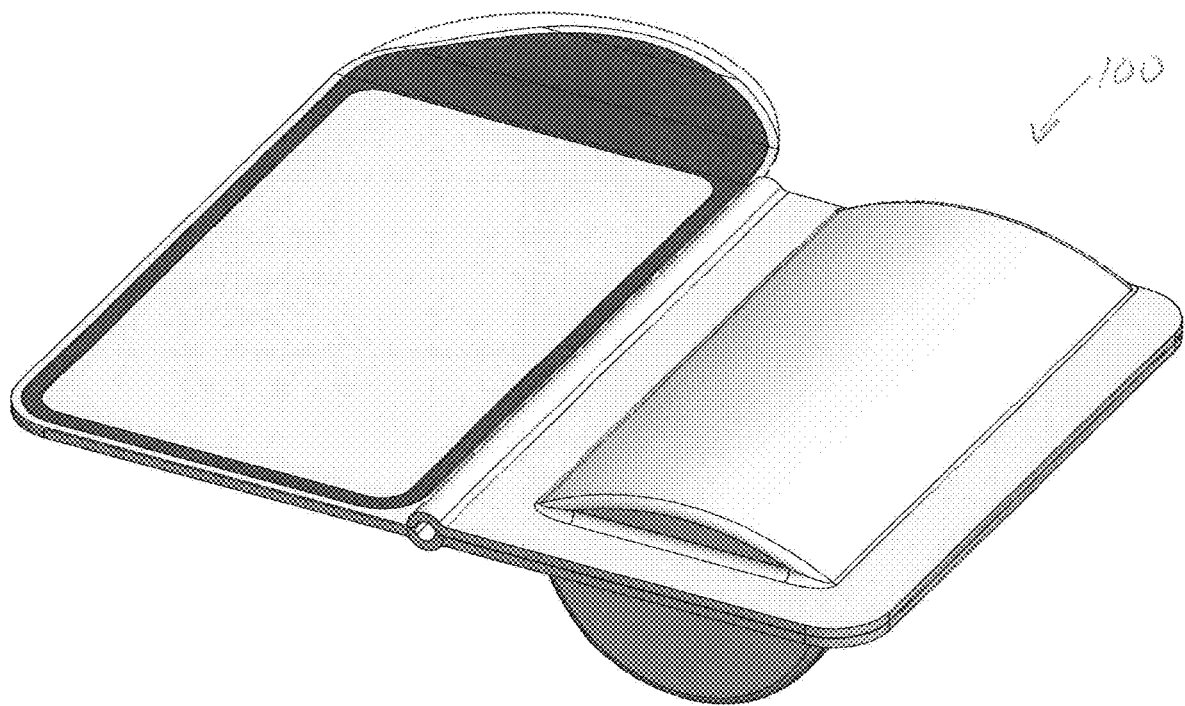

FIG. 10 illustrates a Sharpshell 1000 in oblique view. The Sharpshell 1000 comprises a non-openable shell 1002 further comprising a central volume 1018, a standoff 1004 comprising a first receiver 1016 for a needle exchange cap, a needle exchange cap backstop 1006, a stabilizer 1008, a suture needle slot 1010, a scalpel blade receiver 1012, and a plurality of hypodermic needle receivers 1014.

Referring to FIG. 10, the first receiver 1016 can comprise an opening that is circular or rectangular that allows for horizontal needle parking and recapping. The syringe needle cap can be placed between the opening and the solid backstop manually or by sliding off of the syringe. Recapping can be performed, single handed, by holding the syringe and sliding the sharp point into the supported cap holder. The first receiver 1016 opening can be horizontal or vertical, depending on desired use.

The needle exchange cap backstop 1006 or resting block can also provide stability support for the unit when it is standing vertically to accept needles, scalpels, or the like. The backstop 1006, in the illustrated embodiment, can provide horizontal stability to prevent tipping of the Sharpshell 1000. The combination of receiving space and back rest provide elevated and secure support for inserting sutures through the top opening of the first receiver 1016.

The suture needle slot 1010 is optimized for depositing suture needles therein. The suture needle slot 1010 can be located on the top surface of the device, as illustrated. The suture needle slot 1010 can comprise walls which are graduated oblique to the axis of the slot 1010. In this embodiment, the outermost portion of the slot 1010 can be wider or narrower than the innermost portion of the slot 1010. The slot or opening 1010 can have flat edges or graduate towards the center to prevent sutures from falling back out. The slot 1010 can also be configured to taper toward the edge to allow for trimming of suture material. Once the suture needle has been inserted through the slot 1010, it resides within the central volume or hollow cavity 1018. The cavity 1018 can be hollow or filled with various types of foam, gel, fibrous materials, or the like. In some embodiments, the cavity 1018 can be completely filled with foam, gel, or the like, or the cavity 1018 can comprise a volume 1018 that is partially filled with foam, gel, adhesives, or the like, to allow for the sutures to drop into the cavity but still for liquid absorption and retention of other sharps.

Referring to FIG. 10, the top surface of the shell 1002 can be flat (as illustrated) or slightly curved, either convex or concave.

The slot 1012 can be configured for grasping and capturing scalpel blades. The slot 1012 can be rectangular as shown, or it can be tapered or have uneven walls which facilitate grasping the scalpel handle, blade, or the like. The slot 1012 can comprise an opening that provides for friction, interference or mechanical grip on the scalpel whereby the entire sharp end is secured within the device's cavity. The slot or opening 1012 can also be used to discard of sutures if the user desires to stand the unit up on the short end during use. Sutures stored through this opening 1012 will not preclude a scalpel from also being stored in this location.

The hypodermic needle receivers 1014 can comprise circular openings with 2-4 teeth protruding into lumen for needle capture and removal. The teeth can be configured to dig into, and hold, a syringe needle hub while unscrewed from its syringe barrel. The teeth can be configured as a star pattern, a cross, an X, or in a pattern of two or three teeth equally spaced around the circumference. The length of the teeth (projection into the opening or slot) is such that when a needle is inserted into the cavity, the teeth secure the needle from spinning freely so that the needle can be unscrewed from the syringe safety and with one hand.

The opening, receiver, or slot 1014 may also have no teeth, but use a friction, interference or mechanical grip on the needle or needle barrel to achieve the same objective.

The Sharpshell 1000 can comprise dimensions suitable for portability and transport. The opening 1012 on the front face can comprise approximately a ⁷⁄₁₆"×³⁄₁₆" rectangle cutout for securing of a scalpel.

The syringe needle retention receivers 1014 can comprise one or more approximately ³⁄₁₆" diameter cutouts with 2 or more optional ¹⁄₃₂" teeth each that are designed to catch and release needles from a syringe barrel.

The slot 1010 can comprise approximately a ¹⁄₁₆"×³⁄₄" rectangle cutout on top for insertion of used suture needles. These dimensions can be tailored to meet the requirements of different types of suture needles. Needles can be dropped into the cavity 1018 and retained therein. A strip of tape or other closure can be used to secure the openings in the Sharpshell against egress of medical sharps trapped therein.

The recapping feature 1016 can comprise approximately a ¼" diameter hole for cap placement and recapping of needles with backstop material approximately 1" (range 0.5 to 1.5") away preventing needle cap from pushing all the way through.

The main cavity 1018, in the illustrated embodiment comprises dimensions of about 1.125"×2.5"×⅝". These dimensions can be adjusted to meet the needs of various types of medical sharps.

Referring to all embodiments described herein, a receiver can be termed a port, a window, an aperture, a fenestration, a slot, a hole, an opening, or any structure that permits access to the interior of the Sharpshell containment cavity or region behind a receiver. The term window, if defined as such, can also comprise a visually transparent panel over an opening that permits viewing of objects on the other side of the window.

Figure 11:
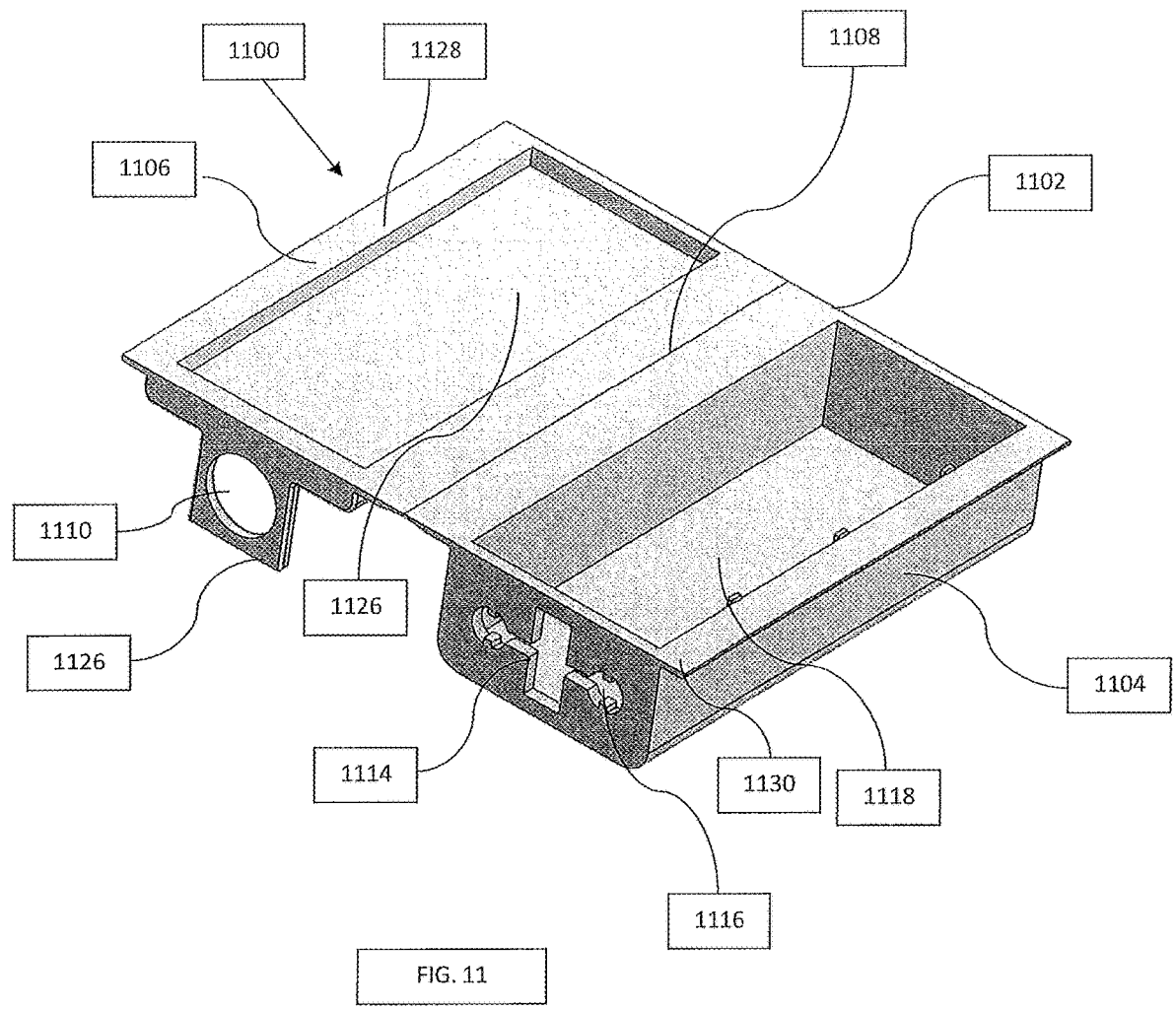
FIG. 11 illustrates a Sharpshell comprising a bottom portion, an openable top portion, and features to accept scalpels, needle exchange cap, and syringe needle hubs, according to one embodiment.

FIG. 11 illustrates a Sharpshell 1100 in the open configuration in oblique view. The Sharpshell 1100 comprises a shell 1102 further comprising a bottom portion 1104, a top portion 1106, a hinge 1108, a standoff 1126 comprising a first receiver 1110 for a needle exchange cap, a needle exchange cap backstop 1112, a scalpel receiver 1114, a plurality of hypodermic needle receivers 1116, a bottom central volume 1118, a top central volume 1126, a bottom foam pad 1120, an optional top foam pad 1122 (not shown), and a closure lock 1124.

Referring to FIG. 11, the Sharpshell Unit 1100 is composed of two halves: a top portion 1106 comprising a shallow clear puncture resistant cavity 1126 and a needle cap storage and placement device, and a bottom portion 1104 comprising a deeper cavity 1118 with storage and removal apparatus for suture, needles and scalpels.

The top portion 1106 comprises a shallow top cavity 1126 which can either be filled with foam or polypropylene or be left empty so that the user can see through to the sutures stored in the bottom cavity 1118. Materials filling the top cavity 1126, bottom cavity 1118, or both, would provide moisture absorption as well as further protect and secure the sharps in the device.

The needle cap storage and recapping feature can comprise an opening 1110 that can either be circular or rectangular that allows for horizontal needle parking and recapping. The syringe needle cap can be placed between the opening and the solid backstop 1112 manually or by sliding it off of the syringe barrel. Recapping can be performed by single handed by holding the syringe and sliding the sharp point into the supported cap holder. The recapping opening 1110 can be positioned or oriented either horizontal or vertical, depending on desired use.

The backstop 1112 can serve as a resting block for the Sharpshell 1100 to provide stability support for the Sharpshell 1100 unit, open or closed, when it is standing vertically to accept needles, or scalpels, or the like. The combination of receiving space 1110 and the back rest 1112 provide elevated and secure support for inserting sutures through the top opening.

The bottom portion 1104 is configured or adapted to hold and retain suture needles, with or without their sutures attached. The bottom cavity 1118 can be hollow or filled, in part or in whole, with various types of foam, gel, adhesive, fibers, or the like. The filler material or pads 1120 within the bottom cavity 1118 can be visually divided, using labels, shell material barriers or webs, or the like, to allow for placement and counting of the sutures inserted into the material. The Sharpshell 1100 comprises openings on the front face of the bottom portion 1104 of the unit.

The scalpel receiver 1114 comprises an opening that provides for friction, interference or mechanical grip on the scalpel whereby the entire sharp end is secured within the device's cavity 1118. The opening 1114 can also be used to discard of sutures if the user desires to stand the unit up on the short end during use. Sutures inserted through this opening 1114 will not preclude a scalpel from also being inserted and stored in this location.

The one or more syringe or hypodermic needle receivers 1116 can comprise circular openings, for example with about 2-4 teeth protruding into lumen for needle capture and removal. The teeth can be adapted to dig into and hold needle hub while unscrewed from syringe base. The hypodermic needle receivers 1116 can comprise star shaped patterns, X-patterns, diamond patterns, or the like, all configured to accept a syringe needle hub and prevent rotation of the hub while the barrel is being removed.

The top portion 1106 and the bottom portion 1104 are affixed to each other and operably connected via a living or mechanical hinge 1108.

Closure of the top portion 1106 against the bottom portion 1104 can be performed through locking mechanisms such as, but not limited to, a snap and hook, penetrating hook, or pressure fit mechanism. Closure can also be maintained using adhesives affixed to the flanges 1128 and 1130 surrounding the top portion 1106 and the bottom portion 1104. The adhesives can be protected using release paper prior to use. Additionally a double wall feature can be created by the overlaying of the top portion 1106 and portion 1104 to prevent liquid leakage and further enclose the sequestered sharps.

The size of the Sharpshell 1100 is adapted for compactness and ease of transport. The scalpel receiver comprises an approximately rectangular opening of about $7/16" \times 3/16"$ dimensions for securing a scalpel.

The syringe needle receiver can comprise between 1 and 6 each, approximately $3/16"$ diameter cutouts with between 1 and 4 inward projections about $1/32$ inch long.

The openings on front face of top half of unit can be sized as openings of approximately $1/4"$ diameter adapted for cap placement and recapping of needles with the backstop 1112 material located about 1" away.

Figure 12:
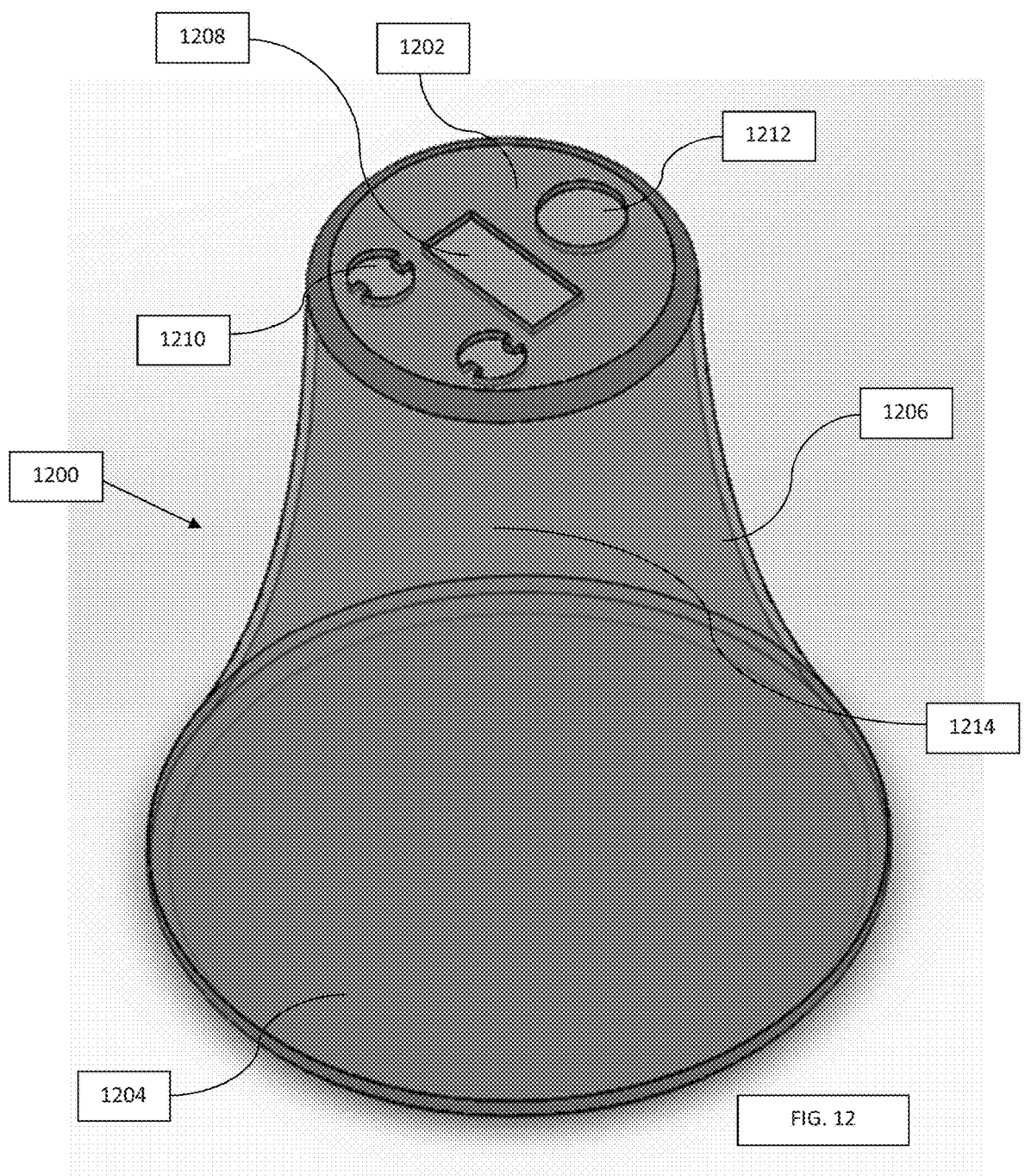
FIG. 12 illustrates a non-openable Sharpshell comprising an axially elongate structure with curvilinear sides, a wide base, and features to accept suture needles, scalpels, and hypodermic needles, according to one embodiment.

FIG. 12 illustrates a Sharpshell 1200 in oblique view. The Sharpshell 1200 comprises an axially elongate structure having a top 1202, a bottom 1204, and a side wall 1206. The top 1202 can comprise a scalpel blade receiver 1208, a plurality of hypodermic needle receivers 1210, and a needle recapping receiver 1212. The Sharpshell 1200 further comprises a central volume 1214.

Referring to FIG. 12, the scalpel blade receiver 1208 can further receive suture needles. The side wall 1206 can comprise a curvilinear contour, as shown. The curvilinear contour permits a wide base for increased or enhanced stability, strength, and rigidity of the structure, relative to straight side walls 1206. The side wall 1206, the top 1202, and the bottom 1204 can be transparent, translucent, opaque or a combination thereof. The side wall 1206, the top 1202, and the bottom 1204 can comprise labeling, instructions for use, warnings, and the like.

The central volume 1214, containment cavity, hollow space, or hollow cavity serves the purpose of or provides for depositing suture needles within the Sharpshell 1200.

The Sharpshell 1200 can comprise dimensions suitable for carrying in the hand and small enough to fit within permanent sharps disposal containers. In the illustrated embodiment, the Sharpshell 1200 comprises a diameter of about 1 inch at the top, about 2 inches at the base, and a height of about 2.25 inches. The top diameter can range from about 0.5 inches to about 2 inches. The bottom diameter can range from about 0.75 inches to about 3 inches. The height can range from about 1 inch to about 3 inches. The edges are beneficially rounded or filleted, for example with radii of about 0.02 to about 0.1 inches.

The needle recapping receiver can comprise a diameter of about 0.2 to about 0.3 inches. The diameter is configured to accept a syringe needle cap approximately $1/2$ or more inserted into the central cavity and with a press or friction fit to enhance stability but still allow removal of the cap.

The scalpel port or receiver can comprise dimensions of about $7/16"$ long by $3/16"$ wide and can comprise a cutout for securing of scalpel and insertion of used suture needles. Needles are dropped into the cavity first then scalpel is inserted and locked into place.

The one or more hypodermic needle or syringe needle receiver 1210 can comprise holes or fenestrations of about 3/16" diameter, ranging from about 0.1 to about 0.2 inches in diameter. The syringe needle receivers 1210 can comprise cutouts with one or more teeth each that are designed to catch and release needles from a syringe. The teeth, in the illustrated embodiment, can comprise dimensions of about 1/32 inches.

The syringe needle receivers 1210 can further comprise jam cleats or other features to irreversibly prevent removal of a syringe needle inserted therethrough and can further comprise seal features to prevent fluid escape through the needle receivers 1210 or any other port.

FIG. 13A illustrates another embodiment of a Sharpshell 1300 which may be considered a variant of Sharpshell 900 and 1200 described above, and comprising a side wall 1302, a base 1304, a top 1306, a plurality of syringe needle entry apertures or "windows" 1308, one or more suture needle windows, such as suture needle window 1310, a needle re-capping station 1312, an optional foam filler 1314 shown in the cutaway portion of side wall 1302 and exposed by suture needle window 1310, a suture needle window external cover 1316 which may provide a removable cover to suture needle window 1310, one or more teeth or protrusions or syringe needle retention mechanism 1320, one or more scalpel blade window 1322, and an anti-skid base pad 1324.

The suture needle window external cover 1316 may be in the form of a releasable adhesive strip that may be replaced over suture needle window 1310 after suture needles are placed into the internal storage volume of the Sharpshell 1300 by inserting them through suture needle window 1310.

The side wall 1302 is shown as being axially elongate and linearly tapering from bottom to top. In other embodiments, the side wall 1302 can comprise a radially concave cross-section that is flared outward more at the bottom than at the top. In one embodiment, side wall 1302, base 1304, and top 1306 form a generally frusto-conical shape that has the concomitant advantages of placement stability, convenient manual handling by the user and ease of manufacture, such as through plastic molding techniques. In alternative embodiments, the top 1306 can comprise a flat surface, a dome surface, as shown in FIGS. 13A and 13B, a conical surface, a conical shape with a flat at the top (i.e., itself frusto-conical), and the like. The side wall 1302 and the top 1306 (and in some embodiments the bottom 1304) comprise the walls of a shell and are puncture-resistant to medical sharps under normal loading. The side wall 1302, the top 1306, and the bottom 1304 can comprise materials such as, but not limited to, polystyrene, PVC, ABS, PET, PETG, polyamide, polyurethane, polycarbonate, polyethylene, polypropylene, and the like. The wall thickness of the side wall, 1302, top 1306, and bottom 1304 can range from about 0.010 to about 0.125 with a preferred range of about 0.020 to about 0.050 inches.

The optional foam filler 1314 can completely fill the Sharpshell 1300, it can partially fill the Sharpshell 1300, or it can be omitted. In alternative embodiments, the foam filler 1314 may fill the Sharpshell 1300 to an extent sufficient to be presented through suture needle window 1310 and to be encountered by syringe needles extended through the window. The foam filler 1314 can comprise low density materials such as polyurethane, polycarbonate, and the like, and can further comprise materials with high friction and adhesive properties. The foam filler 1314 can comprise open celled configurations that allow for absorption and capillary extraction and dispersal of liquids injected therein, thus preventing any leakage from the foam to the exterior of the Sharpshell 1300.

The needle windows, such as suture needle window 1310, can comprise color coding, shape coding or other methodology to facilitate matching with specific sized medical sharps. The windows, such as hypodermic needle window 1308, can be configured for the removal of hypodermic needle hubs from the syringe barrels, or for grabbing the hypodermic needle and retaining it within the Sharpshell 1300.

FIG. 13B illustrates a top view of the Sharpshell 1300 further comprising the side wall 1302, the top 1306, the one or more syringe needle windows 1308, the suture needle window 1310, the suture needle window external cover 1316, and the needle recapping station 1312.

One or more window 1322 can comprise a shape configured to accept a scalpel handle, blade, or combination thereof. The window 1322 configured for a scalpel can comprise a rectangular configuration or profile and be sized to have a friction fit with the scalpel handle. The window(s) 1308, configured to accept a hypodermic needle can comprise a cross or X-shaped fenestration with a circular center such that a syringe needle hub will insert and catch within the window(s) 1308 by friction or resistance to rotation, which can facilitate removal. These windows may also be in the form of a two-toothed design as shown in FIG. 13A.

The jam cleat 1320 can be affixed to the top 1306. The jam cleat 1320 can comprise a thin sheet of hardened metal comprising fenestrations and can be pre-bent to deflect in the direction of insertion of a hypodermic needle. In a preferred embodiment, the jam cleat 1320 can comprise a small central hole, smaller than the diameter of a hypodermic needle, and a plurality of petals, ranging in number from two to ten or more, that can easily deflect in one direction but not the other. The metal thickness of the jam cleat 1320 can range from about 0.001 to about 0.025 inches. The material can comprise stainless steel, hard steel, chrome steel, MP-32N titanium, nitinol, or the like. In a configuration for a scalpel blade, the jam cleat 1320 can comprise two petals, separated along a single line, instead of three or four lines, for example, separated by a Y or X.

The jam cleat 1320 can also comprise one or more hinged projections or arms with the surfaces toward which a medical sharp is inserted comprising one or more sharp edges, pins, needles, serrations, adhesives, or the like. The jam cleat 1320 of this embodiment can be spring loaded to close against the medical sharp but be oriented such that the sharp can be pushed alongside the jam cleat projections which are angled away from the medical sharp entry point. As the medical sharp is withdrawn, the jam cleat closes ever more tightly and grabs the medical sharp with increasing force.

In yet another embodiment, the jam cleat 1320 can comprise polymeric materials with a high-tack adhesive using similar configurations. However, the jam cleat 1320 can also comprise a cylinder of gel or adhesive which grabs anything inserted therethrough and prevents or restricts extraction or withdrawal therefrom.

The jam cleat 1320 can be backed up with a membrane or seal that prevents any leakage outside of the Sharpshell 1300. The jam cleat 1320 is advantageously positioned so that an inserted sharp, having a handle, hub or barrel, extends sufficiently through the window 1308 and through a sharps removal feature, but does not extend into the jam cleat 1320, which is configured to accept and catch only on narrow or small diameter objects such as the hypodermic needle or scalpel blade. Thus, there may be a space between the window 1308 and the jam cleat 1320.

The Sharpshell 1300, is configured to be small, available at the point of use, compact, stable, and provides a secure method to increase healthcare staff needlestick safety. The Sharpshell 1300 can be delivered within a medical procedure kit, or it can be provided separately. The Sharpshell 1300 can be provided sterilized so it can be placed within the sterile field, which is generally the point of use. The Sharpshell 1300 can be separated from a procedure kit to facilitate disposal in the smallest possible envelope. The Sharpshell 1300 facilitates the collection and safe transport of contaminated medical sharps to a required disposal facility station. The Sharpshell 1300 can be manipulated with one hand so another hand is not needed to stabilize it while inserting medical sharps.

The top cap 1306 can be flattened around the needle re-capping station 1312 to differentiate this port 1312 of the Collection and Containment Station and to facilitate its use during a medical procedure. The re-capping port 1312 can also comprise internal grooves or ridges to match the design of the hand grips on typical needle caps The ports 1308 for the hypodermic syringes are on the curved portion of the top cap 1306 to orient and direct the medical sharps to the center of the containment chamber 1314. Also the port 1308 can comprise an about ⅛" to ¼" long internal flange, wider at the top with grooves and narrowing at the bottom to accommodate, tightly grip, and facilitate removal of various sizes of typically available needle hubs; or the port 1308 may also be in the form with protruding teeth into the window, such as the two-toothed design as shown in FIG. 13A.

The scalpel port 1322 can be located on the curved portion of the top cap 1306 and can be elongated to differentiate its function from that of hypodermic needle ports 1308 or the recapping port 1312. The scalpel port 1322 can also comprise an about ⅛" to ¼" molded internal flange, wider at the top to accommodate various sizes and designs of scalpels and to provide additional support for collection and containment Optionally covering the inside of the top cap 1306 can include a flexible coating such as a gel/silicone type material to facilitate retention of the contaminated sharps. Opening around the suture drop is typically uncoated to facilitate dropping to the bottom. The bottom however, can also be coated with the flexible coating gel/silicone to help retain any sharps entering the containment chamber.

In a preferred embodiment, appropriate surfaces near the ports are labeled to indicate preferred use.

An external label can be attached to the side of the Sharpshell 1300 to indicate the product name, instructions for use, warnings, cautions, and BIOHAZARD symbol warnings.

FIGS. 13C-13G provide additional views of the Sharpshell 1300 of FIGS. 13A and 13B in various stages of use during a medical or surgical procedure.

The devices described herein, can all comprise a syringe needle exchange area, which can comprise a well into which a syringe needle cap can be inserted and which ideally prevents rotation of the syringe needle cap within a collection pad or shell structure. The syringe needle exchange area is ideally oriented vertically with respect to a planar surface which can rest stable on a table top. A syringe needle is inserted without requiring a hand to hold the Sharpshell to prevent inadvertently sticking the syringe needle into a hand. In other embodiments, the syringe needle exchange area can comprise a built in structure similar to a syringe needle cap, which is an axially elongate hollow structure comprising a center lumen and a cross or X structure to grab the exterior of a syringe needle hub by friction or press fit.

Application of the Sharpshell system and methods reduces the risk that a medical caregiver will use a hypodermic needle, scalpel, or the like on a patient, turn around and accidentally stab a co-worker while trying to put the sharp into its receptacle. Such a scenario is particular disadvantageous when the patient is a vector for highly pathogenic organisms such as those for hepatitis, human immunodeficiency virus (HIV), and the like. The Sharpshell system is universal and does not require that each individual sharp is specially designed to retract or self-blunt. The Sharpshell and the methods of using the Sharpshell reduce the risk of an inadvertent contamination in the medical environment. The Sharpshell system can be provided within a hospital, emergency vehicle, or medical center but it can also be provided at any point of use outside a hospital or traditional medical center where medical intervention is provided.

The present invention may be embodied in other specific forms without departing from its spirit or essential characteristics. For example, the Sharpshell can, instead, be configured as a single monolithic slab of gel material that entraps the sharp and hardens to embed the sharp. The Sharpshell receptacle and dispenser may also be configured to accept such hardenable gel. The described embodiments are to be considered in all respects only as illustrative and not restrictive. Features described for a given embodiment can be applied to other embodiments disclosed herein while remaining within the scope of the disclosure. Materials and dimensions specified for a given embodiment may also be used for other embodiments described herein. The scope of the invention is therefore indicated by the appended claims rather than the foregoing description. All changes that come within the meaning and range of equivalency of the claims are to be embraced within their scope.

What is claimed is:

1. An apparatus adapted for entrapment and disposal of medical sharps such apparatus comprising:
    a shell defining storage volume, said shell having a top portion, a side wall portion and a bottom base portion, the base portion having an outer perimeter larger than an outer perimeter of said top portion, said shell adapted to stand upright upon said base so as to present an exposed said top portion and an exposed said side wall portion;
    said top portion includes a dome shape and includes (a) at least one needle re-capping aperture positioned about an uppermost portion of said dome shape of said top portion and adapted to releasably accept a syringe cap so as to allow a capped syringe to be releasably extended into said storage volume and (b) at least one syringe needle entry aperture positioned about a curved portion of said dome shape of said top portion and adapted to capture and hold a syringe hub as its syringe needle extends into said storage volume and (c) at least one scalpel blade window in said top portion positioned about said curved portion of said dome shape of said top portion; and
    a suture needle aperture adapted to receive suture needles into said storage volume said suture needle aperture extending from said top portion into said storage volume and being open through a portion of said side wall portion; and a high-friction pad contained within said shell and exposed through said at least one syringe needle entry aperture and said suture needle aperture.

2. An apparatus according to claim 1 further comprising a foam filler material positioned within said storage volume.

3. An apparatus according to claim 1, additionally comprising a cover piece releasably affixed to said side wall portion and at least partially covering said suture needle aperture.

4. An apparatus according to claim 3 wherein said cover piece comprises a releasable adhesive strip.

5. An apparatus according to claim 1, said apparatus contained within a procedure tray or kit.

6. An apparatus according to claim 1, said apparatus affixed to a procedure tray or kit.

7. An apparatus according to claim 1 wherein at least a portion of said shell is transparent.

8. An apparatus according to claim 1 wherein said base portion is of a material adapted to resist sliding.

9. An apparatus according to claim 1 further comprising at least one projection within said needle re-capping aperture and said at least one syringe needle entry aperture.

10. An apparatus adapted for entrapment and disposal of medical sharps such apparatus comprising:
    a shell defining storage volume, said shell having a top portion, a side wall portion and a bottom base portion, the base portion being at least as large in area as said top portion, said shell adapted to stand upright upon said base so as to present an exposed said top portion and an exposed said side wall portion;
    said top portion including (a) at least one syringe cap holding aperture adapted to releasably accept a syringe cap so as to allow a capped syringe to be releasably extended into said storage volume and (b) at least one syringe capture aperture adapted to capture and hold a syringe hub as its syringe needle extends into said storage volume and (c) at least one scalpel blade window in said top portion; and
    a suture needle aperture adapted to receive suture needles into said storage volume, said suture needle aperture extending from said top portion into said storage volume and being open through a portion of said wall portion; and
    a cover piece releasably affixed to said side wall portion and at least partially covering said suture needle aperture, said cover piece including a releasable adhesive strip
    wherein said at least one syringe cap holding aperture is positioned about an uppermost portion of said dome shape of said top portion,
    wherein said at least one syringe capture aperture is positioned about a curved portion of said dome shape of said top portion, and
    wherein said at least one scalpel blade window is positioned about said curved portion of said dome shape of said top portion.

11. An apparatus according to claim 10 wherein said base portion is of a material adapted to resist sliding friction as compared to the material comprised by said a top portion and side wall portion.

12. An apparatus according to claim 10 wherein said suture needle aperture extends into both said top portion and side wall portion.

13. An apparatus according to claim 10, wherein said shell is frustoconical in shape.

14. An apparatus according to claim 10, wherein said top portion includes a dome surface.

* * * * *